(12) United States Patent
Taniguchi et al.

(10) Patent No.: US 9,029,388 B2
(45) Date of Patent: May 12, 2015

(54) CONDENSED HETEROCYCLIC COMPOUND

(75) Inventors: Takahiko Taniguchi, Kanagawa (JP); Jun Kunitomo, Kanagawa (JP); Masato Yoshikawa, Kanagawa (JP); Tomoaki Hasui, Kanagawa (JP); Eiji Honda, Kanagawa (JP); Keisuke Imamura, Kanagawa (JP); Haruhi Kamisaki, Kanagawa (JP); Shinkichi Suzuki, Kanagawa (JP); Kasei Miura, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/002,439

(22) PCT Filed: Mar. 15, 2012

(86) PCT No.: PCT/JP2012/056769
§ 371 (c)(1),
(2), (4) Date: Aug. 30, 2013

(87) PCT Pub. No.: WO2012/124782
PCT Pub. Date: Sep. 20, 2012

(65) Prior Publication Data
US 2013/0331409 A1    Dec. 12, 2013

(30) Foreign Application Priority Data

Mar. 16, 2011   (JP) ................... 2011-058562

(51) Int. Cl.
*C07D 471/14* (2006.01)
*C07D 471/04* (2006.01)
*C07D 519/00* (2006.01)

(52) U.S. Cl.
CPC ............ *C07D 471/14* (2013.01); *C07D 471/04* (2013.01); *C07D 519/00* (2013.01)

(58) Field of Classification Search
None
See application file for complete search history.

(56) References Cited

U.S. PATENT DOCUMENTS

| 7,652,035 | B2 | 1/2010 | Lanier et al. |
| 7,994,204 | B2 | 8/2011 | Ono et al. |
| 8,053,438 | B2 | 11/2011 | Allen et al. |
| 8,178,538 | B2 | 5/2012 | Alberati et al. |
| 8,247,418 | B2 | 8/2012 | Allen et al. |
| 8,318,718 | B2 | 11/2012 | Allen et al. |
| 8,329,700 | B2 | 12/2012 | Allen et al. |
| 8,354,411 | B2 | 1/2013 | Taniguchi et al. |
| 8,435,995 | B2 | 5/2013 | Taniguchi et al. |
| 8,513,251 | B2 | 8/2013 | Taniguchi et al. |
| 2003/0013733 | A1 | 1/2003 | Apodaca et al. |
| 2004/0167336 | A1 | 8/2004 | Apodaca et al. |
| 2005/0288323 | A1 | 12/2005 | Apodaca et al. |
| 2007/0155779 | A1 | 7/2007 | Verhoest et al. |
| 2008/0064719 | A1 | 3/2008 | Lanier et al. |
| 2008/0090834 | A1 | 4/2008 | Hoover et al. |
| 2009/0182144 | A1 | 7/2009 | Ono et al. |
| 2009/0263322 | A1 | 10/2009 | Apodaca et al. |
| 2010/0056515 | A1 | 3/2010 | Aso et al. |
| 2010/0125062 | A1 | 5/2010 | Allen et al. |
| 2010/0137278 | A1 | 6/2010 | Allen et al. |
| 2010/0152193 | A1 | 6/2010 | Alberti et al. |
| 2010/0190832 | A1 | 7/2010 | Surolia |
| 2010/0197651 | A1 | 8/2010 | Taniguchi et al. |
| 2011/0160182 | A1 | 6/2011 | Allen et al. |
| 2011/0160202 | A1 | 6/2011 | Allen et al. |
| 2011/0319394 | A1 | 12/2011 | Taniguchi et al. |
| 2012/0028951 | A1 | 2/2012 | Taniguchi et al. |
| 2012/0277204 | A1 | 11/2012 | Taniguchi et al. |
| 2012/0277209 | A1 | 11/2012 | Allen et al. |
| 2012/0277430 | A1 | 11/2012 | Taniguchi et al. |
| 2012/0277431 | A1 | 11/2012 | Taniguchi et al. |
| 2013/0079325 | A1 | 3/2013 | Allen et al. |
| 2013/0137675 | A1 | 5/2013 | Taniguchi et al. |

(Continued)

FOREIGN PATENT DOCUMENTS

| JP | 2010-507664 | 3/2010 |
| WO | 02/24695 | 3/2002 |

(Continued)

OTHER PUBLICATIONS

International Search Report issued Jun. 12, 2012 in International (PCT) Application No. PCT/JP2012/056769.

(Continued)

*Primary Examiner* — Timothy R Rozof

(74) *Attorney, Agent, or Firm* — Wenderoth, Lind & Ponack, L.L.P.

(57) ABSTRACT

The present invention provides a compound having a superior PDE10A inhibitory action and use thereof. The compound is a compound represented by the following formula (I):

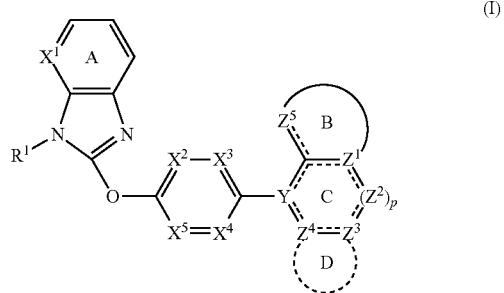

wherein each symbol is as defined in the present specification, or a salt thereof.

13 Claims, 1 Drawing Sheet

(56) References Cited

U.S. PATENT DOCUMENTS

| | | |
|---|---|---|
| 2013/0137700 A1 | 5/2013 | Hasui et al. |
| 2013/0150344 A1 | 6/2013 | Yoshikawa et al. |
| 2013/0172292 A1* | 7/2013 | Raker et al. ............ 514/63 |
| 2013/0172328 A1 | 7/2013 | Taniguchi et al. |

FOREIGN PATENT DOCUMENTS

| | | |
|---|---|---|
| WO | 2006/044821 | 4/2006 |
| WO | 2006/072828 | 7/2006 |
| WO | 2007/077490 | 7/2007 |
| WO | 2007/091570 | 8/2007 |
| WO | 2008/001182 | 1/2008 |
| WO | 2008/004117 | 1/2008 |
| WO | 2010/057121 | 5/2010 |
| WO | 2010/057126 | 5/2010 |
| WO | 2010/063610 | 6/2010 |
| WO | 2010/090737 | 8/2010 |
| WO | 2011/163355 | 12/2011 |
| WO | 2012/018058 | 2/2012 |
| WO | 2012/018059 | 2/2012 |
| WO | 2012/018909 | 2/2012 |
| WO | 2012/020780 | 2/2012 |

OTHER PUBLICATIONS

PCT/ISA/210 issued in corresponding International Application No. PCT/JP2012/056769.

* cited by examiner

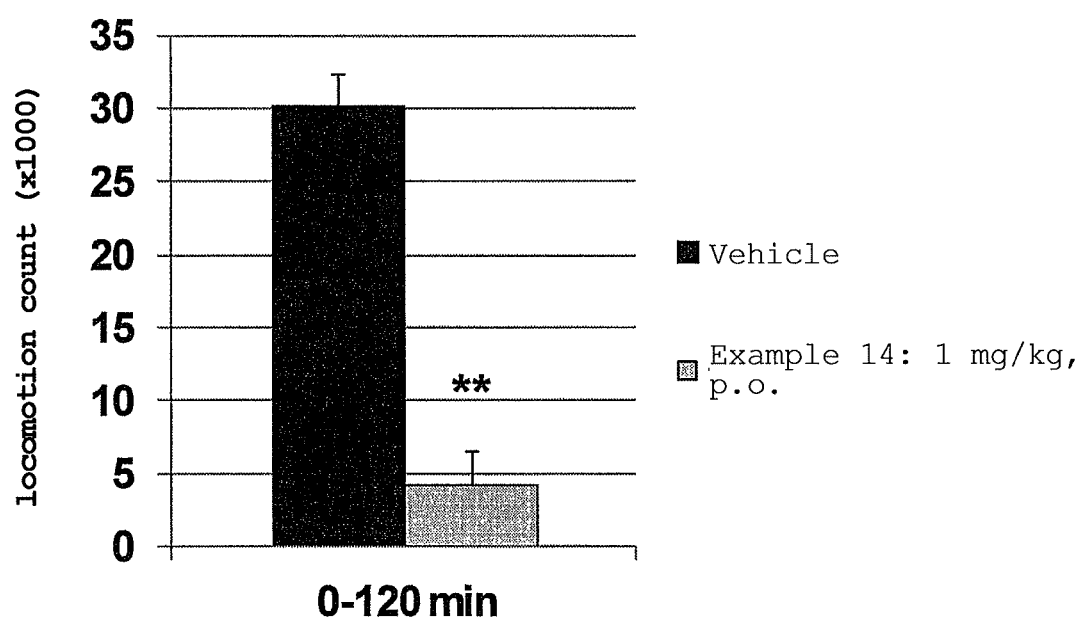
** P ≤ 0.01 (Student's t-test)

CONDENSED HETEROCYCLIC COMPOUND

TECHNICAL FIELD

The present invention relates to a fused heterocyclic compound, which has a superior phosphodiesterase 10A inhibitory action, and is useful as an agent for the treatment or prophylaxis of schizophrenia etc., and the like.

BACKGROUND OF THE INVENTION

Phosphodiesterases (PDEs) are a superfamily of enzymes encoded by 21 genes and subdivided into 11 distinct families according to structural and functional properties. These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

The cAMP and cGMP are involved in the regulation of every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have important role in the regulation of synaptic transmission as well as in neuronal differentiation and survival (non-patent document 1). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenyl and guanyl cyclases in response to extracellular signaling and their degradation by PDEs (non-patent document 2). PDEs provide the only means of degrading the cyclic nucleotides cAMP and cGMP in cells, thus PDEs play an essential role in cyclic nucleotide signal transduction. Thereby, PDEs could be promising targets for various therapeutic drugs.

Phosphodiesterase 10A (PDE10A) was discovered in 1999 (non-patent documents 3-5). Expression studies have shown that PDE10A has the most restricted distribution within the all known PDE families, and the PDE10A mRNA is highly expressed only in brain and testes (non-patent documents 6 and 7). In the brain, mRNA and protein of PDE10A are highly enriched in medium spiny neurons (MSNs) of the striatum (non-patent documents 8 and 9). MSNs are classified into two groups: the MSN that express $D_1$ dopamine receptors responsible for a direct (striatonigral) pathway and the MSN that express $D_2$ dopamine receptors responsible for an indirect (striatopallidal) pathway. The function of direct pathway is to plan and execution, while indirect pathway is to act as a brake on behavioral activation. As PDE10A is expressed in both MSNs, PDE10A inhibitors could activate both of these pathways. The antipsychotic efficacy of current medications, $D_2$ or $D_2/5\text{-HT}_{2A}$ antagonists, mainly derives from their activation of the indirect pathway in the striatum. As PDE10A inhibitors are able to activate this pathway, this suggests that PDE10A inhibitors are promising as antipsychotic drugs. The excessive $D_2$ receptor antagonism in the brain by $D_2$ antagonists causes problems of extrapyramidal side effects and hyperprolactinaemia. However the expression of PDE10A is limited to these striatal pathways in the brain, thus side effects by PDE10A inhibitors were expected to be weaker compared with current $D_2$ antagonists. Regarding the problems of hyperprolactinaemia, PDE10A inhibitors would produce no prolactin elevation due to lack of $D_2$ receptor antagonism in the pituitary. Moreover, the presence of PDE10A in a direct pathway makes it likely that PDE10A inhibitors will have some advantage over current $D_2$ antagonists; the direct pathway is thought to promote desired action, and activation of this pathway by PDE10A inhibitors may counteract extrapyramidal symptoms induced by excessive $D_2$ receptor antagonism. In addition, activation of this pathway could facilitate striatal-thalamic outflow, promoting the execution of procedural strategies. Furthermore, enhancement of second messenger levels without blockade of dopamine and/or other neurotransmitter receptors may also provide therapeutic advantages with fewer adverse side-effects compared with current antipsychotics (e.g., hyperprolactinaemia and weight gain). This unique distribution and function in the brain indicates that PDE10A represents an important new target for the treatment of neurological and psychiatric disorders, in particular psychotic disorders like schizophrenia.

Patent document 1 describes, as a phosphodiesterase (PDE) 10 inhibitor, a compound represented by the formula:

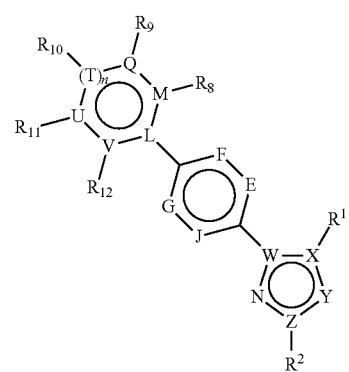

wherein each symbol is as defined in patent document 1, and the following compounds:

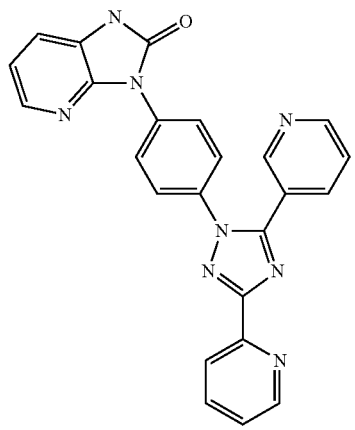

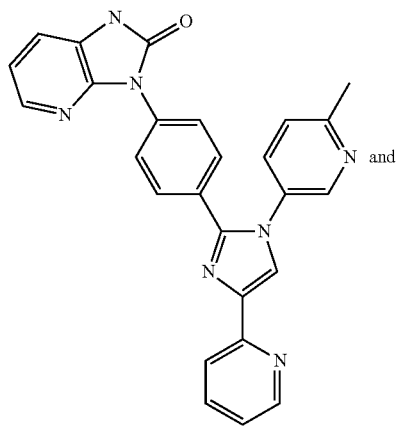

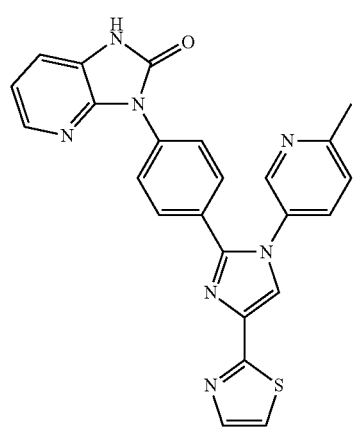

Patent document 2 describes, as a phosphodiesterase (PDE) 10 inhibitor, a compound represented by the formula:

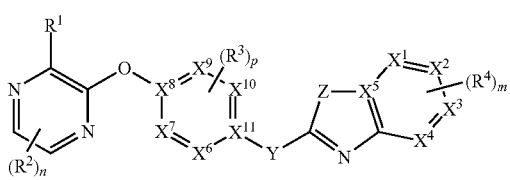

wherein each symbol is as defined in patent document 2, and the following compounds:

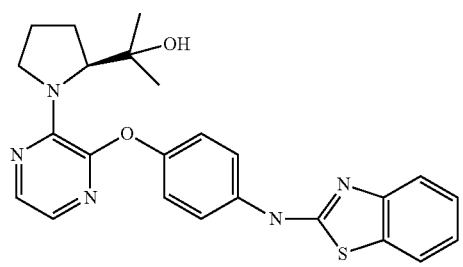

and

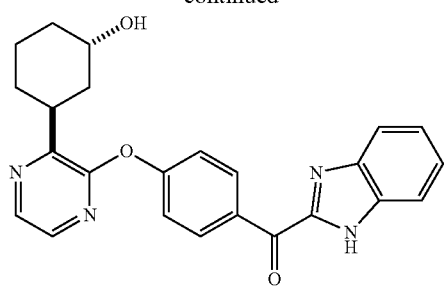

Patent document 3 describes, as a phosphodiesterase (PDE) 10 inhibitor, a compound represented by the formula:

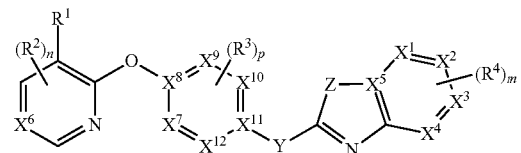

wherein each symbol is as defined in patent document 3, and the following compounds:

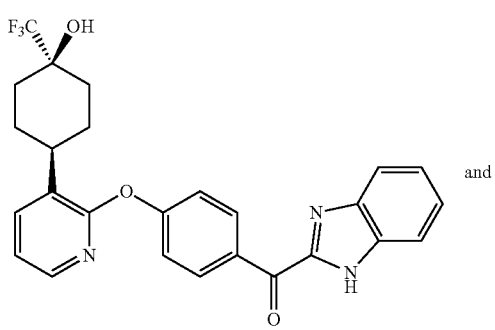

and

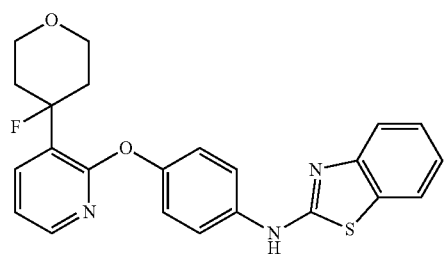

Patent document 4 describes, as a phosphodiesterase (PDE) 10 inhibitor, a compound represented by the formula:

I

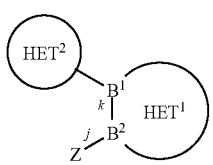

wherein Z is

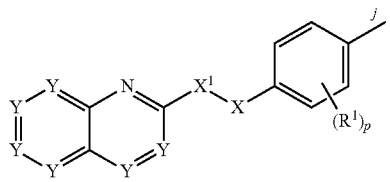

wherein each symbol is as defined in patent document 4.

Patent document 5 describes, as a phosphodiesterase (PDE) 10 inhibitor, a compound represented by the formula:

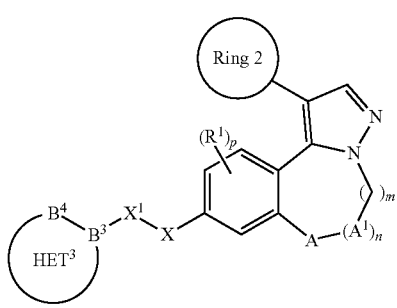

(I)

wherein each symbol is as defined in patent document 5.

Patent document 6 describes, as a phosphodiesterase (PDE) 10 inhibitor, a compound represented by the formula:

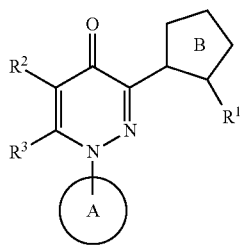

wherein each symbol is as defined in patent document 6.

DOCUMENT LIST

Patent Documents patent document 1: WO2008/004117
patent document 2: WO2010/057121
patent document 3: WO2010/057126
patent document 4: WO2006/072828
patent document 5: WO2008/001182
patent document 6: WO2010/090737

Non-Patent Documents non-patent document 1: Nat. Rev. Drug Discov. 2006, vol. 5, p. 660-670
non-patent document 2: Circ. Res. 2007, vol. 100(7), p. 950-966
non-patent document 3: Proc. Natl. Acad. Sci. USA, 1999, vol. 96, p. 8991-8996
non-patent document 4: J. Biol. Chem. 1999, vol. 274, p. 18438-18445
non-patent document 5: Gene, 1999, vol. 234, p. 109-117
non-patent document 6: Eur. J. Biochem. 1999, vol. 266, p. 1118-1127
non-patent document 7: J. Biol. Chem. 1999, vol. 274, p. 18438-18445
non-patent document 8: Eur. J. Biochem. 1999, vol. 266, p. 1118-1127
non-patent document 9: Brain Res. 2003, vol. 985, p. 113-126

SUMMARY OF THE INVENTION

Problems to be Solved by the Invention

The development of a compound having a superior PDE10A inhibitory action, which is useful as an agent for the treatment or prophylaxis of schizophrenia etc. and the like, and has superior properties in terms of efficacy, low toxicity, stability, in vivo kinetics and the like, has been desired.

The present invention aims to provide a fused heterocyclic compound having a PDE10A inhibitory action, which has a chemical structure different from those of known compounds (including the aforementioned compounds), and a prophylactic or therapeutic drug for diseases such as schizophrenia and the like, which contains the fused heterocyclic compound.

Means of Solving the Problems

The present inventors have conducted intensive studies in an attempt to solve the aforementioned problems and found that compounds represented by the following formula (I) [including compounds represented by the following formulas (I-i), (I-ii) and formula (I-iii)] or salts thereof have superior PDE10A inhibitory action, and made extensive studies to complete the present invention.

Accordingly, the present invention relates to
[1'] a compound represented by the formula (I):

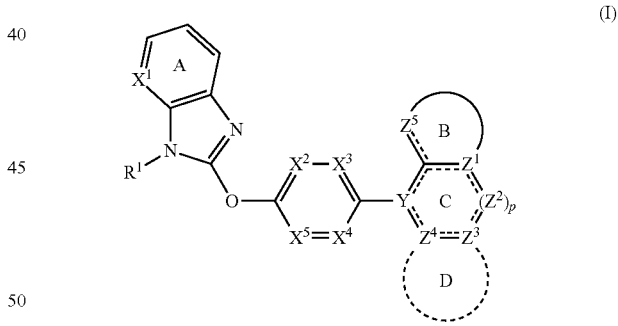

(I)

wherein
$R^1$ is a hydrogen atom or an optionally substituted $C_{1-6}$ alkyl group,
$X^1$ is CH or a nitrogen atom,
ring A optionally has a substituent,
$X^2$ is $CR^2$ or a nitrogen atom,
$X^3$ is $CR^3$ or a nitrogen atom,
$X^4$ is $CR^4$ or a nitrogen atom,
$X^5$ is $CR^5$ or a nitrogen atom,
$R^2$, $R^3$, $R^4$ and $R^5$ are each independently a hydrogen atom or a substituent,
ring B is an optionally substituted 5- or 6-membered nitrogen-containing heterocycle (said nitrogen-containing heterocycle optionally further form a fused ring with a ring other than ring C), $Z^5$ is =N— or —N=, ring C is an optionally substituted 5- or 6-membered ring, Y is a ring C-constituting atom selected from a carbon atom and a nitrogen atom, $Z^1$ is a ring C-constituting atom selected from a carbon atom and a nitrogen atom, $Z^2$, $Z^3$ and $Z^4$ are each independently a ring C-constituting atom selected from a carbon atom, a nitrogen atom, a sulfur atom and an oxygen atom, or $Z^3$ and $Z^4$ are optionally joined to form ring D, ring D is an optionally substituted 5- or 6-membered ring, p is 0 or 1, and

----- is a single bond or a double bond, provided that when p is 0, then the bond between Y and $Z^4$ is a single bond, or a salt thereof;

[1] a compound represented by the formula (I-i):

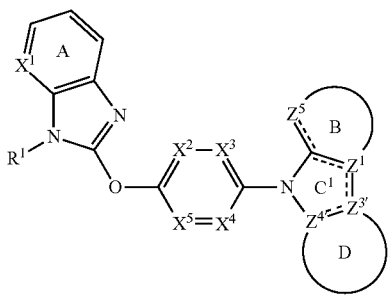

(I-i)

wherein $R^1$ is a hydrogen atom or an optionally substituted $C_{1-6}$ alkyl group, $X^1$ is CH or a nitrogen atom, ring A optionally has a substituent, $X^2$ is $CR^2$ or a nitrogen atom, $X^3$ is $CR^3$ or a nitrogen atom, $X^4$ is $CR^4$ or a nitrogen atom, $X^5$ is $CR^5$ or a nitrogen atom, $R^2$, $R^3$, $R^4$ and $R^5$ are each independently a hydrogen atom or a substituent, ring B is an optionally substituted 5- or 6-membered nitrogen-containing heterocycle (said nitrogen-containing heterocycle optionally further forms a fused ring with a ring other than ring $C^1$), $Z^5$ is =N— or —N=, ring $C^1$ is an optionally substituted 5-membered ring, $Z^1$, $Z^{3\prime}$ and $Z^{4\prime}$ are each independently a ring $C^1$-constituting atom selected from a carbon atom and a nitrogen atom, ring D is an optionally substituted 5- or 6-membered ring, and

----- is a single bond or a double bond, or a salt thereof;

[2] a compound represented by the formula (I-ii):

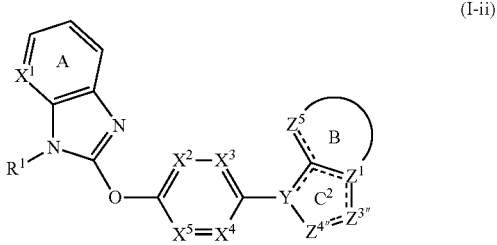

(I-ii)

wherein $R^1$ is a hydrogen atom or an optionally substituted $C_{1-6}$ alkyl group, $X^1$ is CH or a nitrogen atom, ring A optionally has a substituent, $X^2$ is $CR^2$ or a nitrogen atom, $X^3$ is $CR^3$ or a nitrogen atom, $X^4$ is $CR^4$ or a nitrogen atom, $X^5$ is $CR^5$ or a nitrogen atom, $R^2$, $R^3$, $R^4$ and $R^5$ are each independently a hydrogen atom or a substituent, ring B is an optionally substituted 5- or 6-membered nitrogen-containing heterocycle (said nitrogen-containing heterocycle optionally further forms a fused ring with a ring other than ring $C^2$), $Z^5$ is =N— or —N=, ring $C^2$ is an optionally substituted 5-membered ring, Y is a ring $C^2$-constituting atom selected from a carbon atom and a nitrogen atom, $Z^1$ is a ring $C^2$-constituting atom selected from a carbon atom and a nitrogen atom, $Z^{3\prime\prime}$ is a ring $C^2$-constituting atom selected from a carbon atom, a nitrogen atom, a sulfur atom and an oxygen atom, $Z^{4\prime\prime}$ is —O—, —S—, —N=, —$NR^{6\prime}$—, —$CR^{7\prime}$=, —SO—, —$SO_2$— or an optionally substituted methylene group (excluding a carbonyl group), $R^{6\prime}$ and $R^{7\prime}$ are each independently a hydrogen atom or a substituent, and

----- is a single bond or a double bond, or a salt thereof;

[3] a compound represented by the formula (I-iii):

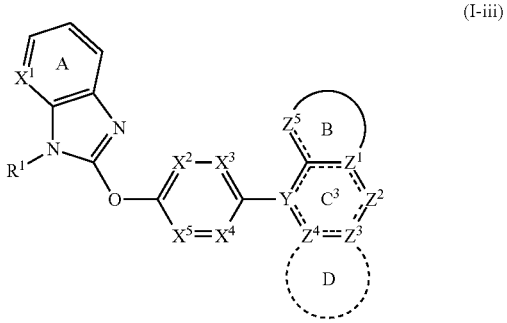

(I-iii)

wherein $R^1$ is a hydrogen atom or an optionally substituted $C_{1-6}$ alkyl group, $X^1$ is CH or a nitrogen atom, ring A optionally has a substituent, $X^2$ is $CR^2$ or a nitrogen atom,
$X^3$ is $CR^3$ or a nitrogen atom,
$X^4$ is $CR^4$ or a nitrogen atom,
$X^5$ is $CR^5$ or a nitrogen atom,
$R^2$, $R^3$, $R^4$ and $R^5$ are each independently a hydrogen atom or a substituent,
ring B is an optionally substituted, 5- or 6-membered nitrogen-containing heterocycle (said nitrogen-containing heterocycle optionally further forms a fused ring with a ring other than ring $C^3$),
$Z^5$ is =N— or —N=,
ring $C^3$ is an optionally substituted 6-membered ring,
Y is a ring $C^3$-constituting atom selected from a carbon atom and a nitrogen atom,
$Z^1$ is a ring $C^3$-constituting atom selected from a carbon atom and a nitrogen atom,
$Z^2$, $Z^3$ and $Z^4$ are each independently a ring $C^3$-constituting atom selected from a carbon atom, a nitrogen atom, a sulfur atom and an oxygen atom, and

------ is a single bond or a double bond,
or $Z^3$ and $Z^4$ are optionally joined to form ring D, and
ring D is an optionally substituted 5- or 6-membered ring, or a salt thereof;
[4] the compound of the above-mentioned [2], wherein $Z^{4'''}$ is —O—, —S—, —N=, —$NR^{6t}$—, —$CR^{7t}$=, —SO—, —$SO_2$— or —$CR^8R^9$— ($R^8$ and $R^9$ are each independently a hydrogen atom or a substituent), or a salt thereof;
[5] the compound of any one of the above-mentioned [1] to [3], wherein $X^2$, $X^3$, $X^4$ and $X^5$ are each CH, or a salt thereof;
[6] the compound of the above-mentioned [1], wherein the compound of the formula (I-i) is a compound represented by the formula (I-i)':

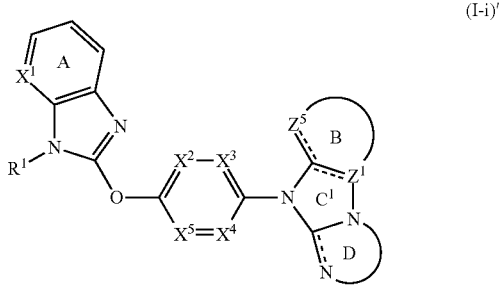

(I-i)' wherein each symbol is as defined in the above-mentioned [1], or a salt thereof;
[7] 9-(4-{[3-(2-methoxyethyl)-3H-imidazo[4,5-b]pyridin-2-yl]oxy}phenyl)-9H-imidazo[1',2':1,2]imidazo[4,5-b]pyridine or a salt thereof;
[8] 5-methyl-9-{4-[(3-methyl-3H-imidazo[4,5-b]pyridin-2-yl)oxy]phenyl}-9H-imidazo[1',2':1,2]imidazo[4,5-b]pyridine or a salt thereof;
[9] a medicament comprising a compound of any one of the above-mentioned [1] to [3], or a salt thereof;
[10] the medicament of the above-mentioned [9], which is a phosphodiesterase 10A inhibitor;
[11] the medicament of the aforementioned [9], which is an agent for the prophylaxis or treatment of schizophrenia;
[12] a method for the prophylaxis or treatment of schizophrenia in a mammal, comprising administering an effective amount of a compound of any one of the above-mentioned [1] to [3], or a salt thereof, to the mammal;
[13] use of a compound of any one of the above-mentioned [1] to [3], or a salt thereof, for the manufacture of a prophylactic or therapeutic drug for schizophrenia;
[14] a compound of any one of the above-mentioned [1] to [3], or a salt thereof, for the use in the prevention or treatment of schizophrenia;
and the like.

Effect of the Invention

The compound represented by the formula (I) (hereinafter sometimes to be referred to as compound (I)) or a salt thereof has a PDE10A inhibitory action, and is useful as a prophylactic or therapeutic drug for schizophrenia and the like. In addition, compound (I) or a salt thereof characteristically shows a superior PDE10A inhibitory action, low phototoxicity, superior metabolic stability, and high solubility.

Compound (I) has the above-mentioned structure wherein a 6-membered ring having $X^2$—$X^5$ is bonded at the para-position to an oxygen atom and fused rings B, C (D), which enables an interaction of ring B-constituting atom $Z^5$, =N— on an imidazole ring to be fused with ring A and the like with an amino acid residue of PDE10A protein, and selective inhibition of PDE10A.

BRIEF DESCRIPTION OF THE DRAWINGS

FIG. 1 shows a suppressive action on hyperlocomotion induced by MK-801 in rat in Example 14.

DESCRIPTION OF EMBODIMENTS

Detailed Description of the Invention

The present invention is explained in detail in the following.

In the present specification, unless otherwise specified, examples of the "halogen atom" include a fluorine atom, a chlorine atom, a bromine atom and an iodine atom.

In the present specification, unless otherwise specified, examples of the "$C_{1-6}$ alkyl (group)" include methyl, ethyl, propyl, isopropyl, butyl, isobutyl, sec-butyl, tert-butyl, pentyl, isopentyl, neopentyl, hexyl and the like.

In the present specification, unless otherwise specified, examples of the "$C_{2-6}$ alkenyl (group)" include vinyl, 1-propen-1-yl, 2-propen-1-yl, isopropenyl, 2-buten-1-yl, 4-penten-1-yl, 5-hexen-1-yl and the like.

Examples of the "$C_{2-6}$ alkynyl (group)" include ethynyl, 1-propyn-1-yl, 2-propyn-1-yl, 4-pentyn-1-yl, 5-hexyn-1-yl and the like.

In the present specification, unless otherwise specified, examples of the "$C_{3-7}$ cycloalkyl (group)" include cyclopropyl, cyclobutyl, cyclopentyl, cyclohexyl, cycloheptyl and the like.

In the present specification, unless otherwise specified, examples of the "$C_{6-14}$ aryl (group)" include phenyl, 1-naphthyl, 2-naphthyl, 2-biphenylyl, 3-biphenylyl, 4-biphenylyl, 2-anthryl and the like.

In the present specification, unless otherwise specified, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

In the present specification, unless otherwise specified, "$C_{6-14}$ aryl-$C_{2-6}$ alkenyl (group)" means the above-mentioned "$C_{2-6}$ alkenyl (group)" substituted by the above-mentioned "$C_{6-14}$ aryl (group)" and, for example, styryl and the like can be mentioned.

In the present specification, unless otherwise specified, examples of the "carbocycle having 5 or 6 carbon atoms" include a $C_{5-6}$ cycloalkane (e.g., cyclopentane, cyclohexane), a $C_{5-6}$ cycloalkene (e.g., cyclopentene, cyclohexene), a $C_{5-6}$ cycloalkadiene (e.g., cyclopentadiene, cyclohexadiene), benzene, and the like.

In the present specification, unless otherwise specified, examples of the "$C_{3-6}$ cycloalkane" include cyclopropane, cyclobutane, cyclopentane, cyclohexane and the like.

In the present specification, unless otherwise specified, examples of the "5- or 6-membered heterocycle" include a 5- or 6-membered heterocycle containing, besides carbon atoms, 1 to 4 hetero atoms selected from a nitrogen atom, a sulfur atom and an oxygen atom.

In the present specification, unless otherwise specified, examples of the "5- or 6-membered heterocycle containing, besides carbon atoms, 1 to 4 hetero atoms selected from a nitrogen atom, a sulfur atom and an oxygen atom" include pyrrolidine, tetrahydrofuran, tetrahydrothiophene, piperidine, tetrahydropyran, morpholine, thiomorpholine, piperazine, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like.

In the present specification, unless otherwise specified, the "heterocyclic group" (and heterocyclic moiety in the substituent) include(s) a non-aromatic heterocyclic group and an aromatic heterocyclic group, and examples thereof include a 3- to 14-membered heterocyclic group containing 1 to 5 hetero atoms selected from a nitrogen atom, a sulfur atom and an oxygen atom, and the like. The "heterocyclic group" can be monocyclic, bicyclic or tricyclic.

In the present specification, unless otherwise specified, examples of the "3- to 14-membered heterocyclic group" include 3- to 14-membered aromatic heterocyclic groups containing 1 to 5 hetero atoms selected from a nitrogen atom, a sulfur atom and an oxygen atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 5-phthalazinyl, 6-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 5-quinoxalinyl, 6-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl) and the like; and 3- to 14-membered saturated or partially unsaturated non-aromatic heterocyclic groups containing 1 to 5 hetero atoms selected from a nitrogen atom, a sulfur atom and an oxygen atom, such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidyl (e.g., 1-piperidyl, 2-piperidyl, 3-piperidyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), azonanyl (e.g., 1-azonanyl, 2-azonanyl, 3-azonanyl, 4-azonanyl, 5-azonanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, dihydroisoquinolyl (e.g., 3,4-dihydroisoquinolin-2-yl) and the like.

In the present specification, unless otherwise specified, examples of the "5- to 7-membered heterocyclic group containing 1 to 4 hetero atoms selected from a nitrogen atom, a sulfur atom, and an oxygen atom" include a "5- to 7-membered heterocyclic group containing 1 to 4 hetero atoms selected from a nitrogen atom, a sulfur atom, and an oxygen atom" from the "3- to 14-membered heterocyclic group containing 1 to 5 hetero atoms selected from a nitrogen atom, a sulfur atom and an oxygen atom" exemplified for the above-mentioned "heterocyclic group".

In the present specification, unless otherwise specified, examples of the "5- or 6-membered ring" include benzene, "5- or 6-membered non-aromatic hydrocarbon ring", "5- or 6-membered aromatic heterocycle", and "5- or 6-membered non-aromatic heterocycle".

Here, as the "5- or 6-membered non-aromatic hydrocarbon ring", cyclopentane, cyclohexane, cyclopentene, cyclohexene, 1,3-cyclopentadiene, 1,3-cyclohexadiene, 1,4-cyclohexadiene, cyclopentyne, cyclohexyne and the like can be mentioned.

Examples of the "5- or 6-membered aromatic heterocycle" here include a 5- or 6-membered monocyclic aromatic heterocycle containing, as a ring-constituting atom besides carbon atom, 1 to 4 hetero atoms selected from an oxygen atom, a sulfur atom (said sulfur atom may be oxidized) and a nitrogen atom.

Preferable examples of such 5- or 6-membered monocyclic aromatic heterocycle include furan, thiophene, pyridine, pyrimidine, pyridazine, pyrazine, pyrrole, imidazole, pyrazole, triazole, isothiazole, oxazole, isoxazole, oxadiazole (e.g., 1,2,5-oxadiazole, 1,3,4-oxadiazole), thiadiazole (e.g., 1,2,3-thiadiazole, 1,3,4-thiadiazole), triazole (e.g., 1,2,4-triazole, 1,2,3-triazole), tetrazole, triazine (e.g., 1,2,4-triazine) and the like.

Examples of the 5- or 6-membered non-aromatic heterocycle here include a 5- or 6-membered monocyclic non-aromatic heterocycle containing, as a ring-constituting atom besides carbon atom, 1 to 4 hetero atoms selected from an oxygen atom, a sulfur atom (said sulfur atom may be oxidized) and a nitrogen atom.

Preferable examples of such 5- or 6-membered monocyclic non-aromatic heterocycle include pyrrolidine, piperidine, homopiperidine, tetrahydropyridine (e.g., 1,2,3,6-tetrahydropyridine), dihydropyridine; e.g., 1,2-dihydropyridine, 2,3-dihydropyridine), morpholine, thiomorpholine, 1,1-dioxidethiomorpholine, piperazine, oxazolidine, thiazolidine, imidazolidine, 2-oxoimidazolidine, oxazoline, thiazoline, imidazoline, dioxole (e.g., 1,3-dioxole), dioxolane (e.g., 1,3-dioxolane), dihydrooxadiazole (e.g., 4,5-dihydro-1,2,4-oxadiazole), pyran, tetrahydropyran, thiopyran, tetrahydrothiopyran, tetrahydrofuran, pyrazolidine, pyrazoline, tetrahydropyrimidine, dihydrotriazole (e.g., 2,3-dihydro-1H-1,2,3-triazole), tetrahydrotriazole (e.g., 2,3,4,5-tetrahydro-1H-1,2,3-triazole), dihydrooxadiazole (e.g., 4,5-dihydro-1,2,4-oxadiazole), thiazine (e.g., 1,4-thiazine), dihydropyridazine (e.g., 1,6-dihydropyridazine), tetrahydropyridazine (e.g., 1,4,5,6-tetrahydropyridazine), dihydrothioxazine (e.g., 2,3-dihydro-1,4-thioxazine), dihydrothiazine (e.g., 3,4-dihydro-2H-1,4-thiazine) and the like.

In the present specification, unless otherwise specified, examples of the "5-membered ring" include 5-membered ones from the aforementioned "5- or 6-membered ring".

In the present specification, unless otherwise specified, examples of the "6-membered ring" include 6-membered ones from the aforementioned "5- or 6-membered ring".

In the present specification, unless otherwise specified, examples of the "$C_{1-6}$ alkoxy (group)" include methoxy, ethoxy, propoxy, isopropoxy, butoxy, isobutoxy, sec-butoxy, tert-butoxy, pentyloxy, hexyloxy and the like.

In the present specification, unless otherwise specified, examples of the "$C_{3-7}$ cycloalkyloxy (group)" include cyclopropyloxy, cyclobutyloxy, cyclopentyloxy, cyclohexyloxy and the like.

In the present specification, unless otherwise specified, examples of the "$C_{6-14}$ aryloxy (group)" include phenyloxy, 1-naphthyloxy, 2-naphthyloxy and the like.

In the present specification, unless otherwise specified, examples of the "$C_{7-16}$ aralkyloxy (group)" include benzyloxy, phenethyloxy and the like.

In the present specification, unless otherwise specified, examples of the heterocyclic moiety of the "heterocyclyl-oxy (group)" include those similar to the aforementioned "heterocyclic group". Specific examples of the "heterocyclyl-oxy (group)" include a 3- to 14-membered heterocyclyl-oxy (group) containing 1 to 5 hetero atoms selected from a nitrogen atom, a sulfur atom and an oxygen atom, and the like.

In the present specification, unless otherwise specified, examples of the aromatic heterocyclic moiety of the "aromatic heterocyclyl-oxy (group)" include those similar to the "aromatic heterocyclic group" exemplified as the aforementioned "heterocyclic group". Specific examples of the "aromatic heterocyclyl-oxy (group)" include a 3- to 14-membered aromatic heterocyclyl-oxy (group) containing 1 to 5 hetero atoms selected from a nitrogen atom, a sulfur atom and an oxygen atom, and the like.

In the present specification, unless otherwise specified, examples of the "$C_{1-6}$ alkyl-carbonyloxy (group)" include acetoxy, propionyloxy and the like.

In the present specification, unless otherwise specified, examples of the "$C_{1-6}$ alkoxy-carbonyloxy (group)" include methoxycarbonyloxy, ethoxycarbonyloxy, propoxycarbonyloxy, butoxycarbonyloxy and the like.

In the present specification, unless otherwise specified, examples of the "$C_{3-7}$ cycloalkyl-carbonyloxy (group)" include cyclopropylcarbonyloxy, cyclobutylcarbonyloxy, cyclopentylcarbonyloxy, cyclohexylcarbonyloxy and the like.

In the present specification, unless otherwise specified, examples of the "$C_{6-14}$ aryl-carbonyloxy (group)" include benzoyloxy, naphthylcarbonyloxy and the like.

In the present specification, unless otherwise specified, examples of the heterocyclic moiety of the "heterocyclyl-carbonyloxy (group)" include those similar to the aforementioned "heterocyclic group". Specific examples of the "heterocyclyl-carbonyloxy (group)" include a 3- to 14-membered heterocyclyl-carbonyloxy (group) containing 1 to 5 hetero atoms selected from a nitrogen atom, a sulfur atom, and an oxygen atom, and the like.

In the present specification, unless otherwise specified, examples of the "mono- or di-$C_{1-6}$ alkyl-carbamoyl (group)" include a mono-$C_{1-6}$ alkyl-carbamoyl (group) such as methylcarbamoyl, ethylcarbamoyl and the like; a di-$C_{1-6}$ alkyl-carbamoyl (group) such as dimethylcarbamoyl, diethylcarbamoyl and the like; and the like.

In the present specification, unless otherwise specified, examples of the "mono- or di-$C_{3-7}$ cycloalkyl-carbamoyl (group)" include cyclopropylcarbamoyl, cyclobutylcarbamoyl, cyclopentylcarbamoyl, cyclohexylcarbamoyl and the like.

In the present specification, unless otherwise specified, examples of the "mono- or di-$C_{6-14}$ aryl-carbamoyl (group)" include phenylcarbamoyl, naphthylcarbamoyl and the like.

In the present specification, unless otherwise specified, examples of the heterocycle moiety of the "heterocyclyl-carbamoyl (group)" include those similar to the aforementioned "heterocyclic group". Specific examples of the "heterocyclyl-carbamoyl (group)" include a 3- to 14-membered heterocyclyl-carbamoyl (group) containing 1 to 5 hetero atoms selected from a nitrogen atom, a sulfur atom, and an oxygen atom and the like.

In the present specification, unless otherwise specified, examples of the "mono- or di-$C_{1-6}$ alkyl-carbamoyloxy (group)" include a mono-$C_{1-6}$ alkyl-carbamoyloxy (group) such as methylcarbamoyloxy, ethylcarbamoyloxy and the like; a di-$C_{1-6}$ alkyl-carbamoyloxy (group) such as dimethylcarbamoyloxy, diethylcarbamoyloxy and the like; and the like.

In the present specification, unless otherwise specified, examples of the "mono- or di-$C_{6-14}$ aryl-carbamoyloxy (group)" include phenylcarbamoyloxy, naphthylcarbamoyloxy and the like.

In the present specification, unless otherwise specified, examples of the "$C_{1-6}$ alkylsulfonyloxy group" include methylsulfonyloxy, ethylsulfonyloxy and the like.

In the present specification, unless otherwise specified, examples of the "$C_{1-6}$ alkylsulfanyl (group)" include methylsulfanyl, ethylsulfanyl, propylsulfanyl, isopropylsulfanyl, butylsulfanyl, sec-butylsulfanyl, tert-butylsulfanyl and the like.

In the present specification, unless otherwise specified, examples of the "$C_{3-7}$ cycloalkylsulfanyl (group)" include cyclopropylsulfanyl, cyclobutylsulfanyl, cyclopentylsulfanyl, cyclohexylsulfanyl and the like.

In the present specification, unless otherwise specified, examples of the "$C_{6-14}$ arylsulfanyl (group)" include phenylsulfanyl, 1-naphthylsulfanyl, 2-naphthylsulfanyl and the like.

In the present specification, unless otherwise specified, examples of the "$C_{7-16}$ aralkylsulfanyl (group)" include benzylsulfanyl, phenethylsulfanyl and the like.

In the present specification, unless otherwise specified, examples of the heterocyclic moiety of the "heterocyclylsulfanyl (group)" include those similar to the aforementioned "heterocyclic group". Specific examples of the "heterocyclylsulfanyl (group)" include a 3- to 14-membered heterocyclylsulfanyl (group) containing 1 to 5 hetero atoms selected from a nitrogen atom, a sulfur atom and an oxygen atom.

In the present specification, unless otherwise specified, examples of the "$C_{1-6}$ alkyl-carbonyl (group)" include acetyl, propionyl, pivaloyl and the like.

In the present specification, unless otherwise specified, examples of the "$C_{3-7}$ cycloalkyl-carbonyl (group)" include cyclopropylcarbonyl, cyclopentylcarbonyl, cyclohexylcarbonyl and the like.

In the present specification, unless otherwise specified, examples of the "$C_{6-14}$ aryl-carbonyl (group)" include benzoyl, 1-naphthoyl, 2-naphthoyl and the like.

In the present specification, unless otherwise specified, examples of the "$C_{7-16}$ aralkyl-carbonyl (group)" include phenylacetyl, 3-phenylpropionyl and the like.

In the present specification, unless otherwise specified, examples of the heterocyclic moiety of the "heterocyclylcarbonyl (group)" include those similar to the above-mentioned "heterocyclic group". Specific examples thereof include a 3- to 14-membered heterocyclyl-carbonyl (group) containing 1 to 5 hetero atoms selected from a nitrogen atom, a sulfur atom and an oxygen atom. More specific examples thereof include picolinoyl, nicotinoyl, isonicotinoyl, 2-thenoyl, 3-thenoyl, 2-furoyl, 3-furoyl, 4-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl, 1,5-diazocan-3-ylcarbonyl and the like.

In the present specification, unless otherwise specified, examples of the "$C_{1-6}$ alkylsulfonyl (group)" include methylsulfonyl, ethylsulfonyl and the like.

In the present specification, unless otherwise specified, examples of the "$C_{3-7}$ cycloalkylsulfonyl (group)" include cyclopropylsulfonyl, cyclobutylsulfonyl, cyclopentylsulfonyl, cyclohexylsulfonyl and the like.

In the present specification, unless otherwise specified, examples of the "$C_{6-14}$ arylsulfonyl (group)" include phenylsulfonyl, 1-naphthylsulfonyl, 2-naphthylsulfonyl and the like.

In the present specification, unless otherwise specified, examples of the heterocyclic moiety of the "heterocyclylsulfonyl (group)" include those similar to the aforementioned "heterocyclic group". Specific examples of the "heterocyclylsulfonyl (group)" include a 3- to 14-membered heterocyclylsulfonyl (group) containing 1 to 5 hetero atoms selected from a nitrogen atom, a sulfur atom and an oxygen atom.

In the present specification, unless otherwise specified, examples of the "$C_{1-6}$ alkylsulfinyl (group)" include methylsulfinyl, ethylsulfinyl and the like.

In the present specification, unless otherwise specified, examples of the "$C_{3-7}$ cycloalkylsulfinyl (group)" include cyclopropylsulfinyl, cyclobutylsulfinyl, cyclopentylsulfinyl, cyclohexylsulfinyl and the like.

In the present specification, unless otherwise specified, examples of the "$C_{6-14}$ arylsulfinyl (group)" include phenylsulfinyl, 1-naphthylsulfinyl, 2-naphthylsulfinyl and the like.

In the present specification, unless otherwise specified, examples of the heterocyclic moiety of the "heterocyclylsulfinyl (group)" include those similar to the aforementioned "heterocyclic group". Specific examples of the "heterocyclylsulfinyl (group)" include a 3- to 14-membered heterocyclylsulfinyl (group) containing 1 to 5 hetero atoms selected from a nitrogen atom, a sulfur atom and an oxygen atom.

In the present specification, unless otherwise specified, examples of the "mono- or di-$C_{1-6}$ alkyl-amino (group)" include a mono-$C_{1-6}$ alkyl-amino (group) such as methylamino, ethylamino, propylamino and the like; a di-$C_{1-6}$ alkyl-amino (group) such as dimethylamino, diethylamino and the like; and the like.

In the present specification, unless otherwise specified, examples of the "mono- or di-$C_{3-7}$ cycloalkyl-amino (group)" include cyclopropylamino, cyclopentylamino, cyclohexylamino and the like.

In the present specification, unless otherwise specified, examples of the "mono- or di-$C_{6-14}$ aryl-amino (group)" include phenylamino, diphenylamino and the like.

In the present specification, unless otherwise specified, examples of the "mono- or di-$C_{7-16}$ aralkyl-amino (group)" include benzylamino and the like.

In the present specification, unless otherwise specified, examples of the heterocycle moiety of the "mono- or di-heterocyclyl-amino (group)" include those similar to the above-mentioned "heterocyclic group". Specifically, a "3- to 14-membered heterocyclyl-amino (group) containing 1 to 5 hetero atoms selected from a nitrogen atom, a sulfur atom and an oxygen atom" can be mentioned and, more specifically, for example, (pyridyl-2-yl)amino and the like can be mentioned.

In the present specification, unless otherwise specified, examples of the "mono- or di-($C_{1-6}$ alkyl-carbonyl)amino (group)" include acetylamino, propionylamino, pivaloylamino and the like.

In the present specification, unless otherwise specified, examples of the "mono- or di-($C_{3-7}$ cycloalkyl-carbonyl)amino (group)" include cyclopropylcarbonylamino, cyclopentylcarbonylamino, cyclohexylcarbonylamino and the like.

In the present specification, unless otherwise specified, examples of the "mono- or di-($C_{6-14}$ aryl-carbonyl)amino (group)" include benzoylamino, naphthoylamino and the like.

In the present specification, unless otherwise specified, examples of the heterocycle moiety of the "mono- or di-(heterocyclyl-carbonyl)amino (group)" include those similar to the above-mentioned "heterocyclic group". Specifically, a "mono- or di-(3- to 14-membered heterocyclyl-carbonyl) amino (group) containing 1 to 5 hetero atoms selected from a nitrogen atom, a sulfur atom and an oxygen atom" can be mentioned, more specifically, for example, (pyridyl-2-ylcarbonyl)amino and the like can be mentioned.

In the present specification, unless otherwise specified, examples of the "mono- or di-($C_{1-6}$ alkoxy-carbonyl)amino (group)" include methoxycarbonylamino, ethoxycarbonylamino, propoxycarbonylamino, butoxycarbonylamino and the like.

In the present specification, unless otherwise specified, examples of the "mono- or di-($C_{3-8}$ cycloalkoxy-carbonyl) amino (group)" include cyclopropoxycarbonylamino, cyclopentyloxycarbonylamino, cyclohexyloxycarbonylamino and the like.

In the present specification, unless otherwise specified, examples of the heterocycle moiety of the "mono- or di-(heterocyclyl-oxycarbonyl)amino (group)" include those similar to the above-mentioned "heterocyclic group". Specifically, a "mono- or di-(3- to 14-membered heterocyclyl-oxycarbonyl)amino (group) containing 1 to 5 hetero atoms selected from a nitrogen atom, a sulfur atom and an oxygen atom" can be mentioned, more specifically, for example, (pyridyl-2-yloxycarbonyl)amino and the like can be mentioned.

In the present specification, unless otherwise specified, examples of the "mono- or di-($C_{1-6}$ alkylsulfonyl)amino (group)" include methylsulfonylamino, ethylsulfonylamino and the like.

In the present specification, unless otherwise specified, examples of the "mono- or di-($C_{3-8}$cycloalkylsulfonyl)amino (group)" include cyclopropylsulfonylamino, cyclopentylsulfonylamino, cyclohexylsulfonylamino and the like.

In the present specification, unless otherwise specified, examples of the "mono- or di-($C_{6-14}$ arylsulfonyl)amino (group)" include phenylsulfonylamino, 2-naphthylsulfonylamino, 1-naphthylsulfonylamino and the like.

In the present specification, unless otherwise specified, examples of the "heterocycle (group)" of the "mono- or di-(heterocyclyl-sulfonyl)amino (group)" include those similar to the above-mentioned "heterocyclic group". Specifically, a "mono- or di-(3- to 14-membered heterocyclyl-sulfonyl) amino (group) containing 1 to 5 hetero atoms selected from a nitrogen atom, a sulfur atom and an oxygen atom" can be mentioned, more specifically, for example, (pyridyl-2-ylsulfonyl)amino and the like can be mentioned.

In the present specification, unless otherwise specified, examples of the "$C_{1-6}$ alkoxy-carbonyl (group)" include methoxycarbonyl, ethoxycarbonyl, propoxycarbonyl, tert-butoxycarbonyl and the like.

In the present specification, unless otherwise specified, examples of the "$C_{6-14}$ aryloxy-carbonyl (group)" include phenoxycarbonyl and the like.

In the present specification, unless otherwise specified, examples of the "$C_{7-16}$ aralkyloxy-carbonyl (group)" include benzyloxycarbonyl, phenethyloxycarbonyl and the like.

In the present specification, unless otherwise specified, examples of the "optionally substituted silyloxy-carbonyl (group)" include trimethylsilyloxycarbonyl (TMS-O—CO—), triethylsilyloxycarbonyl (TES-O—CO—), tert-butyldimethylsilyloxycarbonyl (TES-O—CO—), triisopropylsilyloxycarbonyl (TIPS-O—CO—), tert-butyldiphenylsilyloxycarbonyl (TBDPS-O—CO—) and the like.

In the present specification, unless otherwise specified, examples of the heterocycle moiety of the "heterocyclyl-$C_{1-6}$ alkyl (group)" include those similar to the above-mentioned "heterocyclic group". Specifically, a "3- to 14-membered heterocyclyl-$C_{1-6}$ alkyl (group) containing 1 to 5 hetero atoms selected from a nitrogen atom, a sulfur atom and an oxygen atom" can be mentioned.

In the present specification, the "Substituent Group A" consists of
(1) a halogen atom;
(2) a nitro group;
(3) a cyano group;
(4) an optionally substituted $C_{1-6}$ alkyl group;
(5) an optionally substituted $C_{2-6}$ alkenyl group;
(6) an optionally substituted $C_{2-6}$ alkynyl group;
(7) an optionally substituted $C_{3-7}$ cycloalkyl group;
(8) an optionally substituted $C_{6-14}$ aryl group;
(9) an optionally substituted $C_{7-16}$ aralkyl group;
(10) an optionally substituted $C_{6-14}$ aryl-$C_{2-6}$ alkenyl group;
(11) an optionally substituted heterocyclic group;
(12) a hydroxy group;
(13) an optionally substituted $C_{1-6}$ alkoxy group;
(14) an optionally substituted $C_{3-7}$ cycloalkyloxy group;
(15) an optionally substituted $C_{6-14}$ aryloxy group;
(16) an optionally substituted $C_{7-16}$ aralkyloxy group;
(17) an optionally substituted heterocyclyl-oxy group;
(18) an optionally substituted $C_{1-6}$ alkyl-carbonyloxy group;
(19) an optionally substituted $C_{1-6}$ alkoxy-carbonyloxy group;
(20) an optionally substituted $C_{3-7}$ cycloalkyl-carbonyloxy group;
(21) an optionally substituted $C_{6-14}$ aryl-carbonyloxy group;
(22) an optionally substituted heterocyclyl-carbonyloxy group;
(23) an optionally substituted carbamoyl group
[e.g.,
a carbamoyl group,
an optionally substituted mono- or di-$C_{1-6}$ alkyl-carbamoyl group,
an optionally substituted mono- or di-$C_{3-7}$ cycloalkyl-carbamoyl group,
an optionally substituted mono- or di-$C_{6-14}$ aryl-carbamoyl group,
an optionally substituted mono- or di-heterocyclyl-carbamoyl group and the like];
(24) an optionally substituted mono- or di-$C_{1-6}$ alkyl-carbamoyloxy group;
(25) an optionally substituted mono- or di-$C_{6-14}$ aryl-carbamoyloxy group;
(26) an optionally substituted $C_{1-6}$ alkylsulfonyloxy group,
(27) a mercapto group;
(28) an optionally substituted $C_{1-6}$ alkylsulfanyl group;
(29) an optionally substituted $C_{3-7}$ cycloalkylsulfanyl group;
(30) an optionally substituted $C_{6-14}$ arylsulfanyl group;
(31) an optionally substituted $C_{7-16}$ aralkylsulfanyl group;
(32) an optionally substituted heterocyclyl-sulfanyl group;
(33) a formyl group;
(34) an optionally substituted $C_{1-6}$ alkyl-carbonyl group;
(35) an optionally substituted $C_{3-7}$ cycloalkyl-carbonyl group;
(36) an optionally substituted $C_{6-14}$ aryl-carbonyl group;
(37) an optionally substituted $C_{7-16}$ aralkyl-carbonyl group;
(38) an optionally substituted heterocyclyl-carbonyl group;
(39) an optionally substituted $C_{1-6}$ alkylsulfonyl group;
(40) an optionally substituted $C_{3-7}$ cycloalkylsulfonyl group;
(41) an optionally substituted $C_{6-14}$ arylsulfonyl group;
(42) an optionally substituted heterocyclyl-sulfonyl group;

(43) an optionally substituted $C_{1-6}$ alkylsulfinyl group;
(44) an optionally substituted $C_{3-7}$ cycloalkylsulfinyl group;
(45) an optionally substituted $C_{6-14}$ arylsulfinyl group;
(46) an optionally substituted heterocyclyl-sulfinyl group;
(47) a sulfo group;
(48) a sulfamoyl group;
(49) a sulfinamoyl group;
(50) a sulfenamoyl group;
(51) a thiocarbamoyl group;
(52) an optionally substituted amino group
[e.g.,
an amino group,
an optionally substituted mono- or di-$C_{1-6}$ alkyl-amino group,
an optionally substituted mono- or di-$C_{3-7}$ cycloalkyl-amino group,
an optionally substituted mono- or di-$C_{6-14}$ aryl-amino group,
an optionally substituted mono- or di-$C_{7-16}$ aralkyl-amino group,
an optionally substituted mono- or di-heterocyclyl-amino group,
an optionally substituted mono- or di-$C_{6-14}$ aryl-carbonylamino group,
a formylamino group,
an optionally substituted mono- or di-($C_{1-6}$ alkyl-carbonyl)amino group,
an optionally substituted mono- or di-($C_{3-7}$ cycloalkyl-carbonyl)amino group,
an optionally substituted mono- or di-(heterocyclyl-carbonyl)amino group,
an optionally substituted mono- or di-($C_{1-6}$ alkoxy-carbonyl)amino group,
an optionally substituted mono- or di-($C_{3-8}$ cycloalkoxy-carbonyl)amino group,
an optionally substituted mono- or di-(heterocyclyl-oxycarbonyl)amino group,
an optionally substituted mono- or di-($C_{1-6}$ alkylsulfonyl)amino group,
an optionally substituted mono- or di-($C_{3-8}$ cycloalkylsulfonyl)amino group,
an optionally substituted mono- or di-($C_{6-14}$ arylsulfonyl)amino group,
an optionally substituted heterocyclyl-sulfonylamino group and the like];
(53) an optionally substituted $C_{1-6}$ alkoxy-carbonyl group;
(54) an optionally substituted $C_{6-14}$ aryloxy-carbonyl group;
(55) an optionally substituted $C_{7-16}$ aralkyloxy-carbonyl group; and
(56) an optionally substituted silyloxy-carbonyl group.
  As the substituent of the
"optionally substituted $C_{1-6}$ alkyl group",
"optionally substituted $C_{2-6}$ alkenyl group",
"optionally substituted $C_{2-6}$ alkynyl group",
"optionally substituted $C_{1-6}$ alkoxy group",
"optionally substituted $C_{1-6}$ alkyl-carbonyloxy group",
"optionally substituted $C_{1-6}$ alkoxy-carbonyloxy group",
"optionally substituted mono- or di-$C_{1-6}$ alkyl-carbamoyl group",
"optionally substituted mono- or di-$C_{1-6}$ alkyl-carbamoyloxy group",
"optionally substituted $C_{1-6}$ alkylsulfonyloxy group",
"optionally substituted $C_{1-6}$ alkylsulfanyl group",
"optionally substituted $C_{1-6}$ alkyl-carbonyl group",
"optionally substituted $C_{1-6}$ alkylsulfonyl group";
"optionally substituted $C_{1-6}$ alkylsulfinyl group",
"optionally substituted mono- or di-$C_{1-6}$ alkyl-amino group",
"optionally substituted mono- or di-($C_{1-6}$ alkyl-carbonyl) amino group",
"optionally substituted mono- or di-($C_{1-6}$ alkoxy-carbonyl) amino group",
"optionally substituted mono- or di-($C_{1-6}$ alkylsulfonyl) amino group",
"optionally substituted $C_{1-6}$ alkoxy-carbonyl group", and
"optionally substituted silyloxy-carbonyl group" in the Substituent Group A, substituents selected from the following Substituent Group B can be mentioned. The number of the substituents is 1 to the maximum substitutable number, more preferably 1 to 3.
  As the substituent of the
"optionally substituted $C_{3-7}$ cycloalkyl group",
"optionally substituted $C_{6-14}$ aryl group",
"optionally substituted $C_{7-16}$ aralkyl group",
"optionally substituted $C_{6-14}$ aryl-$C_{2-6}$ alkenyl group",
"optionally substituted heterocyclic group",
"optionally substituted $C_{3-7}$ cycloalkyloxy group",
"optionally substituted $C_{6-14}$ aryloxy group",
"optionally substituted $C_{7-16}$ aralkyloxy group",
"optionally substituted heterocyclyl-oxy group",
"optionally substituted $C_{3-7}$ cycloalkyl-carbonyloxy group",
"optionally substituted $C_{6-14}$ aryl-carbonyloxy group",
"optionally substituted heterocyclyl-carbonyloxy group",
"optionally substituted mono- or di-$C_{3-7}$ cycloalkyl-carbamoyl group",
"optionally substituted mono- or di-$C_{6-14}$ aryl-carbamoyl group",
"optionally substituted mono- or di-heterocyclyl-carbamoyl group",
"optionally substituted mono- or di-$C_{6-14}$ aryl-carbamoyloxy group",
"optionally substituted $C_{3-7}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-7}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-7}$ cycloalkylsulfonyl group",
"optionally substituted $C_{6-14}$ arylsulfonyl group",
"optionally substituted heterocyclyl-sulfonyl group",
"optionally substituted $C_{3-7}$ cycloalkylsulfinyl group",
"optionally substituted $C_{6-14}$ arylsulfinyl group",
"optionally substituted heterocyclyl-sulfinyl group",
"optionally substituted mono- or di-$C_{3-7}$ cycloalkyl-amino group",
"optionally substituted mono- or di-$C_{6-14}$ aryl-amino group",
"optionally substituted mono- or di-$C_{7-16}$ aralkyl-amino group",
"optionally substituted mono- or di-heterocyclyl-amino group",
"optionally substituted mono- or di-$C_{6-14}$ aryl-carbonylamino to group",
"optionally substituted mono- or di-($C_{3-7}$ cycloalkyl-carbonyl)amino group",
"optionally substituted mono- or di-(heterocyclyl-carbonyl) amino group",
"optionally substituted mono- or di-($C_{3-8}$ cycloalkoxy-carbonyl)amino group",
"optionally substituted mono- or di-(heterocyclyl-oxycarbonyl)amino group",
"optionally substituted mono- or di-($C_{3-8}$ cycloalkylsulfonyl) amino group", "optionally substituted mono- or di-($C_{6-14}$ arylsulfonyl) amino group",
"optionally substituted heterocyclyl-sulfonylamino group",
"optionally substituted $C_{6-14}$ aryloxy-carbonyl group", and
"optionally substituted $C_{7-16}$ aralkyloxy-carbonyl group" in the Substituent Group A, substituents selected from the following Substituent Group B and the following Substituent Group B' can be mentioned. The number of the substituents is 1 to the maximum substitutable number, more preferably 1 to 3, further preferably 1.

In the present specification, Substituent Group B consists of
(a) a halogen atom;
(b) a hydroxy group;
(c) a nitro group;
(d) a cyano group;
(e) an optionally substituted $C_{6-14}$ aryl group (said $C_{6-14}$ aryl group is optionally substituted by 1-5 (preferably 1-3, more preferably 1) substituent(s) selected from halogen atom, hydroxy group, cyano group, amino group, $C_{1-6}$ alkyl group optionally substituted by 1 to 3 halogen atoms, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.);
(f) an optionally substituted $C_{6-14}$ aryloxy group (said $C_{6-14}$ aryloxy group is optionally substituted by 1-5 (preferably 1-3, more preferably 1) substituent(s) selected from halogen atom, hydroxy group, cyano group, amino group, $C_{1-6}$ alkyl group optionally substituted by 1 to 3 halogen atoms, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.);
(g) an optionally substituted $C_{7-16}$ aralkyloxy group (said $C_{7-16}$ aralkyloxy group is optionally substituted by 1-5 (preferably 1-3, more preferably 1) substituent(s) selected from halogen atom, hydroxy group, cyano group, amino group, $C_{1-6}$ alkyl group optionally substituted by 1 to 3 halogen atoms, mono- or di-$C_{1-6}$-alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.);
(h) an optionally substituted 3- to 14-membered heterocyclic group containing 1 to 5 hetero atoms selected from a nitrogen atom, a sulfur atom, and an oxygen atom (said heterocyclic group is optionally substituted by 1-5 (preferably 1-3, more preferably 1) substituent(s) selected from halogen atom, hydroxy group, cyano group, amino group, $C_{1-6}$ alkyl group optionally substituted by 1 to 3 halogen atoms, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.);
(i) an optionally substituted amino group {for example, amino group optionally mono- or di-substituted by substituent(s) selected from the group consisting of $C_{1-6}$ alkyl group, $C_{2-6}$ alkenyl group, $C_{6-14}$ aryl group, $C_{7-16}$ aralkyl group, heterocyclic group, and heterocyclyl-$C_{1-6}$ alkyl group [said $C_{1-6}$ alkyl group, $C_{2-6}$ alkenyl group, $C_{6-14}$ aryl group, $C_{7-16}$ aralkyl group, heterocyclic group, and heterocyclyl-$C_{1-6}$ alkyl group are each optionally substituted by 1-5 (preferably 1-3, more preferably 1) substituent(s) selected from halogen atom, hydroxy group, cyano group, amino group, $C_{1-6}$ alkyl group optionally substituted by 1 to 3 halogen atoms (said "$C_{1-6}$ alkyl group optionally substituted by 1 to 3 halogen atoms" is not the substituent of $C_{1-6}$ alkyl group and $C_{2-6}$ alkenyl group), mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{3-7}$ cycloalkyloxy-carbonyl group, $C_{6-14}$ aryloxy-carbonyl group, $C_{7-16}$ aralkyloxy-carbonyl group, $C_{1-6}$ alkylsulfanyl group, $C_{3-7}$ cycloalkylsulfanyl group, $C_{1-6}$ alkylsulfinyl group, $C_{3-7}$ cycloalkylsulfinyl group, $C_{1-6}$ alkylsulfonyl group, $C_{3-7}$ cycloalkylsulfonyl group, carbamoyl group, thiocarbamoyl group, mono- or di-$C_{1-6}$ alkyl-carbamoyl group, mono- or di-$C_{6-14}$ aryl-carbamoyl group etc.]};
(j) a $C_{3-7}$ cycloalkyl group;
(k) an optionally substituted $C_{1-6}$ alkoxy group [said $C_{1-6}$ alkoxy group is optionally substituted by 1-5 (preferably 1-3, more preferably 1) substituent(s) selected from halogen atom, hydroxy group, amino group, mono- or di-$C_{1-6}$ alkyl-amino group, mono- or di-$C_{6-14}$ aryl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group, trimethylsilyl(TMS) group etc.];
(l) a formyl group;
(m) a $C_{1-6}$ alkyl-carbonyl group (e.g., acetyl);
(n) a $C_{3-7}$ cycloalkyl-carbonyl group;
(o) a $C_{6-14}$ aryl-carbonyl group;
(p) a $C_{7-16}$ aralkyl-carbonyl group;
(q) a $C_{1-6}$ alkoxy-carbonyl group;
(r) a $C_{6-14}$ aryloxy-carbonyl group;
(s) a $C_{7-16}$ aralkyloxy-carbonyl group;
(t) a $C_{1-6}$ alkylsulfanyl group;
(u) a $C_{1-6}$ alkylsulfinyl group;
(v) a $C_{1-6}$ alkylsulfonyl group;
(w) a carbamoyl group;
(x) a thiocarbamoyl group;

(y) a mono- or di-$C_{1-6}$ alkyl-carbamoyl group (e.g., methylcarbamoyl, ethylcarbamoyl, dimethylcarbamoyl, diethylcarbamoyl, ethylmethylcarbamoyl and the like);
(z) a mono- or di-$C_{6-14}$ aryl-carbamoyl group (e.g., phenylcarbamoyl, 1-naphthylcarbamoyl, 2-naphthylcarbamoyl and the like); and
(aa) a mono- or di-(5- to 7-membered heterocyclyl containing 1 to 4 hetero atoms selected from a nitrogen atom, a sulfur atom and an oxygen atom)-carbamoyl group (e.g., 2-pyridylcarbamoyl, 3-pyridylcarbamoyl, 4-pyridylcarbamoyl, 2-thienylcarbamoyl, 3-thienylcarbamoyl and the like).

In the present specification, Substituent Group B' consists of
(a) an optionally substituted $C_{1-6}$ alkyl group (said $C_{1-6}$ alkyl group is optionally substituted by 1-5 (preferably 1-3, more preferably 1) substituent(s) selected from halogen atom, hydroxy group, cyano group, amino group, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.);
(b) an optionally substituted $C_{2-6}$ alkenyl group (said $C_{2-6}$ alkenyl group is optionally substituted by 1-5 (preferably 1-3, more preferably 1) substituent(s) selected from halogen atom, hydroxy group, cyano group, amino group, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.); and
(c) an optionally substituted $C_{2-6}$ alkynyl group [said $C_{2-6}$ alkynyl group is optionally substituted by 1-5 (preferably 1-3, more preferably 1) substituent(s) selected from halogen atom, hydroxy group, cyano group, amino group, mono- or di-$C_{1-6}$ alkyl-amino group, mono- or di-$C_{6-14}$ aryl-amino group, mono- or di-$C_{7-16}$ aralkyl-amino group, $C_{3-7}$ cycloalkyl group, $C_{1-6}$ alkoxy group, formyl group, $C_{1-6}$ alkyl-carbonyl group, $C_{3-7}$ cycloalkyl-carbonyl group, $C_{6-14}$ aryl-carbonyl group, $C_{7-16}$ aralkyl-carbonyl group, $C_{1-6}$ alkoxy-carbonyl group, $C_{6-14}$ aryloxy-carbonyl group, $C_{7-16}$ aralkyloxy-carbonyl group, $C_{1-6}$ alkylsulfanyl group, $C_{1-6}$ alkylsulfinyl group, $C_{1-6}$ alkylsulfonyl group, carbamoyl group, thiocarbamoyl group, mono- or di-$C_{1-6}$ alkyl-carbamoyl group, mono- or di-$C_{6-14}$ aryl-carbamoyl group etc.).

Each symbol in the formula (I) is explained in the following.

$R^1$ is a hydrogen atom or an optionally substituted $C_{1-6}$ alkyl group.

The "$C_{1-6}$ alkyl group" of the "optionally substituted $C_{1-6}$ alkyl group" for $R^1$ is preferably methyl, ethyl, isobutyl or the like.

The "$C_{1-6}$ alkyl group" optionally has one or more (preferably 1-3, more preferably 1) substituent(s) at any substitutable position(s). Examples of such substituent include substituents selected from the above-mentioned Substituent Group B. When the number of the substituents is not less than 2, the respective substituents may be the same or different.

$R^1$ is preferably a $C_{1-6}$ alkyl group (preferably methyl, ethyl, isobutyl) optionally substituted by 1-3 (more preferably 1) substituent(s) selected from a hydrogen atom; a hydroxy group, a $C_{1-6}$ alkoxy group (preferably methoxy), and a $C_{1-6}$ alkyl-carbonyl group (preferably acetyl).

$X^1$ is CH or a nitrogen atom.
$X^1$ is preferably a nitrogen atom.
In another embodiment, $X^1$ is preferably CH.
Ring A optionally has substituent(s).
As the "substituent" that ring A optionally has, substituents selected from the above-mentioned Substituent Group A can be mentioned. Ring A can have one or more (preferably 1-3, more preferably 1) substituent(s) at any substitutable position(s). When $X^1$ is CH, the substituent may be present on $X^1$.

When the number of the substituents is not less than 2, the respective substituents may be the same or different.

The number of the substituents of ring A is preferably 0 (i.e., unsubstituted).

$X^2$ is $CR^2$ or a nitrogen atom.
$X^3$ is $CR^3$ or a nitrogen atom.
$X^4$ is $CR^4$ or a nitrogen atom.
$X^5$ is $CR^5$ or a nitrogen atom.
$R^2$, $R^3$, $R^4$ and $R^5$ are each independently a hydrogen atom or a substituent.

As the "substituent" shown by $R^2$, $R^3$, $R^4$ or $R^5$, substituent selected from the above-mentioned Substituent Group A can be mentioned.

$R^2$ is preferably a hydrogen atom.
$R^3$ is preferably a hydrogen atom.
$R^4$ is preferably a hydrogen atom.
$R^5$ is preferably a hydrogen atom.
$X^2$ is preferably $CR^2$ wherein $R^2$ is as defined above, more preferably CH.
$X^3$ is preferably $CR^3$ wherein $R^3$ is as defined above, more preferably CH.
$X^4$ is preferably $CR^4$ wherein $R^4$ is as defined above, more preferably CH
$X^5$ is preferably $CR^5$ wherein $R^5$ is as defined above, more preferably CH.

Ring B is an optionally substituted 5- or 6-membered nitrogen-containing heterocycle (said nitrogen-containing heterocycle optionally further forms a fused ring with a ring other than ring C).

$Z^5$ is =N— or —N=.

The "5- or 6-membered nitrogen-containing heterocycle" of the "optionally substituted 5- or 6-membered nitrogen-containing heterocycle" for ring B is not particularly limited as long as $Z^5$ is =N— or —N=, and "5- or 6-membered monocyclic nitrogen-containing aromatic heterocycle" and "5- or 6-membered monocyclic nitrogen-containing non-aromatic heterocycle" can be mentioned.

Examples of the "5- or 6-membered monocyclic nitrogen-containing aromatic heterocycle" include 5- or 6-membered monocyclic nitrogen-containing aromatic heterocycle containing =N— or —N= for $Z^5$, and further optionally containing 1 to 3 hetero atoms selected from an oxygen atom, a sulfur atom (said sulfur atom may be oxidized) and a nitrogen atom.

Preferable examples of such "5- or 6-membered monocyclic nitrogen-containing aromatic heterocycle" include pyridine, pyrimidine, pyridazine, pyrazine, pyrrole, imidazole, pyrazole, thiazole, isothiazole, oxazole, isoxazole, oxadiazole (e.g., 1,2,5-oxadiazole, 1,3,4-oxadiazole), thiadiazole (e.g., 1,2,3-thiadiazole, 1,3,4-thiadiazole), triazole (e.g., 1,2, 4-triazole, 1,2,3-triazole), tetrazole, triazine (e.g., 1,2,4-triazine) and the like.

Examples of the "5- or 6-membered monocyclic nitrogen-containing non-aromatic heterocycle" include 5- or 6-membered monocyclic nitrogen-containing non-aromatic heterocycle containing =N— or —N= for $Z^5$, and further optionally containing 1 to 3 hetero atoms selected from an oxygen atom, a sulfur atom (said sulfur atom may be oxidized) and a nitrogen atom.

Preferable examples of such "5- or 6-membered monocyclic nitrogen-containing non-aromatic heterocycle" include tetrahydropyridine, dihydropyridine, oxazoline, thiazoline, imidazoline, dihydrooxadiazole, pyrazoline, tetrahydropyrimidine, dihydrotriazole, dihydrooxadiazole, thiazine, dihydropyridazine, tetrahydropyridazine, dihydrothioxazine, dihydrothiazine and the like.

As ring B, 5- or 6-membered monocyclic nitrogen-containing aromatic heterocycle such as pyridine, pyrazine, imidazole and the like is preferable, and pyridine or imidazole is preferable.

The "5- or 6-membered nitrogen-containing heterocycle" optionally further forms a fused ring with a ring other than ring C. Examples of such fused ring include a ring formed by condensation of the above-mentioned "5- or 6-membered monocyclic nitrogen-containing aromatic heterocycle" or "5- or 6-membered monocyclic nitrogen-containing non-aromatic heterocycle" with 1 or 2 aromatic heterocycles (e.g., pyrrole, imidazole, pyrazole, pyrazine, pyridine, pyrimidine, thiophene), non-aromatic heterocycles (e.g., pyrrolidine, dihydropyridine, tetrahydropyridine, piperidine, tetrahydropyridazine, dioxole), benzene, cycloalkane (e.g., cyclopropane, cyclohexane, cyclopentane) etc., and the like.

Preferable examples of such fused ring are not particularly limited as long as $Z^5$ is =N— or —N=, and include quinoline, isoquinoline, quinazoline, quinoxaline, benzoxazole, benzisoxazole, benzothiazole, benzimidazole, benzotriazole, indole, indazole, pyrrolopyrazine, imidazopyridine, imidazopyrazine, pyrazolopyridine, thienopyrazole, pyrazolotriazine, triazolopyrimidine, phthalazinine, dihydroindole (e.g., 2,3-dihydro-1H-indole), dihydroisoindole (e.g., 2,3-dihydro-1H-isoindole, 1,3-dihydro-2H-isoindole), dihydroquinoline (e.g., 1,2-dihydroquinoline, 3,4-dihydroquinoline), tetrahydroquinoline (e.g., 1,2,3,4-tetrahydroquinoline), dihydroisoquinoline (e.g., 1,2-dihydroisoquinoline), tetrahydroisoquinoline (e.g., 1,2,3,4-tetrahydroisoquinoline), dihydrophthalazine (e.g., 3,4-dihydrophthalazine, 1,4-dihydrophthalazine), benzothiazine (e.g., 3,4-dihydro-2H-1,4-benzothiazine) and the like.

The "5- or 6-membered nitrogen-containing heterocycle" of the "optionally substituted 5- or 6-membered nitrogen-containing heterocycle" for ring B optionally has one or more (preferably 1-3, more preferably 1) substituent(s) at any substitutable position(s). Examples of such substituent include substituents selected from the above-mentioned Substituent Group A. When the number of the substituents is not less than 2, the respective substituents may be the same or different.

Ring B is preferably 5- or 6-membered nitrogen-containing heterocycle (preferably 5- or 6-membered monocyclic nitrogen-containing aromatic heterocycle such as pyridine, pyrazine, imidazole and the like) optionally substituted by 1-3 (more preferably 1) $C_{1-6}$ alkyl group(s) (preferably methyl), particularly preferably 5- or 6-membered monocyclic nitrogen-containing aromatic heterocycle such as pyridine, imidazole and the like, which is optionally substituted by 1-3 (preferably 1) $C_{1-6}$ alkyl group(s) (preferably methyl).

Ring C is an optionally substituted 5- or 6-membered ring.

Y is a ring C-constituting atom selected from a carbon atom and a nitrogen atom.

$Z^1$ is a ring C-constituting atom selected from a carbon atom and a nitrogen atom.

$Z^2$, $Z^3$ and $Z^4$ are each independently a ring C-constituting atom selected from a carbon atom, a nitrogen atom, a sulfur atom and an oxygen atom.

The "5- or 6-membered ring" of the "optionally substituted 5- or 6-membered ring" for ring C is preferably pyridine, dihydropyridine, pyrazole, tetrahydropyridine, piperidine, dihydropyrazole, imidazole, dihydroimidazole or the like.

As the "ring C-constituting atom selected from a carbon atom and a nitrogen atom" for Y or

and the like can be mentioned for

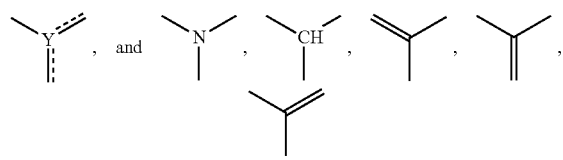

and the like can be mentioned for

(provided that when p is 0, the bond between Y and $Z^4$ is a single bond).

Examples of the "ring C-constituting atom selected from a carbon atom, a nitrogen atom, a sulfur atom and an oxygen atom" for $Z^2$, $Z^3$ or $Z^4$ include —O—, —S—, —N=, =N—, —NR$^6$—, —CR$^7$=, =CR$^7$—, —SO—, —SO$_2$—, or an optionally substituted methylene group and the like (provided that when p is 0, the bond between Y and $Z^4$ is a single bond).

$R^6$ and $R^7$ are each independently a hydrogen atom or a substituent.

As the "substituent" for $R^6$ or $R^7$, substituents selected from the above-mentioned Substituent Group A can be mentioned.

The "methylene group" of the "optionally substituted methylene group" optionally has 1 or 2 substituent(s). As such substituent, substituents selected from the above-mentioned Substituent Group A and oxo group can be mentioned. When the number of the substituents is 2, these substituents may be the same or different.

The "optionally substituted methylene group" is preferably a methylene group.

$Z^2$ is preferably —CR$^7$=, =CR$^7$— wherein $R^7$ is as defined above, or an optionally substituted methylene group, more preferably —CH=, =CH— or a methylene group.

$Z^3$ is preferably —N=, =N—, —NR$^6$— wherein $R^6$ is as defined above, —CR$^7$=, =CR$^7$— wherein $R^7$ is as defined above, or an optionally substituted methylene group, more preferably —N=, =N—, —NR$^6$— wherein $R^6$ is preferably an optionally substituted $C_{1-6}$ alkyl group (preferably methyl, ethyl), —CR$^7$=, =CR$^7$— wherein $R^7$ is preferably a hydrogen atom, an optionally substituted $C_{1-6}$ alkyl group (preferably ethyl), an optionally substituted $C_{1-6}$ alkoxy group (preferably methoxy), or a methylene group optionally substituted by an oxo group.

$Z^4$ is preferably —N═, —NR$^6$— wherein R$^6$ is as defined above, —CR$^7$═, ═CR$^7$— wherein R$^7$ is as defined above, or an optionally substituted methylene group, more preferably —N═, —NR$^6$— wherein R$^6$ is preferably an optionally substituted $C_{1-6}$ alkyl group (preferably methyl, ethyl), —CH═, ═CH—, or a methylene group (provided that when p is 0, the bond between Y and $Z^4$ is a single bond).

$Z^3$ and $Z^4$ may be joined to form ring D.

Ring D is an optionally substituted 5- or 6-membered ring.

The "5- or 6-membered ring" of the "optionally substituted 5- or 6-membered ring" for ring D is preferably pyridine or imidazole.

The "5- or 6-membered ring" optionally has one or more (preferably 1-3, more preferably 1) substituent(s) at any substitutable position(s). As such substituent, substituents selected from the above-mentioned Substituent Group A can be mentioned. When the number of the substituents is not less than 2, the respective substituents may be the same or different.

Ring D is preferably a 5- or 6-membered ring (preferably pyridine, imidazole) optionally substituted by 1-3 (more preferably 1) $C_{1-6}$ alkyl group(s) (preferably methyl).

As a compound represented by the formula (I), a compound represented by the formula (I-i), the formula (I-ii) or the formula (I-iii) is preferable.

Each symbol in the formula (I-i) is explained in the following.

$R^1$, $X^1$, ring A, $X^2$, $X^3$, $X^4$, $X^5$, ring B and $Z^5$ are as defined for each symbol in the above-mentioned formula (I).

Ring $C^1$ is an optionally substituted 5-membered ring.

$Z^1$, $Z^{3\prime}$ and $Z^{4\prime}$ are each independently a ring $C^1$-constituting atom selected from a carbon atom and a nitrogen atom.

As the "5-membered ring" of the "optionally substituted 5-membered ring" for ring $C^1$, 5-membered rings from the aforementioned "5- or 6-membered non-aromatic hydrocarbon ring", the aforementioned "5- or 6-membered aromatic heterocycle", and the aforementioned "5- or 6-membered non-aromatic heterocycle" can be mentioned. As the substituent that the "5-membered ring" optionally has, one or more (preferably 1-3, more preferably 1) substituent(s) selected from the above-mentioned Substituent Group A can be mentioned.

As the "ring $C^1$-constituting atom selected from a carbon atom and a nitrogen atom" for $Z^1$, $Z^{3\prime}$ or $Z^{4\prime}$,

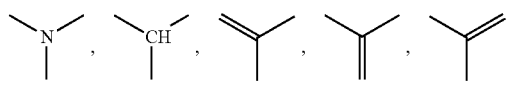

and the like can be mentioned for

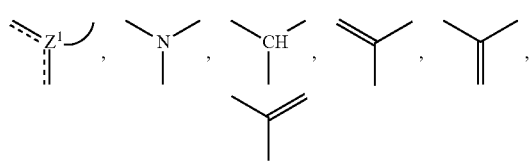

and the like can be mentioned for

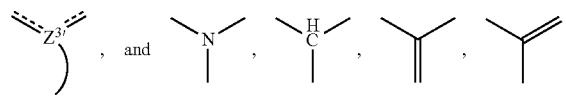

and the like can be mentioned for

The "5-membered ring" for $C^1$ optionally has one or more (preferably 1-3, more preferably 1) substituent(s) at any substitutable position(s). When $Z^1$, $Z^{3\prime}$ or $Z^{4\prime}$ is

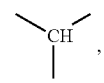

the substituent may be present on $Z^1$, $Z^{3\prime}$ or $Z^{4\prime}$. As such substituent, substituents selected from the above-mentioned. Substituent Group A can be mentioned. When the number of the substituents is not less than 2, the respective substituents may be the same or different.

$Z^1$ and $Z^{3\prime}$ are represented by

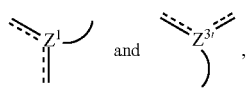

respectively, and one is preferably

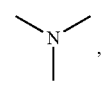

and the other is

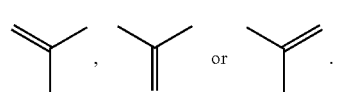

$Z^{4\prime}$ is represented by

preferably

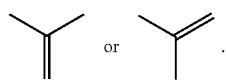

The "5-membered ring" of the "optionally substituted 5-membered ring" for ring $C^1$ is preferably 5-membered nitrogen-containing heterocycle (e.g., imidazolidine, dihydropyrrole, pyrrolidine, dihydroimidazole), more preferably 5-membered non-aromatic nitrogen-containing heterocycle (e.g., imidazolidine).

The number of the substituents of ring $C^1$ is preferably 0 (i.e., unsubstituted).

Ring D is an optionally substituted 5- or 6-membered ring.

The "5- or 6-membered ring" of the "optionally substituted 5- or 6-membered ring" for ring D is benzene, the aforementioned "5- or 6-membered non-aromatic hydrocarbon ring", "5- or 6-membered aromatic heterocycle", and "5- or 6-membered non-aromatic hydrocarbon ring. Ring D is preferably pyridine or imidazole.

The "5- or 6-membered ring" optionally has one or more (preferably 1-3, more preferably 1) substituent(s) at any substitutable position(s). As such substituent, substituents selected from the above-mentioned Substituent Group A can be mentioned. When the number of the substituents is not less than 2, the respective substituents may be the same or different.

The substituent that the "5- or 6-membered ring" optionally has is preferably an optionally substituted $C_{1-6}$ alkyl group (preferably methyl). As the substituent that the "$C_{1-6}$ alkyl group" of the "optionally substituted $C_{1-6}$ alkyl group" optionally has, 1 to 3 substituents selected from the above-mentioned Substituent Group B can be mentioned.

In the formula (I-i), ring D is preferably a 5- or 6-membered ring (preferably pyridine, imidazole) optionally substituted by 1-3 (more preferably 1) $C_{1-6}$ alkyl group(s) (preferably methyl). Ring D is more preferably an unsubstituted 5-membered ring (e.g., imidazole).

In the formula (I-i), ring B is preferably a 5- or 6-membered ring (preferably pyridine, imidazole) optionally substituted by 1-3 (more preferably 1) $C_{1-5}$ alkyl group(s) (preferably methyl). Ring B is more preferably a 6-membered ring (preferably pyridine) optionally substituted by 1-3 (more preferably 1) $C_{1-6}$ alkyl group(s) (preferably methyl).

In the formula (I-i), a preferable embodiment of $R^1$ corresponds to that of the formula (I).

In the formula (I-i), $X^1$ is preferably CH or a nitrogen atom.

In the formula (I-i), the number of the substituents of ring A is preferably 0 (i.e., unsubstituted).

In the formula (I-i), $X^2$, $X^3$, $X^4$, and $X^5$ are each preferably CH.

Particularly preferable embodiments of the compound of the formula (I-i) include a compound represented by the following formula (I-i)' and a salt thereof.

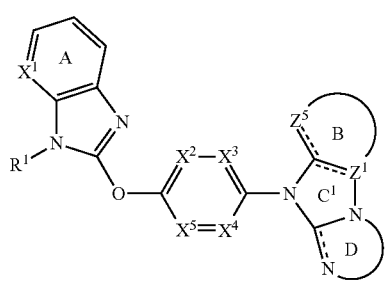

(I-i)' wherein each symbol is as defined for each symbol in the above-mentioned formula (I).

Preferable embodiment of each substituent in the formula (I-i)' corresponds to that of each substituent in the formula (I-i).

Preferable examples of a compound represented by the formula (I-i)' or a salt thereof (hereinafter sometimes to be referred to as compound (I-i)') specifically include the following compounds.

[Compound (I-i)']

Compound (I-i)' wherein $Z^1$ is a carbon atom, $Z^5$ is =N— or —N=, $X^1$ is CH or a nitrogen atom, the number of the substituents of ring A is 0 (i.e., unsubstituted), $X^2$, $X^3$, $X^4$, and $X^5$ are each CH, ring B is a 6-membered ring (preferably pyridine) optionally substituted by 1-3 (more preferably 1) $C_{1-6}$ alkyl group(s) (preferably methyl), ring D is an unsubstituted 5-membered ring (e.g., imidazole), and $R^1$ is a hydrogen atom, or a $C_{1-6}$ alkyl group (preferably methyl, ethyl, isobutyl) optionally substituted by 1-3 (more preferably 1) substituent(s) selected from hydroxy group, $C_{1-6}$ alkoxy group (preferably methoxy), and $C_{1-6}$ alkyl-carbonyl group (preferably acetyl).

Each symbol in the formula (I-ii) is explained in the following.

$R^1$, $X^1$, ring A, $X^2$, $X^3$, $X^4$, $X^5$, ring B and $Z^5$ are as defined for each symbol in the above-mentioned formula (I).

Ring $C^2$ is an optionally substituted 5-membered ring.

Y is a ring $C^2$-constituting atom selected from a carbon atom and a nitrogen atom.

$Z^1$ is a ring $C^2$-constituting atom selected from a carbon atom and a nitrogen atom.

$Z^{3''}$ is a ring $C^2$-constituting atom selected from a carbon atom, a nitrogen atom, a sulfur atom and an oxygen atom.

As the "5-membered ring" of the "optionally substituted 5-membered ring" for ring $C^2$, 5-membered rings from the aforementioned "5- or 6-membered non-aromatic hydrocarbon ring", the aforementioned "5- or 6-membered aromatic heterocycle", and the aforementioned "5- or 6-membered non-aromatic heterocycle" can be mentioned. As the substituent that the "5-membered ring" optionally has, one or more (preferably 1-3, more preferably 1) substituent(s) selected from the above-mentioned Substituent Group A can be mentioned.

As the "ring $C^2$-constituting atom selected from a carbon atom and a nitrogen atom" for Y or $Z^1$, for example,

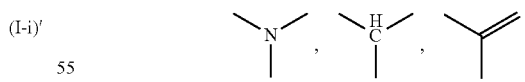

and the like can be mentioned for

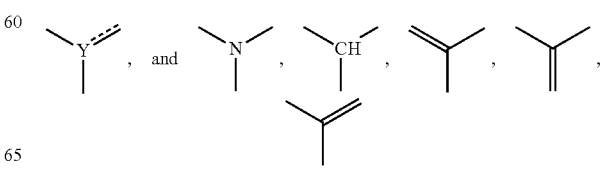

and the like can be mentioned for

wherein the bond between Y and Z$^{4''}$ is a single bond.

Y is preferably

wherein the bond between Y and Z$^{4''}$ is a single bond.

Z$^1$ is preferably

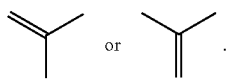

As the "ring C$^2$-constituting atom selected from a carbon atom, a nitrogen atom, a sulfur atom and an oxygen atom" for Z$^{3''}$, for example, —O—, —S—, —N=, =N—, —NR$^6$—, —CR$^7$=, =CR$^7$—, —SO—, —SO$_2$—, or optionally substituted methylene group and the like can be mentioned.

R$^6$ and R$^7$ are each independently a hydrogen atom or a substituent.

As the "substituent" for R$^6$ or R$^7$, substituents selected from the above-mentioned Substituent Group A can be mentioned.

R$^6$ is preferably an optionally substituted C$_{1-6}$ alkyl group (preferably methyl, ethyl).

R$^7$ is preferably a hydrogen atom, an optionally substituted C$_{1-6}$ alkyl group (preferably ethyl), or an optionally substituted C$_{1-6}$ alkoxy group (preferably methoxy).

The "methylene group" of the "optionally substituted methylene group" optionally has 1 or 2 substituents. As such substituent, substituents selected from the above-mentioned Substituent Group A and oxo group can be mentioned. When the number of the substituents is 2, these substituents may be the same or different.

The "optionally substituted methylene group" is preferably a carbonyl group.

Z$^{3''}$ is preferably —N=, =CR$^7$— wherein R$^7$ is as defined above or an optionally substituted methylene group, more preferably —N=, =CR$^7$— wherein R$^7$ is a C$_{1-6}$ alkyl group (preferably ethyl) or a C$_{1-6}$ alkoxy group (preferably methoxy), or a methylene group optionally substituted by an oxo group.

Z$^{4''}$ is —O—, —S—, —N=, —NR$^{6'}$—, —CR$^{7'}$=, —SO—, —SO$_2$— or an optionally substituted methylene group (excluding carbonyl group).

The "methylene group" of the "optionally substituted methylene group" for Z$^{4''}$ optionally has 1 or 2 substituent(s). As such substituent, substituents selected from the above-mentioned Substituent Group A can be mentioned. When the number of the substituents is 2, these substituents may be the same or different.

In another embodiment, Z$^{4''}$ is —O—, —S—, —N=, —NR$^{6'}$—, —CR$^{7'}$=, —SO—, —SO$_2$— or —CR$^8$R$^9$—.

R$^{6'}$, R$^{7'}$, R$^8$ and R$^9$ are each independently a hydrogen atom or a substituent.

As the "substituent" for R$^{6'}$, R$^{7'}$, R$^8$ or R$^9$, substituents selected from the above-mentioned Substituent Group A can be mentioned.

R$^{6'}$ is preferably a C$_{1-6}$ alkyl group (preferably methyl, ethyl).

R$^{7'}$, R$^8$ and R$^9$ are each preferably a hydrogen atom.

Z$^{4''}$ is preferably —N=, —NR$^{6'}$— wherein R$^{6'}$ is as defined above, more preferably —N=, —NR$^{6'}$— wherein R$^{6'}$ is a C$_{1-6}$ alkyl group (preferably methyl, ethyl).

The "5-membered ring" of the "optionally substituted 5-membered ring" for ring C$^2$ is preferably pyrazole or pyrazoline.

The "5-membered ring" may have one or more (preferably 1-3, more preferably 1) substituent(s) at any substitutable position(s), and preferably has one or more (preferably 1-3, more preferably 1) substituent(s) on Z$^{3''}$ or Z$^{4''}$. When Y or Z$^1$ is

the substituent may be present on Y or Z$^1$. As such substituent, substituents selected from the above-mentioned Substituent Group A can be mentioned. When the number of the substituents is not less than 2, the respective substituents may be the same or different.

In the formula (I-ii), a preferable embodiment of R$^1$ corresponds to that of the formula (I). R$^1$ is more preferably a hydrogen atom; methyl.

In the formula (I-ii), X$^1$ is preferably CH or a nitrogen atom. X$^1$ is more preferably a nitrogen atom.

In the formula (I-ii), the number of the substituents of ring A is preferably 0 (i.e., unsubstituted).

In the formula (I-ii), X$^2$, X$^3$, X$^4$, and X$^5$ are each preferably CH.

Preferable examples of a compound represented by the formula (I-ii) or a salt thereof (hereinafter sometimes to be referred to as compound (I-ii)) specifically include the following compounds.

[Compound (I-ii)]

Compound (I-ii) wherein Y is

wherein the bond between Y and Z$^{4''}$ is a single bond,

Z$^1$ is

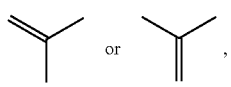

Z$^{3''}$ is —N=, =CR$^7$— wherein R$^7$ is a C$_{1-6}$ alkyl group (preferably ethyl) or a C$_{1-6}$ alkoxy group (preferably methoxy) or a methylene group optionally substituted by an oxo group, Z$^{4''}$ is —N= or —NR$^{6'}$— wherein R$^{6'}$ is a C$_{1-6}$ alkyl group (preferably methyl, ethyl), Z$^5$ is =N— or —N=, X$^1$ is CH or a nitrogen atom, the number of the substituents of ring A is 0 (i.e., unsubstituted),
$X^2$, $X^3$, $X^4$, and $X^5$ are each CH,
ring B is a 6-membered ring (preferably pyridine) optionally substituted by 1-3 (more preferably 1) $C_{1-6}$ alkyl group(s) (preferably methyl), and
$R^1$ is a hydrogen atom, or a $C_{1-6}$ alkyl group (preferably methyl, ethyl, isobutyl) optionally substituted by 1-3 (more preferably 1) substituent(s) selected from a hydroxy group, a $C_{1-6}$ alkoxy group (preferably methoxy), and a $C_{1-6}$ alkylcarbonyl group (preferably acetyl).

Each symbol in the formula (I-iii) is explained in the following.

$R^1$, $X^1$, ring A, $X^2$, $X^3$, $X^4$, $X^5$, ring B and $Z^5$ are as defined for each symbol in the above-mentioned formula (I).

Ring $C^3$ is an optionally substituted 6-membered ring.

Y is a ring $C^3$-constituting atom selected from a carbon atom and a nitrogen atom.

$Z^1$ is a ring $C^3$-constituting atom selected from a carbon atom and a nitrogen atom.

$Z^2$, $Z^3$ and $Z^4$ are each independently a ring $C^3$-constituting atom selected from a carbon atom, a nitrogen atom, a sulfur atom and an oxygen atom.

As the "6-membered ring" of the "optionally substituted 6-membered ring" for ring $C^3$, 6-membered rings from the aforementioned "5- or 6-membered non-aromatic hydrocarbon ring", the aforementioned "5- or 6-membered aromatic heterocycle", and the aforementioned "5- or 6-membered non-aromatic heterocycle" can be mentioned. As the substituent that the "6-membered ring" optionally has, one or more (preferably 1-3, more preferably 1) substituent(s) selected from the above-mentioned Substituent Group A can be mentioned.

The "ring $C^3$-constituting atom selected from a carbon atom and a nitrogen atom" for Y or $Z^1$, for example,

and the like can be mentioned for

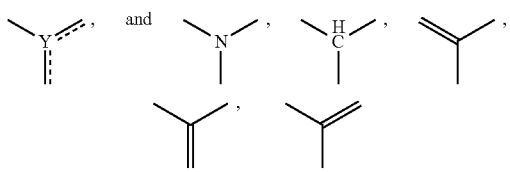

and the like can be mentioned for

Y is preferably

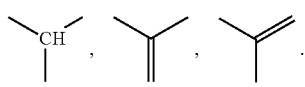

$Z^1$ is preferably

As the "$C^3$-constituting atom selected from a carbon atom, a nitrogen atom, a sulfur atom and an oxygen atom ring" for $Z^2$, $Z^3$ or $Z^4$, for example, —O—, —S—, —N=, =N—, —$NR^6$—, —$CR^7$=, =$CR^7$—, —SO—, —$SO_2$—, an optionally substituted methylene group and the like can be mentioned.

$R^6$ and $R^7$ are each independently a hydrogen atom or a substituent.

As the "substituent" for $R^6$ or $R^7$, substituents selected from the above-mentioned Substituent Group A can be mentioned.

$R^6$ and $R^7$ are each preferably a hydrogen atom.

The "methylene group" of the "optionally substituted methylene group" optionally has 1 or 2 substituents. As such substituent, substituents selected from the above-mentioned Substituent Group A and oxo group can be mentioned. When the number of the substituents is 2, these substituents may be the same or different.

The "optionally substituted methylene group" is preferably a methylene group.

$Z^2$, $Z^3$ and $Z^4$ are each preferably —$CR^7$=, =$CR^7$— wherein $R^7$ is as defined above, or an optionally substituted methylene group, more preferably —CH=, =CH— or a methylene group.

$Z^3$ and $Z^4$ may be joined to form ring D.

Ring D is an optionally substituted 5- or 6-membered ring.

When $Z^3$ and $Z^4$ are joined to form ring D, the formula (I-iii) is represented by the formula (I-iii)':

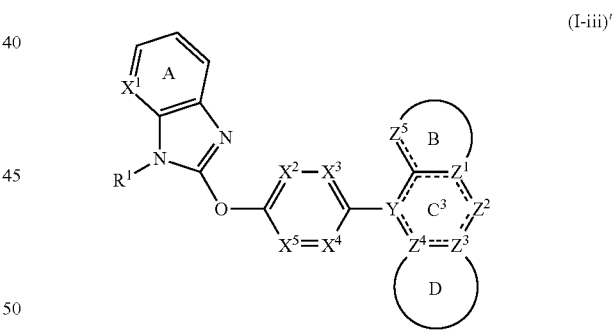

wherein each symbol is as defined above.

The "5- or 6-membered ring" of the "optionally substituted 5- or 6-membered ring" for ring D optionally has one or more (preferably 1-3, more preferably 1) substituent(s) at any substitutable position(s). As such substituent, substituents selected from the above-mentioned Substituent Group A can be mentioned. When the number of the substituents is not less than 2, the respective substituents may be the same or different.

Preferable embodiment of each substituent in the formula (I-iii) corresponds to that of each substituent in the formula (I).

In the formula (I-iii), $R^1$ is more preferably a hydrogen atom.

In the formula (I-iii), $X^1$ is more preferably CH.

In the formula (I-iii), the number of the substituents of ring A is preferably 0 (i.e., unsubstituted).

In the formula (I-iii), $X^2$, $X^3$, $X^4$ and $X^5$ are each preferably CH.

In the formula (I-iii), ring B is preferably a 5- or 6-membered ring (preferably pyridine, imidazole) optionally substituted by 1-3 (more preferably 1) $C_{1-5}$ alkyl group(s) (preferably methyl). Ring B is more preferably a 5-membered ring (preferably imidazole) optionally substituted by 1-3 (more preferably 1) $C_{1-6}$ alkyl group (preferably methyl).

Preferable examples of a compound represented by the formula (I-iii) or a salt thereof (hereinafter sometimes to be referred to as compound (I-iii)) specifically include the following compounds.

[Compound (I-iii)]

Compound (I-iii) wherein Y is

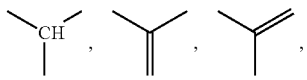

$Z^1$ is

$Z^2$, $Z^3$ and $Z^4$ are each —CH=, =CH— or a methylene group,
$Z^5$ is =N— or —N=,
$X^1$ is CH,
the number of the substituents of ring A is 0 (i.e., unsubstituted),
$X^2$, $X^3$, $X^4$, and $X^5$ are each CH,
ring B is a 5-membered ring (preferably imidazole) optionally substituted by 1-3 (more preferably 1) $C_{1-6}$ alkyl group(s) (preferably methyl), and
$R^1$ is a hydrogen atom, or a $C_{1-6}$ alkyl group (preferably methyl, ethyl, isobutyl) optionally substituted by 1-3 (more preferably 1) substituent(s) selected from a hydroxy group, a $C_{1-6}$ alkoxy group (preferably methoxy), and a $C_{1-6}$ alkyl-carbonyl group (preferably acetyl).

The most preferable compound (I) is the compound described in Example 14 and 15 or a salt thereof.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like.

Among them, salts that are pharmaceutically acceptable are preferable. For example, in the case when acidic functional group is present in the compound, for example, inorganic salts including alkali metal salts (e.g., sodium salts, potassium salt, etc.) and alkali earth metal salts (e.g., calcium salts, magnesium salts, barium salts, etc.) and ammonium salts are preferable. In the case when basic functional group is present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

Compound (I) and a salt thereof are to be also referred to by a generic term of the compound of the present invention.

When the compound (I) includes isomers such as tautomers, optical isomers, stereoisomers, regioisomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heat of fusion, hygroscopicity, solubility, and stability. A co-crystal or a co-crystal salt can be produced according to a per se known co-crystallization method.

The compound (I) may be a solvate (e.g., hydrate) or a non-solvate and both are included in the compound (I).

Compounds labeled with or substituted by isotopes (e.g., $^2H$, $^3H$, $^{11}C$, $^{14}C$, $^{18}F$, $^{35}S$, $^{125}I$, etc.) are also included in compound (I). The compound (I) labeled with or substituted by isotopes can be used as, for example, a tracer used for Positron Emission Tomography (PET) (PET tracer), and are useful in the field of medical diagnosis and the like.

The compound (I) or a prodrug of compound (I) means compound (I) or a compound which is converted to compound (I) with a reaction due to an enzyme, an gastric acid, etc. under the physiological condition in the living body, that is, compound (I) or a compound which is converted to compound (I) with oxidation, reduction, hydrolysis, etc. due to an enzyme; compound (I) or a compound which is converted to compound (I) by hydrolysis etc. due to gastric acid, etc.

The compound (I) or a prodrug of compound (I) may be a compound obtained by subjecting compound (I) or an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting compound (I) or a hydroxy group in compound (I) to an acylation, alkylation, phosphorylation or boration (e.g., a compound obtained by subjecting compound (I) or an hydroxy group in compound (I) to an acetylation, palmitoylation, propanoylation, pivaloylation, succinylation, fumarylation, alanylation, dimethylaminomethylcarbonylation, etc.); a compound obtained by subjecting compound (I) or a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) or compound (I) by a known method. compound (I) or a prodrug of compound (I) may also be one which is converted into compound (I) or compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

[Production Method]

The production methods of the compound of the present invention are described below.

Compound (I) or a salt thereof can be produced by a method known per se, for example, the production method shown by production method A and production method B to be described in detail in the following or a method analogous thereto.

In each of the following production methods, each starting compound used for the production of compound (I) may form a salt. Examples of such salt include those similar to the salts of the above-mentioned compound (I) can be mentioned.

In addition, each starting compound used for the production of compound (I) can be used directly in the form of a reaction mixture or as a crude product in the following reactions. However, it can be isolated from the reaction mixture according to the ordinary method. The product itself can be easily purified by the known means of isolation such as extraction, concentration, neutralization, filtration, distillation, recrystallization and chromatography. Examples of the solvent used for the above-mentioned recrystallization include water, alcohols, ethers, hydrocarbons, amides, halogenated hydrocarbons, nitriles, ketones, esters, sulfoxides, organic acids and the like can be mentioned. These solvents can be used singly, or two or more kinds of the solvents may be used at a suitable mixing ratio, for example, 1:1-1:10. Alternatively, when the compound in the schemes is commercially available, a commercial product can be used directly and in addition, those which are manufactured by the known methods or by a comparable method can be used.

When the substituents that compound (I) have include a convertible functional group (e.g., carboxy group, amino group, hydroxyl group, carbonyl group, mercapto group, $C_{1-6}$ alkoxy-carbonyl group, $C_{6-14}$ aryloxy-carbonyl group, $C_{7-16}$ aralkyloxy-carbonyl group, sulfo group, halogen atom etc.), various compounds can be produced by converting such functional group by a method known per se or a method analogous thereto.

When the substituent is a carboxy group, for example, it can be converted by reactions such as esterification, reduction, amidation, conversion reaction to optionally protected amino group and the like.

When the substituent is an amino group, for example, it can be converted by reactions such as amidation, sulfonylation, nitrosation, alkylation, arylation, imidation and the like.

When the substituent is a hydroxyl group, for example, it can be converted by reactions such as esterification, carbamoylation, sulfonylation, alkylation, arylation, oxidation, halogenation and the like.

When the substituent is a carbonyl group, for example, it can be converted by reactions such as reduction, oxidation, imination (including oximation, hydrazonation), (thio)ketalization, alkylidenation, thiocarbonylation and the like.

When the substituent is a mercapto group, for example, it can be converted by reactions such as alkylation, oxidation and the like.

When the substituent is a $C_{1-6}$ alkoxy-carbonyl group, $C_{6-14}$ aryloxy-carbonyl group, or a $C_{7-16}$ aralkyloxy-carbonyl group, for example, it can be converted by reactions such as reduction, hydrolysis and the like.

When the substituent is a sulfo group, for example, it can be converted by reactions such as sulfonamidation, reduction and the like.

When the substituent is a halogen atom, for example, it can be converted by various nucleophilic substitution reactions, various coupling reactions and the like.

In each of the aforementioned reactions, when the compound is obtained in a free form, it may be converted to a salt by a conventional method, and when it is obtained as a salt, it can also be converted to a free form or other salt by a conventional method.

These functional groups can be converted according to a is method known per se, for example, the method described in "Comprehensive Organic Transformations" (by Richard C. Larock, published in 1999 by Wiley-VCH).

In each reaction in the production method of compound (I) and each reaction in the synthesis of the starting compound, when the starting compound has an amino group, a carboxy group, a hydroxy group or a heterocyclic group as a substituent, a protective group generally used in the peptide chemistry and the like may be introduced into these groups, and the object compound can be obtained by removing the protective group as necessary after the reaction.

Examples of the protective group of an amino group include a formyl group, and a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl(Boc) etc.), an allyloxycarbonyl (Alloc) group, a phenyloxycarbonyl group, a fluorenylmethoxycarbonyl(Fmoc) group, a $C_{7-10}$ alkyl-carbonyl group (e.g., benzylcarbonyl etc.), a $C_{7-10}$ aralkyl-oxycarbonyl group (e.g., benzyloxycarbonyl(Z) etc.), a $C_{7-10}$ aralkyl group (e.g., benzyl etc.), a 2-(trimethylsilyl)ethoxymethyl(SEM) group, a trityl group, a phthaloyl group, an N,N-dimethylaminomethylene group and the like, each of which may have substituent(s). As these substituents, a phenyl group, a halogen atom (e.g., fluorine atom, chlorine atom, bromine atom, iodine atom etc.), a $C_{1-6}$ alkyl-carbonyl group (e.g., methylcarbonyl, ethylcarbonyl, butylcarbonyl etc.), a nitro group and the like are used, wherein the number of substituents is about 1-3.

Examples of the protective group for a carboxy group include a $C_{1-6}$ alkyl group (e.g., methyl, ethyl, n-propyl, isopropyl, n-butyl, tert-butyl etc.), an allyl group, a benzyl group, a phenyl group, a trityl group, a trialkylsilyl group and the like, each of which may have substituent(s). As these substituents, a halogen atom (e.g., fluorine atom, chlorine atom, bromine atom, iodine atom etc.), a formyl group, a $C_{1-6}$ alkyl-carbonyl group (e.g., acetyl, ethylcarbonyl, butylcarbonyl etc.), a nitro group and the like are used, wherein the number of substituents is about 1-3.

Examples of the protective group for a hydroxy group include a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group, a silyl group and the like, each of which may have substituent(s). As these substituents, a halogen atom (e.g., fluorine atom, chlorine atom, bromine atom, iodine atom etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like are used, wherein the number of substituents is about 1-4.

These protective groups can be introduced or removed by a method known per se, for example, the method described in Protective Groups in Organic Synthesis, $3^{rd}$ Ed. (Theodora W. Greene, Peterg. M. Wuts), Wiley-Interscience (1999) and the like.

When compound (I) is present as a configurational isomer, a diastereomer, a conformer and the like, each can be isolated by a known means. When compound (I) is an optical isomer, racemates can be resolved by a general optical resolution means, whereby an optically active forms ((+) form, (−) form) can be isolated.

When compound (I) has an optical isomer, a stereoisomer, a regioisomer, a rotamer or a tautomer, these are also encompassed in compound (I), and can be obtained as a single product according to synthesis and separation methods known per se.

For example, the method of optical resolution may be a method known per se, such as a fractional recrystallization method, a chiral column method, a diastereomer method etc.
1) Fractional Recrystallization Method A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.
2) Chiral Column Method A method wherein a racemate or a salt thereof is applied to a column for separation of an optical isomer (a chiral column) to allow separation. In the case of a liquid chromatography, for example, a mixture of the optical isomers is applied to a chiral column such as ENALTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer. In the case of a gas chromatography, for example, a chiral column such as CP-Chirasil-DeX CB (manufactured by GL Sciences Inc.) and the like is used to allow separation.
3) Diastereomer Method A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxy group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

The salt of compound (I) can be produced by a method known per se. For example, when compound (I) is a basic compound, the salt can be produced by adding an inorganic acid or an organic acid, and when compound (I) is an acidic compound, the salt can be produced by adding an organic base or an inorganic base.

The solvents, acids and bases used in the production method of the compound of the present invention are explained below.

As the "alcohols", for example, methanol, ethanol, 1-propanol, 2-propanol, tert-butyl alcohol and the like are used.

As the "ethers", for example, dimethyl ether, diethyl ether, diisopropyl ether, diphenyl ether, tetrahydrofuran, 1,4-dioxane, 1,2-dimethoxyethane and the like are used.

As the "hydrocarbons", for example, benzene, toluene, cyclohexane, hexane and the like are used.

As the "amides", for example, N,N-dimethylformamide, N,N-dimethylacetamide, N-methylpyrrolidine, hexamethylphosphoric triamide and the like are used.

As the "halogenated hydrocarbons", for example, dichloromethane, chloroform, carbon tetrachloride, 1,2-dichloroethane, chlorobenzene and the like are used.

As the "nitriles", for example, acetonitrile, propionitrile and the like are used.

As the "ketones", for example, acetone, ethyl methyl ketone and the like are used.

As the "esters", for example, ethyl acetate and the like are used.

As the "sulfoxides", for example, dimethyl sulfoxide and the like are used.

As the "organic acids", for example, formic acid, acetic acid, propionic acid, trifluoroacetic acid, citric acid, methanesulfonic acid, p-toluenesulfonic acid and the like are used.

As the "inorganic bases", for example, sodium hydroxide, potassium hydroxide, lithium hydroxide, barium hydroxide and the like are used.

As the "organic bases", for example, triethylamine, pyridine and the like can be mentioned.

As the "basic salts", for example, sodium carbonate, potassium carbonate, cesium carbonate, sodium hydrogen carbonate, sodium acetate, ammonium acetate and the like are used.

As the "tertiary amines", for example, triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like are used.

As the "alkali metal hydrides", for example, sodium hydride, potassium hydride and the like are used.

As the "metal amides", for example, sodium amide, lithium diisopropylamide, lithium hexamethyldisilazide and the like are used.

As the "alkyl metals", for example, butyllithium, sec-butyllithium, tert-butyllithium and the like are used.

As the "aryl metals", for example, phenyllithium and the like are used.

As the "metal alkoxides", for example, sodium methoxide, sodium ethoxide, sodium tert-butoxide, potassium tert-butoxide and the like are used.

[Production Method A]

In compound (I), a compound wherein Y is a carbon atom (hereinafter to be referred to as compound (1a)) can be produced by, for example, the method shown in the following reaction scheme or a method analogous thereto.

wherein $L^1$ is a leaving group; $R^{10}$ is a hydrogen atom or an optionally substituted $C_{1-6}$ alkyl group, or two $R^{10}$ may form a 4,4,5,5-tetramethyl-1,3,2-dioxaborane ring together with the adjacent two oxygen atoms, and further with a boron atom; Q is a halogen atom or a trifluoromethylsulfonyl group; and other symbols are as defined above.

Examples of the leaving group for $L^1$ include halogen atom (e.g., fluorine atom, chlorine atom, bromine atom, iodine

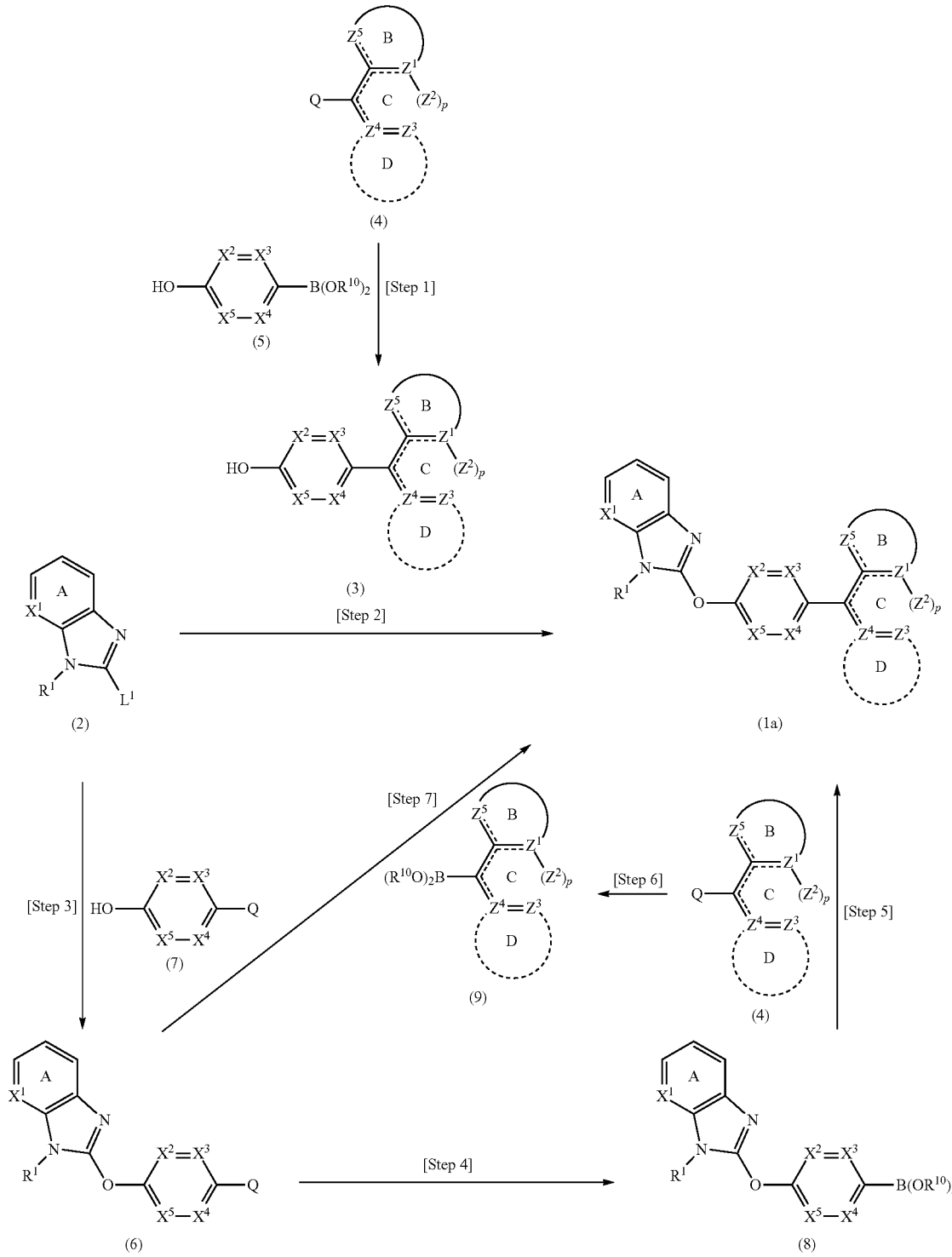

atom), optionally halogenated $C_{1-6}$ alkylsulfonyl group (e.g., methanesulfonyl, 2,2,2-trifluoroethylsulfonyl), optionally halogenated $C_{1-6}$ alkylsulfonyloxy group (e.g., methylsulfonyloxy, ethylsulfonyloxy, trifluoromethylsulfonyloxy), $C_{6-10}$ arylsulfonyloxy group (e.g., benzenesulfonyloxy, p-toluenesulfonyloxy) optionally substituted by a $C_{1-6}$ alkyl group, and the like, with preference given to halogen atom and methanesulfonyl group.

Compounds (2), (4), (5) and (7) are commercially available or can be produced according to a method known per se or a method analogous thereto.

[Step 1]

Compound (3) can be produced by reacting compound (4) with compound (5). Compound (5) is generally used in about 0.1-10 mol, preferably 0.2-5 mol, per 1 mol of compound (4).

This reaction is generally performed in the presence of a palladium catalyst and a base. Examples of the palladium catalyst include tetrakis(triphenylphosphine)palladium(0), dichlorobis(triphenylphosphine)palladium(II), palladium acetate(II) and the like. These palladium catalysts are generally used in about 0.001-1 mol, preferably 0.01-0.1 mol, per 1 mol of compound (4). Examples of the base include inorganic bases, basic salts, metal alkoxides and the like. These bases are generally used in about 1-10 mol, preferably 2-5 mol, per 1 mol of compound (4).

This reaction can be performed by adding a phosphine ligand when desired. Examples of the phosphine ligand include tri-tert-butylphosphine, 2-(di-tert-butylphosphine) biphenyl, 2-(dicyclohexylphosphino)biphenyl, triphenylphosphine and the like. These phosphine ligands are generally used in about 2 mol per 1 mol of a palladium catalyst.

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, water and the like or a mixed solvent thereof and the like are preferable.

While the reaction time varies depending on the reagent and solvent to be used, it is generally 0.5-72 hr, preferably 1-24 hr. The reaction temperature is generally −20-300° C., preferably 0-150° C. In addition, microwave irradiation may be performed to promote the reaction.

[Step 2]

Compound (1a) can be produced by reacting compound (2) with compound (3). Compound (3) is generally used in about 0.2-20 mol, preferably 1.0-5 mol, per 1 mol of compound (2).

This reaction is generally performed in the presence of a base. Examples of the base include inorganic bases, basic salts, organic bases, metal alkoxides, alkali metal hydrides, metal amides, alkylmetals, tertiary amines and the like. The base is generally used in about 0.1-20 mol, preferably 1.0-3 mol, per 1 mol of compound (2).

This reaction is advantageously performed in a solvent inert to the reaction. Such solvent is not particularly limited as long as the reaction proceeds and, for example, alcohols, ethers, hydrocarbons, amides, halogenated hydrocarbons, nitriles, ketones, esters, sulfoxides, water and the like solvent or thereof mixed solvent and the like preferable.

While the reaction time varies depending on the reagent and solvent to be used, it is generally 0.5-72 hr, preferably 1-24 hr. The reaction temperature is generally 0-300° C., preferably 0-150° C. In addition, microwave irradiation may be performed to promote the reaction.

[Step 3]

Compound (6) can be produced by reacting compound (2) with compound (7). This reaction can be performed according to a method similar to that in step 2.

[Step 4]

Compound (8) can be produced by reacting compound (6) with bis(pinacolato)diboron or boronic acid ester.

Bis(pinacolato)diboron or boronic acid ester is generally used in about 1-10 mol, preferably 1-5 mol, per 1 mol of compound (6).

When bis(pinacolato)diboron is used, this reaction is generally performed in the presence of a palladium catalyst and a base. Examples of the palladium catalyst include [1,1'-bis(diphenylphosphino)ferrocene]dichloropalladium(II), dichlorobis(triphenylphosphine)palladium(II), tetrakis(triphenylphosphine)palladium(0), palladium acetate(II) and the like. These palladium catalysts are generally used in about 0.001-1 mol, preferably 0.01-0.1 mol, per 1 mol of compound (6). Examples of the base include inorganic bases, basic salts, metal alkoxides and the like. These bases are generally used in about 1-10 mol, preferably 2-5 mol, per 1 mol of compound (6).

This reaction can be performed by adding a phosphine ligand when desired. Examples of the phosphine ligand include tri-tert-butylphosphine, 2-(di-tert-butylphosphine) biphenyl, 2-(dicyclohexylphosphino)biphenyl, triphenylphosphine and the like. These phosphine ligands are generally used in about 2 mol, per 1 mol of a palladium catalyst.

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, water and the like or a mixed solvent thereof and the like are preferable.

While the reaction time varies depending on the reagent and solvent to be used, it is generally 0.5-72 hr, preferably 1-24 hr. The reaction temperature is generally 0-200° C., preferably 20-100° C.

When boronic acid ester is used, this reaction is generally performed in the presence of an alkyl metal or aryl metal. These alkyl metals are generally used in about 1-10 mol, preferably 1-5 mol, per 1 mol of compound (6).

This reaction is advantageously performed in a solvent inert to the reaction. Such solvent is not particularly limited as long as the reaction proceeds and, for example, solvents such as ethers, hydrocarbons and the like or a mixed solvent thereof and the like are preferable.

While the reaction time varies depending on the reagent and solvent to be used, it is generally 0.5-24 hr, preferably 0.5-4 hr. The reaction temperature is generally −100 to 100° C., preferably −80 to 40° C.

[Step 5]

Compound (1a) can also be produced by reacting compound (8) with compound (4). This reaction can be performed according to a method similar to that in step 1.

[Step 6]

Compound (9) can be produced by reacting compound (4) with bis(pinacolato)diboron or boronic acid ester. This reaction can be performed according to a method similar to that in step 4.

[Step 7]

Compound (1a) can also be produced by reacting compound (9) with compound (6). This reaction can be performed according to a method similar to that in step 1.

[Production method B]

In compound (I), a compound wherein Y is a nitrogen atom (hereinafter to be referred to as compound (1b)) can be produced by, for example, the method shown in the following reaction scheme or a method analogous thereto.

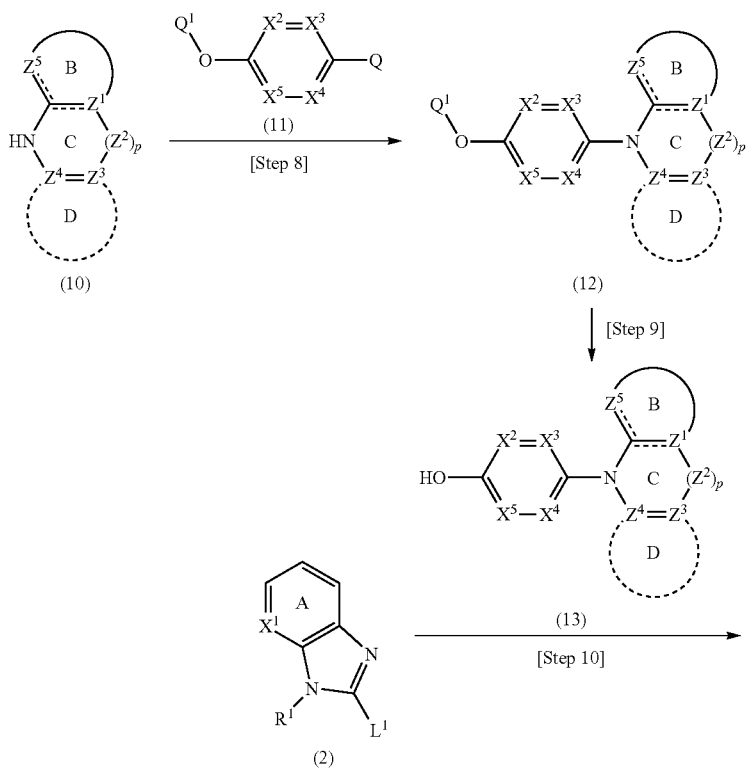

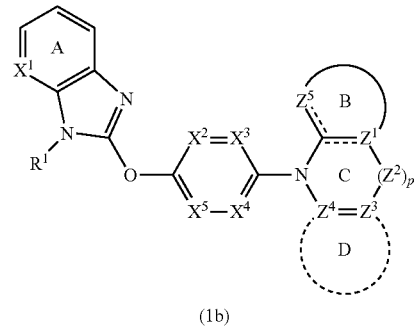

Wherein $Q^1$ is a protective group, and other symbols are as defined above.

Examples of the protective group for $Q^1$ include hydroxyl-protective groups used generally, and benzyl group and methyl group are particularly preferable.

Compounds (2), (10), (11) and (12) are commercially available or can be produced according to a method known per se or a method analogous thereto.

[Step 8]

Compound (12) can be produced by reacting compound (10) with compound (11). Compound (11) is generally used in about 0.1-10 mol, preferably 0.2-5 mol, per 1 mol of compound (10).

This reaction is generally performed in the presence of a palladium catalyst and a base. Examples of the palladium catalyst include tris(dibenzylideneacetone)dipalladium(0), dichlorobis(triphenylphosphine)palladium(II), palladium acetate(II) and the like. These palladium catalysts are generally used in about 0.001-1 mol, preferably 0.01-0.1 mol, per 1 mol of compound (10). Examples of the base include inorganic bases, basic salts, metal alkoxides and the like. These bases are generally used in about 1-10 mol, preferably 2-5 mol, per 1 mol of compound (10).

This reaction can be performed by adding a phosphine ligand when desired. Examples of the phosphine ligand include 4,5-bis(diphenylphosphino)-9,9-dimethylxanthene, dicyclohexyl [2',4',6'-tris(1-methylethyl)biphenyl-2-yl] phosphine and the like. These phosphine ligands are generally used in about 2 mol, per 1 mol of a palladium catalyst. For example, when tris(dibenzylideneacetone)dipalladium(0) is used as a palladium catalyst, the phosphine ligand is generally used in about 4 mol, per 1 mol of a palladium catalyst.

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, water and the like or a mixed solvent thereof and the like are preferable.

While the reaction time varies depending on the reagent and solvent to be used, it is generally 0.5-72 hr, preferably 1-24 hr. The reaction temperature is generally −20-300° C., preferably 0-150° C. In addition, microwave irradiation may be performed to promote the reaction.

[Step 9]

Compound (13) can be produced by removing the protective group of compound (12). The protective group can be removed according to a method known per se, for example, the method described in "Protective Groups in Organic Synthesis, $3^{rd}$ Ed." by Theodora W. Greene, Peter G. M. Wuts, Wiley-Interscience Corporation (1999), and the like.

[Step 10]

Compound (1b) can be produced by reacting compound (2) with compound (13). This reaction can be performed according to a method similar to that in step 2.

Since the compound of the present invention has a superior PDE10A inhibitory action, and shows low toxicity (e.g., phototoxicity, acute toxicity, chronic toxicity, genetic toxicity, reproductive toxicity, cardiotoxicity, drug interaction, carcinogenicity, etc., particularly phototoxicity), superior stability (particularly, metabolic stability) and superior in vivo kinetics (absorbability, distribution, metabolism, excretion etc.), and further, high solubility, it is useful as a pharmaceutical product. The compound of the present invention has a PDE10A inhibitory action on mammals (e.g., mouse, rat, hamster, rabbit, cat, dog, bovine, horse, sheep, monkey, human etc.), and can be used as a prophylactic or therapeutic drug for the following diseases and symptoms:

(1) psychotic disorder (e.g., brief psychotic disorder, shared psychotic disorder), (2) psychosis induced by alcohol, amphetamine, cannabis, cocaine, hallucinogens, obesity, inhalants, opioids, or phencyclidine,
(3) delusional disorder,
(4) anxiety disorder,
(5) movement disorder,
(6) mood disorder,
(7) major depressive disorder,
(8) major depressive disorder superimposed on a psychotic disorder comprising a delusional disorder or schizophrenia,
(9) major depression episode of mild, moderate or severe type,
(10) manic or mixed mood episode,
(11) hypomanic mood episode,
(12) depressive episode with atypical features,
(13) depressive episode with melancholic features,
(14) depressive episode with catatonic features,
(15) mood episode with postpartum onset,
(16) post-stroke depression,
(17) dysthymic disorder,
(18) minor depressive disorder,
(19) autism,
(20) drug addiction,
(21) neurodegenerative disease,
(22) neurodegeneration associated with brain trauma,
(23) neurodegeneration associated with cerebral stroke,
(24) neurodegeneration associated with cerebral infarction,
(25) neurodegeneration associated with epilepsy seizure,
(26) neurodegeneration associated with neurotoxin poisoning,
(27) multi-system atrophy,
(28) Alzheimer's disease,
(29) dementia,
(30) multi-infarct dementia,
(31) alcoholic dementia or other drug-related dementia,
(32) dementia associated with intracranial tumor or cerebrum trauma,
(33) dementia associated with Huntington's disease or Parkinson's disease,
(34) AIDS-related dementia,
(35) fronto temporal dementia,
(36) delirium,
(37) amnestic disorder,
(38) post-traumatic stress disorder,
(39) mental retardation,
(40) learning disorder (e.g., reading disorder, mathematics disorder, or a disorder of written expression),
(41) attention-deficit/hyperactivity disorder,
(42) age-related cognitive decline,
(43) premenstrual dysphoric disorder,
(44) post-psychotic depressive disorder of schizophrenia,
(45) bipolar disorders comprising bipolar I disorder and bipolar II disorder,
(46) cyclothymic disorder,
(47) Parkinson's disease,
(48) Huntington's disease,
(49) paranoid,
(50) schizophrenia (e.g., paranoid schizophrenia, disorganized schizophrenia, catatonic schizophrenia, undifferentiated schizophrenia, residual schizophrenia),
(51) schizophreniform disorder,
(52) schizoaffective disorder of the delusional type,
(53) personality disorder of the paranoid type,
(54) personality disorder of the schizoid type,
(55) obesity,
(56) metabolic syndrome,
(57) non-insulin dependent diabetes,
(58) glucose intolerance.

Particularly, the compound of the present invention is useful for the prophylaxis or treatment of schizophrenia.

Since the compound of the present invention is superior in the metabolic stability, it is predicted to show a superior therapeutic effect for the above-mentioned diseases even at a low dosage.

Since the compound of the present invention has low toxicity, a pharmaceutical composition containing the compound of the present invention (hereinafter to be referred to as "the medicament of the present invention") can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablets (inclusive of sugar-coated tablet, film-coated tablet, sublingual tablet, orally disintegrable tablet, buccal, etc.), pills, powders, granules, capsules (inclusive of soft capsule, and microcapsule), troches, syrups, liquids, emulsions, suspensions, controlled-release preparations (e.g., quick-release preparation, sustained-release preparation, sustained-release microcapsule), aerosols, films (e.g., orally disintegrable film, adhesive film for application to the oral cavity mucosa), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, orally or parenterally (e.g., intravenous, intramuscular, subcutaneous, intraorgan, intranasal, intradermal, ophthalmic instillation, intracerebral, intrarectal, intravaginal, intraperitoneal, intratumor, the vicinity of tumor, and the lesion).

As the above-mentioned pharmacologically acceptable carriers, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonic agent, buffer and soothing agent for liquid preparations, and where necessary, conventional preservative, antioxidant, colorant, sweetening agent, adsorbent, wetting agent and the like can be used as appropriate in an appropriate amount.

Examples of the vehicles are as follows: lactose, sucrose, D-mannitol, D-sorbitol, starch, α-starch, cornstarch, dextrin, crystalline cellulose, low-substituted hydroxypropyl cellulose, sodium carboxymethylcellulose, gum Arabic, pullulan, light anhydrous silicic acid, synthetic aluminum silicate, magnesium metasilicic aluminate and the like.

Examples of the lubricants include magnesium stearate, calcium stearate, talc, colloidal silica and the like.

Examples of the binder include α-starch, crystalline cellulose, sucrose, gum arabic, D-mannitol, trehalose, dextrin, pullulan, hydroxypropylcellulose, hydroxypropylmethylcellulose, polyvinylpyrrolidone, starch, sucrose, gelatin, methylcellulose, carboxymethylcellulose, sodium carboxymethylcellulose and the like.

Examples of the disintegrants include lactose, sucrose, starch, carboxymethylcellulose, calcium carboxymethylcellulose, croscarmellose sodium, sodium carboxymethyl starch, light anhydrous silicic acid, low-substituted hydroxypropylcellulose and the like.

Examples of the solvent include water for injection, saline, Ringer's solution, alcohol, propylene glycol, polyethylene glycol, macrogol, sesame oil, corn oil, olive oil, cottonseed oil and the like.

Examples of the solubilizing agents include polyethylene glycol, propylene glycol, D-mannitol, trehalose, benzyl benzoate, ethanol, tris-aminomethane, cholesterol, triethanolamine, sodium carbonate, sodium citrate, sodium salicylate, sodium acetate and the like.

Examples of the suspending agents include surfactants such as stearyltriethanolamine, sodium lauryl sulfate, lauryl aminopropionate, lecithin, benzalkonium chloride, benzethonium chloride, glyceryl monostearate, and the like; for example, hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, polysorbate, polyoxyethylene hydrogenated castor oil etc., and the like.

Examples of the isotonic agent include glucose, D-sorbitol, sodium chloride, glycerol, D-mannitol and the like.

Examples of the buffer include buffer solutions of phosphates, acetates, carbonates, citrates and the like.

Favorable examples of the soothing agents include benzyl alcohol and the like.

Favorable examples of antiseptics include para-oxybenzoic acid esters, chlorobutanol, benzyl alcohol, phenethyl alcohol, dehydroacetic acid and sorbic acid.

Examples of the antioxidant include sulfite, ascorbic acid, α-tocopherol and the like.

Examples of the colorants include water soluble edible tar dyes (e.g., Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, ferric oxide red), and the like.

Examples of the sweeteners include sodium saccharin, dipotassium glycyrrhizate, aspartame, stevia and the like.

The content of the compound of the present invention in the medicament of the present invention varies based on the dosage forms, dosages of the compound of the present invention, etc. For example, it is about 0.01-100 wt %, preferably about 0.1-95 wt %, of the whole medicament.

The dosage of the compound of the present invention depends upon injection targets, administration routes, target diseases, symptoms, etc. For example, in the case of oral administration in patients with schizophrenia (adults, body-weight of about 60 kg), generally a single dose ranges from about 0.1 to about 20 mg/kg bodyweight, preferably from about 0.2 to about 10 mg/kg bodyweight, further preferably from about 0.5 to about 10 mg/kg bodyweight, and this dosage is preferably administered according to symptom once daily or several times daily (e.g., 1-3 times).

The compound of the present invention can be administered as the sole active agent or in combination with other pharmaceutical products such as other drugs used for the treatment of psychosis, especially schizophrenia and bipolar disorder, obsessive-compulsive disorder, major depression, Parkinson's disease, Alzheimer's disease, cognitive impairment, memory loss and the like (hereinafter sometimes to be referred to as "concomitant drug").

In the following, a combined use of the compound of the present invention and a concomitant drug is to be referred to as "concomitant agent of the present invention".

Examples of the concomitant drug include nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigmine, and galanthamine) and the like.

Examples of the concomitant drug include, but are not limited to, other suitable schizophrenia drugs (e.g., haloperidol, clozapine, olanzapine, risperidone, aripiprazole, ziprasidone, paliperidone, quetiapine fumarate, etc.); bipolar disorder drugs (e.g., lithium, olanzapine, aripiprazole, valproic acid, etc.); Parkinson's disease drugs (e.g., levodopa, bromocriptine, pergolide, pramipexole, tolcapone, procyclidine, trihexyphenidyl, benztropine, etc.); agents used in the treatment of major depression (e.g., amitriptyline, protriptyline, desipramine, nortriptyline, paroxetine, fluoxetine, sertraline, bupropion, escitalopram, mirtazapine, venlafaxine, duloxetine, etc.); agents used in the treatment of Alzheimer's disease (e.g., galanthamine, tacrine, donepezil, rivastigmine, memantine, neotropin, selegiline, estrogen, iodoquinol, etc.); agents used in the treatment of dementia (e.g., thioridazine, haloperidol, risperidone, tacrine, donepezil, rivastigmine, etc.); agents used in the treatment of epilepsy (e.g., phenyloin, phenobarbital, carbamazepine, valproic acid, ethosuximide, gabapentin, phenobarbital, solfeton, felbatol, etc.); therapeutic agents for multiple sclerosis (e.g., tolterodine, oxybutynin, oxycodone, interferon β-1b, interferon β-1a, azathioprine, methotrexate, glatiramer, etc.); therapeutic agents for Huntington's disease (e.g., amitriptyline, protriptyline, desipramine, nortriptyline, paroxetine, fluoxetine, sertraline, tetrabenazine, haloperidol, chlorpromazine, thioridazine, sulpiride, quetiapine, clozapine, risperidone, etc.); therapeutic agents for diabetes (e.g., PPAR ligands (e.g., agonists, antagonists, such as rosiglitazone, troglitazone, etc.), insulin secretagogues (e.g., sulfonylurea drugs such as glyburide, glimepiride, chlorpropamide, tolbutamide and glipizide; non-sulfonyl secretagogues, and the like), α-glucosidase inhibitors (e.g., acarbose, miglitol, and voglibose), insulin sensitizers (e.g., the PPAR-γ agonists such as glitazones; biguanides, PTP-1B inhibitors, DPP-IV inhibitors, 11β-HSD inhibitors and the like), hepatic glucose output lowering compounds (e.g., glucagon antagonists; metformin such as Glucophage and Glucophage XR), insulin and insulin derivatives (both long and short acting forms and formulations of insulin); antiobesity drugs [e.g., β-3 agonists, CB-1 agonists, neuropeptide Y5 inhibitors, ciliary neurotrophic factor and derivatives (e.g., axokine), appetite suppressants (e.g., sibutramine), lipase inhibitors (e.g., orlistat), and the like]; and the like.

When using the concomitant agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The form of administration of concomitant drugs of the present invention is not particularly limited and is acceptable as long as the compound of the present invention is combined with concomitant drugs at the time of administration. Examples of such forms of administration are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order, etc.) and the like.

For example, when a concomitant drug or a pharmaceutical composition thereof is administered first, the compound of the present invention or a pharmaceutical composition thereof can be administered within 1 min to 3 days, preferably within 10 min to 1 day and more preferably within 15 min to 1 hr after the concomitant drug or a pharmaceutical composition thereof is administered. On the other hand, when the compound of the present invention or a pharmaceutical composition thereof is administered first, a concomitant drug or a pharmaceutical composition thereof can be administered within 1 min to 1 day, preferably within 10 min to 6 hr and more preferably within 15 min to 1 hr after the compound of the present invention or a pharmaceutical composition thereof is administered.

When there are no problems with side effects of the concomitant drugs, any dosages can be set. A dosage as a concomitant drug depends upon dosage form, administration subject, administration route, target disease, symptom, etc. For example, in the case of oral administration in patients with schizophrenia (adults, bodyweight of approximately 60 kg), a normal dosage ranges from about 0.1 to about 20 mg/kg bodyweight, preferably from about 0.2 to about 10 mg/kg bodyweight and more preferably from about 0.5 to about 10 mg/kg bodyweight. It is desirable that this dosage is administered once daily to several times daily (e.g., 1-3 times) according to the symptoms.

By combining the compound of the present invention and a concomitant drug, a superior effect such as
(1) the dose can be reduced as compared to single administration of the compound of the present invention, or a concomitant drug,
(2) the concomitant drug can be selected according to the condition of patients (mild case, severe case and the like),
(3) the period of treatment can be set longer by selecting a concomitant drug having different action mechanism from the compound of the present invention,
(4) a sustained treatment effect can be designed by selecting a concomitant drug having different action mechanism from the compound of the present invention,
(5) a synergistic effect can be afforded by a combined use of the compound of the present invention, and a concomitant drug, and the like, can be achieved.

The concomitant agent of the present invention has low toxicity, and for example, the compound of the present invention, and/or the above-mentioned concomitant drug can be mixed, according to a method known per se, with a pharmacologically acceptable carrier to prepare pharmaceutical compositions, such as tablets (including sugar-coated tablet, film-coated tablet and the like), powders, granules, capsules (including soft capsules), solutions, emulsions, suspensions, injections, suppositories, sustained release preparations (e.g., sublingual tablet, microcapsule etc.), patches, orally disintegrating tablets, orally disintegrating films and the like, which can be safely administered orally or parenterally (e.g., subcutaneous, topical, rectal, intravenous administrations etc.).

Examples of the pharmacologically acceptable carriers usable for the production of the concomitant agent of the present invention include those recited above as usable for the production of the medicament of the present invention.

The combination ratio of the compound of the present invention to the concomitant drug in the concomitant agent of the present invention can be appropriately selected depending on an administration subject, administration route, target diseases and the like.

Two or more kinds of the concomitant drug in the concomitant agent of the present invention can be combined as appropriate where necessary.

For example, the content of the compound of the present invention in the concomitant agent of the present invention varies with the drug form of formulations. Generally, it is present from about 0.01 to 99.9 wt %, preferably from about 0.1 to about 50 wt % and more preferably from about 0.5 to about 20 wt % relative to the entire formula.

The content of a concomitant drug in the concomitant agent of the present invention varies with the drug form of formulations. Generally it is present from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the drug 0.15 form of formulations. Generally it is present from about 1 to 99.99 wt % and preferably from about 10 to 90 wt % relative to the entire formula.

When the compound of the present invention and a concomitant drug are formulated independently, the same contents can be applied.

EXAMPLES

The present invention is explained in detail by referring to the following Reference Examples, Examples, Formulation Examples, and Experimental Examples. These examples are mere embodiments, which do not limit the present invention, and can be modified within the range not deviating from the scope of the present invention.

The "room temperature" in the following Reference Examples and Examples is generally about 10° C. to about 35° C. in the yield means mol/mol %, % of solvent used for chromatography means % by volume, and % used for others means wt %. In proton NMR spectrum, OH and NH protons and the like that cannot be identified since they are broad bands are not recorded in the data. In silica gel chromatography, Kieselgel 60 manufactured by Merck & Co., Inc. was used, and Chromatorex NH manufactured by Fuji Silysia Chemical Ltd. was used in basic silica gel chromatography.

Other abbreviations used in the text mean the following.
DIAD: diisopropyl azodicarboxylate
DME: dimethoxyethane
DMA: dimethylacetamide
DMF: N,N-dimethylformamide
THF: tetrahydrofuran
DMSO: dimethyl sulfoxide
HOBt: 1-hydroxybenzotriazole
EDCI: 1-(3-dimethylaminopropyl)-3-ethylcarbodiimide•hydrochloride LC-MS: liquid chromatography-mass spectrometry spectrum
ESI: electrospray ionization method
API: atmospheric chemical ionization method Example 1

2-[4-(2-Methylimidazo[1,2-a]pyridin-8-yl)phenoxy]-1H-benzimidazole

A) 2-Chloro-1-{[2-(trimethylsilyl)ethoxy]methyl}-1H-benzimidazole

To a solution of 2-chloro-1H-benzimidazole (3.8 g) in DMF (25 ml) was added sodium hydride (60% in oil, 1.1 g) at 0° C. in several portions. The reaction mixture was stirred at 0° C. for 30 min, 2-(trimethylsilyl)ethoxymethyl chloride (4.7 ml) was added dropwise, and the mixture was stirred at room temperature overnight. The reaction mixture was poured into water, and the mixture was extracted with ethyl acetate. The extract was washed with saturated brine, dried over anhydrous magnesium sulfate and the solvent was evaporated under reduced pressure. The residue was purified by basic silica gel column chromatography (hexane/ethyl acetate) to give the title compound (6.3 g).
$^1$H NMR (300 MHz, CDCl$_3$) 5-0.05 (9H, s), 0.87-0.95 (2H, m), 3.55-3.61 (2H, m), 5.57 (2H, s), 7.27-7.36 (2H, m), 7.42-7.50 (1H, m), 7.66-7.74 (1H, m).

B) 4-(2-Methylimidazo[1,2-a]pyridin-8-yl)phenol

A mixture of 4-hydroxyphenylboronic acid (1.1 g), 8-bromo-2-methylimidazo[1,2-a]pyridine (1.7 g), tetrakis(triphenylphosphine)palladium(0) (0.28 g), sodium carbonate (3.0 g), DME (35 ml) and water (7 ml) was heated under reflux overnight under an argon atmosphere. The reaction mixture was poured into water, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) and recrystallized from ethyl acetate to give the title compound (0.46 g).
MS (ESI+): [M+H]$^+$ 225.2.
$^1$H NMR (300 MHz, DMSO-d$_6$) δ 2.35 (3H, s), 6.81-6.92 (3H, m), 7.29 (1H, dd, J=7.2, 1.1 Hz), 7.68-7.75 (1H, m), 7.94-8.03 (2H, m), 8.38 (1H, dd, J=6.6, 1.3 Hz), 9.60 (1H, s).

C) 2-[4-(2-Methylimidazo[1,2-a]pyridin-8-yl)phenoxy]-1-{[2-(trimethylsilyl)ethoxy]methyl)-1H-benzimidazole To a solution of 4-(2-methylimidazo[1,2-a]pyridin-8-yl)phenol (0.40 g) in DMF (5 ml) was added sodium hydride (60% in oil, 0.086 g), and the mixture was stirred at room temperature for 5 min. To the reaction mixture was added 2-chloro-1-{[2-(trimethylsilyl)ethoxy]methyl}-1H-benzimidazole (0.50 g), and the mixture was stirred under microwave irradiation at 150° C. for 1 hr. The reaction mixture was poured into water, and the mixture was extracted with ethyl acetate. The extract was washed with saturated brine, dried over anhydrous sodium sulfate, and the solvent was evaporated under reduced pressure. The residue was purified by basic silica gel column chromatography (hexane/ethyl acetate) to give the title compound (0.57 g).
MS (API+): [M+H]$^+$ 471.4.
$^1$H NMR (300 MHz, CDCl$_3$) δ −0.02 (9H, s), 0.91-1.02 (2H, m), 2.49 (3H, s), 3.64-3.74 (2H, m), 5.58 (2H, s), 6.77-6.85 (1H, m), 7.19-7.25 (3H, m), 7.38-7.45 (2H, m), 7.45-7.51 (2H, m), 7.56-7.62 (1H, m), 8.04 (1H, dd, J=6.6, 1.3 Hz), 8.06-8.13 (2H, m).

D) 2-[4-(2-Methylimidazo[1,2-a]pyridin-8-yl)phenoxy]-1H-benzimidazole

A mixture of 2-[4-(2-methylimidazo[1,2-a]pyridin-8-yl)phenoxy]-1-{[2-(trimethylsilyl)ethoxy]methyl}-1H-benzimidazole (0.57 g) and 4 M hydrogen chloride-ethyl acetate solution (20 ml) was heated under reflux for 3 hr. The reaction mixture was concentrated under reduced pressure, saturated aqueous sodium hydrogen carbonate solution was added to the residue, and the mixture was extracted with ethyl acetate. The extract was dried over anhydrous sodium sulfate, and the solvent was evaporated under reduced pressure. The residue was recrystallized from ethyl acetate to give the title compound (0.35 g).
MS (API+): [M+H]$^+$ 341.0.
$^1$H NMR (300 MHz, DMSO-d$_6$) δ 2.38 (3H, s), 6.91-6.98 (1H, m), 7.07-7.15 (2H, m), 7.33-7.41 (2H, m), 7.43 (1H, dd, J=7.2, 1.1 Hz), 7.47-7.54 (2H, m), 7.76-7.80 (1H, m), 8.17-8.24 (2H, m), 8.48 (1H, dd, J=6.4, 1.1 Hz), 12.39 (1H, brs).

Example 2

2-[4-(Imidazo[1,2-a]pyridin-8-yl)phenoxy]-1H-benzimidazole

A) 4-(Imidazo[1,2-a]pyridin-8-yl)phenol

A mixture of 4-hydroxyphenylboronic acid (0.77 g), 8-bromoimidazo[1,2-a]pyridine (1.1 g), tetrakis(triphenylphosphine)palladium(0) (0.19 g), sodium carbonate (2.1 g), DME (30 ml) and water (6 ml) was heated under reflux overnight under an argon atmosphere. The reaction mixture was poured into water, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) and recrystallized from ethyl acetate to give the title compound (0.88 g).
MS (API+): [M+H]$^+$ 211.1.
$^1$H NMR (300 MHz, CDCl$_3$) δ 6.64-6.72 (2H, m), 6.85-6.92 (1H, m), 7.18 (1H, dd, J=7.0, 1.3 Hz), 7.42-7.50 (2H, m), 7.66 (1H, d, J=1.1 Hz), 7.73 (1H, d, J=1.1 Hz), 8.10 (1H, dd, J=6.8, 1.1 Hz).

B) 2-[4-(Imidazo[1,2-a]pyridin-8-yl)phenoxy]-1-{[2-(trimethylsilyl)ethoxy]methyl}-1H-benzimidazole To a solution of 4-(imidazo[1,2-a]pyridin-8-yl)phenol (0.68 g) in DMF (10 ml) was added sodium hydride (60% in oil, 0.13 g), and the mixture was stirred at room temperature for 5 min. To the reaction mixture was added 2-chloro-1-{[2-(trimethylsilyl)ethoxy]methyl}-1H-benzimidazole (0.53 g) obtained in Example 1, step A), and the mixture was stirred under microwave irradiation at 150° C. for 1.5 hr. The reaction mixture was poured into water, and the mixture was extracted with ethyl acetate. The extract was washed with saturated brine, dried over anhydrous sodium sulfate, and the solvent was evaporated under reduced pressure. The residue was purified by silica gel column chromatography (hexane/ethyl acetate) to give the title compound (0.53 g).
MS (ESI+): [M+H]$^+$ 457.5.

¹H NMR (300 MHz, CDCl₃) δ −0.02 (9H, s), 0.92-1.01 (2H, m), 3.64-3.73 (2H, m), 5.58 (2H, s), 6.85-6.93 (1H, m), 7.19-7.25 (2H, m), 7.29 (1H, dd, J=6.8, 1.1 Hz), 7.37-7.45 (1H, m), 7.46-7.53 (2H, m), 7.55-7.62 (1H, m), 7.69 (2H, dd, J=13.0, 1.3 Hz), 8.07-8.17 (3H, m).

C) 2-[4-(Imidazo[1,2-a]pyridin-8-yl)phenoxy]-1H-benzimidazole

A mixture of 2-[4-(imidazo[1,2-a]pyridin-8-yl)phenoxy]-1-{[2-(trimethylsilyl)ethoxy]methyl}-1H-benzimidazole (0.53 g), 4 M hydrogen chloride-ethyl acetate solution (20 ml) and methanol (4 ml) was heated under reflux for 3 hr. The reaction mixture was concentrated under reduced pressure, saturated aqueous sodium hydrogen carbonate solution was added to the residue, and the mixture was extracted with ethyl acetate. The extract was dried over anhydrous sodium sulfate, and the solvent was evaporated under reduced pressure. The residue was recrystallized from ethyl acetate to give the title compound (0.29 g).

MS (API+): [M+H]⁺ 327.1.
¹H NMR (300 MHz, DMSO-d₆) δ 6.98-7.06 (1H, m), 7.07-7.17 (2H, m), 7.34-7.42 (2H, m), 7.47-7.55 (3H, m), 7.65 (1H, d, J=1.1 Hz), 8.06 (1H, d, J=1.1 Hz), 8.21-8.30 (2H, m), 8.59 (1H, dd, J=6.8, 1.1 Hz), 12.41 (1H, brs).

Example 3

3-[4-(1H-benzimidazol-2-yloxy)phenyl]-2-ethyl-2H-pyrazolo[4,3-b]pyridine

A) 3-Bromo-1H-pyrazolo[4,3-b]pyridine

A mixture of 3-fluoropyridine-2-carbaldehyde (5 g) and hydrazine monohydrate (15 ml) was stirred under reflux for 12 hr. After allowed to cool to room temperature, the solvent was evaporated under reduced pressure. The residue was dissolved in DMF (15 ml), and N-bromosuccinimide (7.47 g) was added under ice-cooling. The reaction mixture was stirred at room temperature for 2 days, and N-bromosuccinimide (7.47 g) was added at room temperature. The reaction mixture was stirred at room temperature for 2 hr, water was added, and the mixture was extracted with ethyl acetate. The extract was dried over anhydrous magnesium sulfate and the solvent was evaporated under reduced pressure. The residue was suspended in a mixed solvent of ethanol and diisopropylether, and the solid was collected by filtration to give the title compound (1.2 g). ¹H NMR (300 MHz, DMSO-d₆) δ 7.48 (1H, dd, J=8.5, 4.3 Hz), 8.07 (1H, dt, J=8.5, 1.3 Hz), 8.59 (1H, dd, J=4.3, 1.3 Hz), 13.69 (1H, brs).

B) 3-Bromo-2-ethyl-2H-pyrazolo[4,3-b]pyridine

To a solution of ethanol (0.118 ml) and triphenylphosphine (530 mg) in THF (3 ml) was added 3-bromo-1H-pyrazolo[4,3-b]pyridine (200 mg), and the mixture was heated at 50° C. A toluene solution (1.9 M, 1.06 ml) of DIAD was added dropwise at 50° C., and the mixture was stirred for 30 min. The reaction mixture was cooled to room temperature, water was added, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) to give the title compound (71 mg).

MS (API+): [M+H]⁺ 226.1.

¹H NMR (300 MHz, DMSO-d₆) δ 1.49 (3H, t, J=7.3 Hz), 4.55 (2H, q, J=7.2 Hz), 7.35 (1H, dd, J=8.9, 4.0 Hz), 8.13 (1H, dd, J=8.9, 1.5 Hz), 8.49-8.61 (1H, m).

C) 2-(4-Bromophenoxy)-1H-benzimidazole

A mixture of 2-chloro-1H-benzimidazole (5.6 g), 4-bromophenol (9.87 g) and triethylamine (19.89 ml) was stirred at 120° C. for 15 hr, and ethyl acetate was added. The reaction mixture was washed with 1 M aqueous sodium hydroxide solution and saturated brine, dried over anhydrous magnesium sulfate, and the solvent was evaporated under reduced pressure. A solid precipitated from the residue was collected by filtration to give the title compound (5.77 g).

MS (API+): [M+H]⁺ 289.0.
¹H NMR (300 MHz, CDCl₃) δ 7.15-7.23 (2H, m), 7.27-7.40 (3H, m), 7.48-7.66 (3H, m), 8.60 (1H, brs).

D) 2-[4-(4,4,5,5-Tetramethyl-1,3,2-dioxaborolan-2-yl)phenoxy]-1H-benzimidazole

A mixture of 2-(4-bromophenoxy)-1H-benzimidazole (6.69 g), bis(pinacolato)diboron (8.81 g), potassium acetate (6.81 g), 1,1'-bis(diphenylphosphino)ferrocene dichloropalladium(II) dichloromethane adduct (0.945 g) and THF/DMSO (20/1, 189 ml) was stirred under an argon atmosphere at 80° C. for 15 hr. Water was added to the reaction mixture, and the mixture was extracted with ethyl acetate. The extract was washed with saturated brine, dried over anhydrous magnesium sulfate, and the solvent was evaporated under reduced pressure. The residue was purified by silica gel chromatography (THF/hexane) to give the title compound (1.32 g).

MS (API+): [M+H]⁺ 337.1.
¹H NMR (300 MHz, DMSO-d₆) δ 1.31 (12H, s), 7.07-7.16 (2H, m), 7.33-7.43 (4H, m), 7.76 (2H, d, J=8.7 Hz), 12.41 (1H, brs).

E) 3-[4-(1H-benzimidazol-2-yloxy)phenyl]-2-ethyl-2H-pyrazolo[4,3-b]pyridine

A mixture of 2-[4-(4,4,5,5-tetramethyl-1,3,2-dioxaborolan-2-yl)phenoxy]-1H-benzimidazole (116 mg), 3-bromo-2-ethyl-2H-pyrazolo[4,3-b]pyridine (71 mg), tetrakis(triphenylphosphine)palladium(0) (36.3 mg), cesium carbonate (153 mg) and DME/water (3/1, 4 ml) was subjected to microwave irradiation at 120° C. for 40 min. Water was added to the reaction mixture, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) and recrystallized from ethyl acetate/hexane to give the title compound (66.0 mg).

MS (API+): [M+H]⁺ 356.2.
¹H NMR (300 MHz, DMSO-d₆) δ 1.53 (3H, t, J=7.2 Hz), 4.57 (2H, q, J=7.2 Hz), 7.05-7.23 (2H, m), 7.28-7.48 (3H, m), 7.59-7.67 (2H, m), 7.78-7.88 (2H, m), 8.14 (1H, d, J=7.6 Hz), 8.48-8.64 (1H, m), 12.47 (1H, s).

Example 4

2-Ethyl-3-{4-[(1-methyl-1H-benzimidazol-2-yl)oxy]phenyl}-2H-pyrazolo[4,3-b]pyridine A mixture of 3-[4-(1H-benzimidazol-2-yloxy)phenyl]-2-ethyl-2H-pyrazolo[4,3-b]pyridine (25 mg) obtained in Example 3, iodomethane (5.72 μl), cesium carbonate (34.4 mg) and DMF (1 ml) was stirred at room temperature for 2 hr. Water was added to the reaction mixture, and the mixture was extracted with ethyl acetate. The extract was washed with saturated brine, dried over anhydrous magnesium sulfate, and the solvent was evaporated under reduced pressure. The residue was purified by silica gel column chromatography (hexane/ethyl acetate) and recrystallized from ethyl acetate/hexane to give the title compound (24.0 mg).

MS (API+): [M+H]$^+$ 370.9.

$^1$H NMR (300 MHz, DMSO-$d_6$) δ 1.53 (3H, t, J=7.2 Hz), 3.78 (3H, s), 4.57 (2H, q, J=7.2 Hz), 7.11-7.26 (2H, m), 7.30-7.37 (1H, m), 7.42-7.55 (2H, m), 7.63-7.74 (2H, m), 7.80-7.90 (2H, m), 8.14 (1H, dd, J=8.7, 1.5 Hz), 8.50-8.59 (1H, m).

Example 5

2-[4-(5,6,7,8-Tetrahydroimidazo[1,2-a]pyridin-8-yl)phenoxy]-1H-benzimidazole

A) 4-(5,6,7,8-Tetrahydroimidazo[1,2-a]pyridin-8-yl)phenol

A mixture of 4-(imidazo[1,2-a]pyridin-8-yl)phenol (0.22 g), 10% palladium on carbon (containing water (50%), 0.10 g) and methanol (15 ml) was stirred under a hydrogen atmosphere at room temperature for 5 days. The reaction mixture was filtered, and the filtrate was concentrated under reduced pressure. The obtained solid was washed with ethyl acetate to give the title compound (0.14 g).

MS (API+): [M+H]$^+$ 215.2.

$^1$H NMR (300 MHz, DMSO-$d_6$) δ 1.75-1.97 (3H, m), 2.03-2.20 (1H, m), 3.93-4.08 (3H, m), 6.65 (2H, d, J=8.7 Hz), 6.80 (1H, d, J=1.1 Hz), 6.86 (2H, d, J=8.7 Hz), 7.02 (1H, d, J=1.1 Hz), 9.19 (1H, brs).

B) 2-[4-(5,6,7,8-Tetrahydroimidazo[1,2-a]pyridin-8-yl)phenoxy]-1-{[2-(trimethylsilyl)ethoxy]methyl}-1H-benzimidazole To a solution of 4-(5,6,7,8-tetrahydroimidazo[1,2-a]pyridin-8-yl)phenol (0.13 g) in DMF (10 ml) was added sodium hydride (60% in oil, 0.024 g), and the mixture was stirred at room temperature for 5 min. To the reaction mixture was added 2-chloro-1-{[2-(trimethylsilyl)ethoxy]methyl}-1H-benzimidazole (0.17 g) obtained in Example 1, step A), and the mixture was stirred under microwave irradiation at 150° C. for 1.5 hr. The reaction mixture was poured into water, and the mixture was extracted with ethyl acetate. The extract was washed with saturated brine, dried over anhydrous sodium sulfate, and the solvent was evaporated under reduced pressure. The residue was purified by basic silica gel column chromatography (hexane/ethyl acetate) to give the title compound (0.19 g).

MS (ESI+): [M+H]$^+$ 461.3.

C) 2-[4-(5,6,7,8-Tetrahydroimidazo[1,2-a]pyridin-8-yl)phenoxy]-1H-benzimidazole

2-[4-(5,6,7,8-Tetrahydroimidazo[1,2-a]pyridin-8-yl)phenoxy]-1-{[2-(trimethylsilyl)ethoxy]methyl}-1H-benzimidazole (0.19 g), 1.0 M tetrabutylammonium fluoride-THF solution (1.7 ml) and THF (3 ml) were stirred under microwave irradiation at 100° C. for 3 hr. The reaction mixture was stirred at 80° C. overnight, poured into water, and the mixture was extracted with ethyl acetate. The extract was washed with saturated brine, dried over anhydrous sodium sulfate, and the solvent was evaporated under reduced pressure. The residue was purified by basic silica gel column chromatography (hexane/ethyl acetate) and recrystallized from methanol/ethyl acetate to give the title compound (0.071 g).

MS (API+): [M+H]$^+$ 331.1.

$^1$H NMR (300 MHz, DMSO-$d_6$) δ 1.83-2.08 (3H, m), 2.14-2.31 (1H, m), 3.99-4.12 (2H, m), 4.14-4.26 (1H, m), 6.83 (1H, d, J=1.1 m Hz), 7.05-7.12 (3H, m), 7.15-7.21 (2H, m), 7.24-7.39 (4H, m), 12.31 (1H, brs).

Example 6

1-[4-(1H-benzimidazol-2-yloxy)phenyl]-3-methoxy-1H-pyrazolo[3,4-b]pyridine

A) N'-[4-(Benzyloxy)phenyl]-2-chloropyridine-3-carbohydrazide

To a solution of 2-chloropyridine-3-carboxylic acid (3.30 g) in DMF (50 ml) were added [4-(benzyloxy)phenyl]hydrazine (5.0 g), HOBt (3.7 g), EDCI (4.6 g) and diisopropylethylamine (9.0 g), and the mixture was stirred at room temperature for 12 hr. Water was added to the reaction mixture, and the mixture was extracted with ethyl acetate. The organic layers were combined, dried over anhydrous magnesium sulfate and filtered. The filtrate was concentrated under reduced pressure, and the obtained residue was purified by silica gel column chromatography (hexane/ethyl acetate) to give the title compound (5.0 g).

$^1$H NMR (400 MHz, CDCl$_3$) δ 5.01 (2H, s), 6.90-6.94 (4H, brs), 7.31-7.43 (7H, m), 8.11 (1H, dd, J=7.6, 2.0 Hz), 8.32-8.40 (1H, brs), 8.50 (1H, dd, J=4.6, 1.6 Hz)

B) 1-[4-(Benzyloxy)phenyl]-1,2-dihydro-3H-pyrazolo[3,4-b]pyridin-3-one

N'-[4-(benzyloxy)phenyl]-2-chloropyridine-3-carbohydrazide (5.0 g) was heated at 170° C. for 30 min without a solvent. The reaction mixture was cooled to room temperature, and purified by silica gel column chromatography (hexane/ethyl acetate) to give the title compound (2.0 g).

$^1$H NMR (400 MHz, CDCl$_3$) δ 1.25-1.95 (1H, brs), 5.13 (2H, s), 7.12-7.15 (3H, m), 7.35-7.38 (1H, m), 7.39-7.43 (2H, m), 7.46-7.50 (2H, m), 7.84-7.86 (2H, m), 8.17 (1H, dd, J=7.6, 1.6 Hz), 8.60 (1H, dd, J=6.4, 2.0 Hz).

C) 1-[4-(Benzyloxy)phenyl]-3-methoxy-1H-pyrazolo[3,4-b]pyridine

D) 1-[4-(Benzyloxy)phenyl]-2-methyl-1,2-dihydro-3H-pyrazolo[3,4-b]pyridin-3-one

To a solution of 1-[4-(benzyloxy)phenyl]-1,2-dihydro-3H-pyrazolo[3,4-b]pyridin-3-one (1.4 g) in DMF (50 ml) were added potassium carbonate (0.73 g) and iodomethane (0.75 g) at room temperature. The reaction mixture was stirred at room temperature for 2 hr, water was added, and the mixture was extracted with ethyl acetate. The organic layers were combined, dried over anhydrous magnesium sulfate and filtered. The filtrate was concentrated under reduced pressure, and the obtained residue was purified by silica gel column chromatography (hexane/ethyl acetate) to give 1-[4-(benzyloxy)phenyl]-3-methoxy-1H-pyrazolo[3,4-b]pyridine (1.1 g) and 1-[4-(benzyloxy)phenyl]-2-methyl-1,2-dihydro-3H-pyrazolo[3,4-b]pyridin-3-one (0.28 g).

1-[4-(benzyloxy)phenyl]-3-methoxy-1H-pyrazolo[3,4-b]pyridine $^1$H NMR (400 MHz, CDCl$_3$) δ 3.35 (3H, s), 5.10

(2H, s), 7.08-7.10 (2H, m), 7.15 (1H, dd, J=7.6, 4.8 Hz), 7.26-7.29 (2H, m), 7.35-7.45 (5H, m), 8.22 (1H, dd, J=7.6, 1.6 Hz), 8.53 (1H, dd, J=4.8, 1.6 Hz).

1-[4-(benzyloxy)phenyl]-2-methyl-1,2-dihydro-3H-pyrazolo[3,4-b]pyridin-3-one $^1$H NMR (400 MHz, CDCl$_3$) δ 4.16 (3H, s), 5.12 (2H, s), 7.07-7.11 (3H, m), 7.33-7.47 (5H, m), 8.02-8.08 (3H, m), 8.55 (1H, dd, =4.4, 1.6 Hz).

E) 4-(3-Methoxy-1H-pyrazolo[3,4-b]pyridin-1-yl)phenol

A suspension of 1-[4-(benzyloxy)phenyl]-3-methoxy-1H-pyrazolo[3,4-b]pyridine (1.1 g) and 10% palladium on carbon (containing water (50%), 0.10 g) in methanol (50 ml) was stirred for 3 hr under a hydrogen atmosphere at room temperature. The reaction mixture was filtered through celite, and the filtrate was purified by silica gel column chromatography (hexane/ethyl acetate) to give the title compound (0.50 g).
MS (API+): [M+H]$^+$ 242.1.
$^1$H NMR (400 MHz, CDCl$_3$) δ 4.16 (3H, s), 5.59 (1H, brs), 6.89-6.91 (2H, m), 7.11 (1H, dd, J=8.0, 4.8 Hz), 7.90-7.92 (2H, m), 8.06 (1H, dd, J=8.0, 1.6 Hz), 8.56 (1H, dd, J=4.4, 1.2 Hz).

F) 1-[4-(1H-benzimidazol-2-yloxy)phenyl]-3-methoxy-1H-pyrazolo[3,4-b]pyridine

A mixture of 2-chloro-1H-benzimidazole (0.23 g), 4-(3-methoxy-1H-pyrazolo[3,4-b]pyridin-1-yl)phenol (0.24 g) and triethylamine (1.0 ml) was stirred under a nitrogen atmosphere at 160° C. for 7 hr. The reaction mixture was cooled to room temperature, and methanol was added to the reaction mixture. The precipitated solid was filtered off, silica gel was added to the filtrate, the solvent was evaporated under reduced pressure, and the residue was purified by silica gel column chromatography (hexane/ethyl acetate). Then, it was purified by HPLC(C18) (mobile phase: water/acetonitrile (0.1% TFA-containing eluents)) to give the title compound (0.047 g).
MS (API+): [M+H]$^+$ 358.3.
$^1$H NMR (300 MHz, DMSO-d$_6$) δ 4.16 (3H, s), 7.07-7.19 (2H, m), 7.25-7.43 (3H, m), 7.47-7.63 (2H, m), 8.19-8.45 (3H, m), 8.68 (1H, dd, J=4.9, 1.9 Hz), 12.38 (1H, brs).

Example 7

1-[4-(1H-benzimidazol-2-yloxy)phenyl]-2-methyl-1,2-dihydro-3H-pyrazolo[3,4-b]pyridin-3-one A) 1-(4-Hydroxyphenyl)-2-methyl-1,2-dihydro-3H-pyrazolo[3,4-b]pyridin-3-one A mixture of 1-[4-(benzyloxy)phenyl]-2-methyl-1,2-dihydro-3H-pyrazolo[3,4-b]pyridin-3-one (0.28 g) obtained in Example 6, step D) and concentrated sulfuric acid (5.0 ml) was stirred at room temperature for 10 min. The obtained reaction mixture was diluted with water (10 ml), sodium hydroxide in m solid was added to pH 10, and the mixture was extracted with ethyl acetate. The organic layers were combined, dried over anhydrous magnesium sulfate, and the solvent was evaporated under reduced pressure. The obtained residue was purified by silica gel column chromatography (hexane/ethyl acetate) to give the title compound (0.15 g).
MS (API+): [M+H]$^+$ 242.1.

$^1$H NMR (400 MHz, CD$_3$OD) δ 3.67 (3H, s), 6.91-6.93 (2H, m), 7.17-7.19 (2H, m), 7.26 (1H, dd, J=8.0, 4.8 Hz), 8.25 (1H, dd, J=7.6, 1.2 Hz), 8.48 (1H, dd, J=4.8, 1.6 Hz).

B) 1-[4-(1H-benzimidazol-2-yloxy)phenyl]-2-methyl-1,2-dihydro-3H-pyrazolo[3,4-b]pyridin-3-one A mixture of 2-chloro-1H-benzimidazole (0.057 g), 1-(4-hydroxyphenyl)-2-methyl-1,2-dihydro-3H-pyrazolo[3,4-b]pyridin-3-one (0.060 g) and triethylamine (3.5 ml) was stirred under a nitrogen atmosphere at 160° C. for 16 hr. The reaction mixture was cooled to room temperature, diluted with methanol, and silica gel was added. The solvent was evaporated under reduced pressure, and the residue was purified by silica gel column chromatography (hexane/ethyl acetate) to give the title compound (0.012 g).
MS (API+): [M+H]$^+$ 358.3.
$^1$H NMR (300 MHz, DMSO-d$_6$) δ 3.19-3.32 (3H, m), 6.55 (2H, s), 6.82-6.94 (1H, m), 7.06-7.43 (4H, m), 7.49-7.81 (2H, m), 8.17-8.34 (1H, m), 8.48-8.67 (2H, m).

Example 8

3-Ethyl-1-{4-[(1-methyl-1H-benzimidazol-2-yl)oxy]phenyl}-1H-pyrazolo[3,4-b]pyridine A) 2-Chloro-N-methoxy-N-methylpyridine-3-carboxamide 2-Chloropyridine-3-carboxylic acid (13 g), N,O-dimethylhydroxylamine hydrochloride (8.85 g), HOBt (5.57 g), EDCI (15.37 g) and triethylamine (34.5 ml) were dissolved in DMF (150 ml), and the mixture was stirred at room temperature overnight. The reaction mixture was diluted with saturated aqueous sodium hydrogen carbonate solution, and extracted with ethyl acetate. The organic layer was washed successively with water and saturated brine, dried over anhydrous magnesium sulfate and concentrated under reduced pressure. The residue was purified by basic silica gel column chromatography (hexane/ethyl acetate) to give the title compound (10.5 g).
MS (API+): [M+H]$^+$ 201.0.
$^1$H NMR (300 MHz, DMSO-d$_6$) δ 3.33 (3H, s), 3.47 (3H, s), 7.45-7.63 (1H, m), 7.98-8.08 (1H, m), 8.44-8.55 (1H, m).

B) 1-(2-Chloropyridin-3-yl)propan-1-one

2-Chloro-N-methoxy-N-methylpyridine-3-carboxamide (1.0 g) was dissolved in THF (30 ml), 3 Methylmagnesium bromide-diethyl ether solution (2.0 ml) was added dropwise at room temperature, and the mixture was stirred at 50° C. for 1 hr. The reaction mixture was diluted with 1 M hydrochloric acid, and the mixture was extracted with ethyl acetate. The organic layer was washed successively with water and saturated brine, dried over anhydrous magnesium sulfate and concentrated under reduced pressure. The residue was purified by silica gel column chromatography (hexane/ethyl acetate) to give the title compound (630 mg).
MS (API+): [M+H]$^+$ 170.2.
$^1$H NMR (300 MHz, CDCl$_3$) δ 1.17-1.31 (3H, m), 2.93-3.09 (2H, m), 7.29-7.38 (1H, m), 7.75-7.88 (1H, m), 8.41-8.55 (1H, m).

C) 1-[4-(Benzyloxy)phenyl]-3-ethyl-1H-pyrazolo[3,4-b]pyridine 1-(2-Chloropyridin-3-yl)propan-1-one (600 mg) and [4-(benzyloxy)phenyl]hydrazine hydrochloride (976 mg) were dissolved in ethanol (10 ml), and the mixture was stirred under microwave irradiation at 170° C. for 3 hr, and concentrated. The residue was purified by basic silica gel column chromatography (hexane/ethyl acetate) to give the title compound (300 mg). MS (API+): [M+H]$^+$ 330.1.

$^1$H NMR (300 MHz, CDCl$_3$) δ 1.41-1.50 (3H, m), 3.01-3.12 (2H, m), 5.13 (2H, s), 7.05-7.19 (3H, m), 7.28-7.52 (5H, m), 7.94-8.16 (3H, m), 8.52-8.68 (1H, m).

D)
4-(3-Ethyl-1H-pyrazolo[3,4-b]pyridin-1-yl)phenol

A mixture of 1-[4-(benzyloxy)phenyl]-3-ethyl-1H-pyrazolo[3,4-b]pyridine (300 mg), 10% palladium on carbon (containing water (50%), 97 mg) and ethanol (10 ml) was vigorously stirred under a hydrogen atmosphere at room temperature for 5 hr. The reaction mixture was filtered and the filtrate was concentrated to give the title compound (200 mg).

MS (API+): [M+H]$^+$ 240.1.

$^1$H NMR (300 MHz, DMSO-d$_6$) δ 1.33-1.44 (3H, m), 2.94-3.09 (2H, m), 6.88-6.97 (2H, m), 7.23-7.34 (1H, m), 7.90-8.01 (2H, m), 8.30-8.41 (1H, m), 8.56-8.64 (1H, m), 9.58 (1H, s).

E) 3-Ethyl-1-{4-[(1-methyl-1H-benzimidazol-2-yl)oxy]phenyl}-1H-pyrazolo[3,4-b]pyridine To a mixture of 4-(3-ethyl-1H-pyrazolo[3,4-b]pyridin-1-yl)phenol (120 mg), sodium hydride (60% in oil, 21.0 mg) and DMF (5.0 ml) was added 2-chloro-1-methyl-1H-benzimidazole (84 mg), and the mixture was stirred under microwave irradiation at 180° C. for 1 hr. The reaction mixture was diluted with methanol, and concentrated under reduced pressure. The residue was purified by silica gel column chromatography (hexane/ethyl acetate) to give the title compound (100 mg).

MS (API+): [M+H]$^+$ 370.2.

$^1$H NMR (300 MHz, DMSO-d$_6$) δ 1.31-1.48 (3H, m), 3.01-3.15 (2H, m), 3.77 (3H, s), 7.08-7.26 (2H, m), 7.29-7.52 (3H, m), 7.55-7.72 (2H, m), 8.27-8.52 (3H, m), 8.56-8.76 (1H, m).

Example 9

9-{4-[(1-Methyl-1H-benzimidazol-2-yl)oxy]phenyl}-9H-imidazo[1',2':1,2]imidazo[4,5-b]pyridine

A) 3-[4-(Benzyloxy)phenyl]-3H-imidazo[4,5-b]pyridin-2-amine

A mixture of N$^2$-[4-(benzyloxy)phenyl]pyridine-2,3-diamine (3.96 g), cyanogen bromide (2.88 g), THF (60 mL) and water (15 mL) was stirred at room temperature for 48 hr. The reaction mixture was poured into saturated aqueous sodium hydrogen carbonate solution, and the mixture was extracted with ethyl acetate. The extract was washed with saturated brine, dried over magnesium sulfate, and the solvent was evaporated under reduced pressure. The residue was purified by silica gel column chromatography (hexane/tetrahydrofuran), treated with activated carbon, and recrystallized from methanol/water to give the title compound (1.16 g).

MS (API+): [M+H]$^+$ 317.2.

B) 9-[4-(Benzyloxy)phenyl]-9H-imidazo[1',2':1,2]imidazo[4,5-b]pyridine

A solution of 3-[4-(benzyloxy)phenyl]-3H-imidazo[4,5-b]pyridin-2-amine (1.58 g) and 6.1 M aqueous chloroacetoaldehyde solution (1.64 mL) in DMA (20 mL) was stirred at 90° C. for 1.5 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (hexane/ethyl acetate) and recrystallized from hexane/THF to give the title compound (0.665 g).

MS (API+): [M+H]$^+$ 341.2.

C) 4-(9H-imidazo[1',2':1,2]imidazo[4,5-b]pyridin-9-yl)phenol

A mixture of 9-[4-(benzyloxy)phenyl]-9H-imidazo[1',2':1,2]imidazo[4,5-b]pyridine (2.48 g), 10% palladium on carbon (containing water (50%), 2.48 g), THF (50 mL) and methanol (50 ml) was stirred under a hydrogen atmosphere at room temperature for 1 hr. The reaction mixture was filtered, and the filtrate was concentrated under reduced pressure. The residue was purified by silica gel column chromatography (hexane/THF) and recrystallized from ethanol to give the title compound (1.38 g).

MS (API+): [M+H]$^+$ 251.0.

D) 9-{4-[(1-Methyl-1H-benzimidazol-2-yl)oxy]phenyl}-9H-imidazo[1',2':1,2]imidazo[4,5-b]pyridine To a solution of 4-(9H-imidazo[1',2':1,2]imidazo[4,5-b]pyridin-9-yl)phenol (150 mg) in DMF (2 mL) was added sodium hydride (60% in oil, 28 mg) at room temperature by small portions. After stirring for 10 min, a solution of 2-chloro-1-methyl-1H-benzimidazole (117 mg) in DMF (1.5 mL) was added, and the obtained mixture was stirred under microwave irradiation at 180° C. for 30 min. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (hexane/THF) and recrystallized from methanol to give the title compound (194 mg).

MS (API+): [M+H]$^+$ 381.2.

mp 232-234° C.

$^1$H NMR (300 MHz, CDCl$_3$) δ 3.77 (3H, s), 7.17-7.26 (4H, m), 7.28 (1H, d, J=1.9 Hz), 7.46 (1H, d, J=1.9 Hz), 7.55-7.62 (3H, m), 7.85 (1H, dd, J=7.9, 1.1 Hz), 8.36 (1H, dd, J=4.9, 1.1 Hz), 8.48-8.53 (2H, m).

Anal. Calcd for C$_{22}$H$_{16}$N$_6$O: C, 69.46; H, 4.24; N, 22.09. Found: C, 69.41; H, 4.30; N, 21.97.

Example 10

1-{2-[4-(9H-imidazo[1',2':1,2]imidazo[4,5-b]pyridin-9-yl)phenoxy]-1H-benzimidazol-1-yl}propan-2-one

A) 1-(2-Chloro-1H-benzimidazol-1-yl)propan-2-one

To a solution of 2-chloro-1H-benzimidazole (1.53 g) in DMF (20 ml) was added sodium hydride (60% in oil, 0.480 g) at 0° C. by small portions. After stirring for 10 min, chloroacetone (1.19 mL) was added, and the obtained mixture was stirred at room temperature for 2 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by silica gel column chromatography (hexane/ethyl acetate) and recrystallized from ethyl acetate to give the title compound (1.73 g).

MS (API+), found: 209.0, 211.0.

B) 1-{2-[4-(9H-imidazo[1',2':1,2]imidazo[4,5-b]pyridin-9-yl)phenoxy]-1H-benzimidazol-1-yl}propan-2-one To a solution of 4-(9H-imidazo[1',2':1,2]imidazo[4,5-b]pyridin-9-yl)phenol (1.13 g) obtained in Example 9, step C) in DMF (10 ml) was added sodium hydride (60% in oil, 0.200 g) at room temperature by small portions. After stirring for 10 min, a solution of 1-(2-chloro-1H-benzimidazol-1-yl)propan-2-one (1.25 g) in DMF (5 ml) was added, and the obtained mixture was stirred under microwave irradiation at 180° C. for 1.5 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (hexane/ethyl acetate) and recrystallized from methanol to give the title compound (0.371 g).

MS (API+): [M+H]$^+$ 423.2.

mp 189-192° C.

$^1$H NMR (300 MHz, CDCl$_3$) δ 2.28 (3H, s), 4.91 (2H, s), 7.06-7.13 (1H, m), 7.18-7.28 (4H, m), 7.46 (1H, d, J=1.5 Hz), 7.54-7.64 (3H, m), 7.85 (1H, dd, J=7.9, 1.5 Hz), 8.36 (1H, dd, J=5.3, 1.5 Hz), 8.49-8.55 (2H, m).

Anal. Calcd for C$_{24}$H$_{18}$N$_6$O$_2$: C, 68.24; H, 4.29; N, 19.89. Found: C, 68.10; H, 4.46; N, 19.70.

Example 11

1-{2-[4-(9H-imidazo[1',2':1,2]imidazo[4,5-b]pyridin-9-yl)phenoxy]-1H-benzimidazol-1-yl}-2-methyl-propan-2-ol To a suspension of cerium chloride(III) (296 mg) in THF (4 ml) was added dropwise 1 M methylmagnesium bromide-THF solution (1.2 ml) at −78° C. After stirring for 10 min, a solution of 1-{2-[4-(9H-imidazo[1',2':1,2]imidazo[4,5-b]pyridin-9-yl)phenoxy]-1H-benzimidazol-1-yl}propan-2-one (338 mg) obtained in Example 10 in THF (20 ml) was added dropwise at −78° C., and the obtained mixture was warmed to room temperature. Water was added to the reaction mixture, and the mixture was extracted with ethyl acetate. The extract was washed with saturated brine, dried over anhydrous magnesium sulfate, and the solvent was evaporated under reduced pressure. The residue was subjected to basic silica gel column chromatography (hexane/ethyl acetate), purified by HPLC (L-Column 2 ODS, 10 mM aqueous hydrogen carbonate ammonium-containing acetonitrile solution) and recrystallized from methanol/water to give the title compound (44.0 mg).

MS (API+): [M+H]$^+$ 439.1.

mp 208-211° C.

$^1$H NMR (300 MHz, CDCl$_3$) δ 1.41 (6H, s), 1.67 (1H, s), 4.18 (2H, s), 7.17-7.28 (4H, m), 7.41-7.48 (2H, m), 7.55-7.61 (3H, m), 7.85 (1H, dd, J=7.9, 1.5 Hz), 8.36 (1H, dd, J=4.9, 1.5 Hz), 8.47-8.53 (2H, m).

Anal. Calcd for C$_{25}$H$_{22}$N$_6$O$_2$-0.2CH$_3$OH: C, 68.03; H, 5.17; N, 18.89.

Found: C, 68.07; H, 5.19; N, 18.97.

Example 12

3-Ethyl-1-{4-[(3-methyl-3H-imidazo[4,5-b]pyridin-2-yl)oxy]phenyl}-1H-pyrazolo[3,4-b]pyridine To a mixture of 4-(3-ethyl-1H-pyrazolo[3,4-b]pyridin-1-yl)phenol (120 mg) obtained in Example 8, step D), sodium hydride (60% in oil, 20.1 mg) and DMF (5.0 ml) was added 3-methyl-2-(methylsulfonyl)-3H-imidazo[4,5-b]pyridine (106 mg), and the mixture was stirred under microwave irradiation at 180° C. for 1 hr. The reaction mixture diluted with methanol, and the mixture was concentrated under reduced pressure. The residue was purified by silica gel column chromatography (hexane/ethyl acetate) to give the title compound (120 mg).

MS (API+): [M+H]$^+$ 371.2.

$^1$H NMR (300 MHz, DMSO-d$_6$) δ 1.34-1.49 (3H, m), 2.98-3.16 (2H, m), 3.33 (3H, s), 7.13-7.27 (1H, m), 7.32-7.43 (1H, m), 7.60-7.70 (2H, m), 7.76-7.85 (1H, m), 8.16-8.26 (1H, m), 8.34-8.48 (3H, m), 8.63-8.73 (1H, m).

Example 13

9-{4-[(3-Methyl-3H-imidazo[4,5-b]pyridin-2-yl)oxy]phenyl}-9H-imidazo[1',2':1,2]imidazo[4,5-b]pyridine To a solution of 4-(9H-imidazo[1',2':1,2]imidazo[4,5-b]pyridin-9-yl)phenol (175 mg) obtained in Example 9, step C) in DMF (2 ml) was added sodium hydride (60% in oil, 32 mg) at room temperature by small portions. After stirring for 10 min, a solution of 3-methyl-2-(methylsulfonyl)-3H-imidazo[4,5-b]pyridine (169 mg) in DMF (1.5 ml) was added, and the obtained mixture was stirred under microwave irradiation at 180° C. for 30 min. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (THF) and recrystallized from methanol/water to give the title compound (179 mg).

MS (API+): [M+H]$^+$ 382.1.

mp 228-231° C.

$^1$H NMR (300 MHz, DMSO-d$_6$) δ 3.79 (3H, s), 7.18-7.23 (2H, m), 7.41 (1H, dd, J=7.9, 5.3 Hz), 7.67-7.72 (2H, m), 7.80 (1H, dd, J=7.9, 1.5 Hz), 7.92 (1H, d, J=1.9 Hz), 8.22 (1H, dd, J=4.9, 1.5 Hz), 8.32 (1H, dd, J=7.9, 1.5 Hz), 8.37 (1H, dd, J=5.3, 1.5 Hz), 8.51-8.56 (2H, m).

Anal. Calcd for C$_{21}$H$_{15}$N$_7$O-0.25H$_2$O: C, 65.36; H, 4.05; N, 25.41.

Found: C, 65.75; H, 4.18; N, 25.12.

Example 14

9-(4-{[3-(2-Methoxyethyl)-3H-imidazo[4,5-b]pyridin-2-yl]oxy}phenyl)-9H-imidazo[1',2':1,2]imidazo[4,5-b]pyridine To a solution of 4-(9H-imidazo[1',2':1,2]imidazo[4,5-b]pyridin-9-yl)phenol (175 mg) obtained in Example 9, step C) in DMF (2 ml) was added sodium hydride (60% in oil, 30 mg) at room temperature by small portions. After stirring for 10 min, a solution of 3-(2-methoxyethyl)-2-(methylsulfonyl)-3H-imidazo[4,5-b]pyridine[191 mg) in DMF (2 ml) was added, and the obtained mixture was stirred under microwave irradiation at 180° C. for 30 min. The reaction mixture was poured into water, and the mixture was extracted with ethyl acetate. The extract was washed with saturated brine, dried over anhydrous magnesium sulfate, and the solvent was evaporated under reduced pressure. The residue was purified by silica gel column chromatography (hexane/THF) and recrystallized from ethanol to give the title compound (198 mg).

MS (API+): [M+H]$^+$ 426.4.

mp 178-182° C.

$^1$H NMR (300 MHz, CDCl$_3$) δ 3.38 (3H, s), 3.88 (2H, t, J=5.7 Hz), 4.51 (2H, t, J=5.7 Hz), 7.14 (1H, dd, J=7.9, 4.9 Hz), 7.25 (1H, dd, J=7.9, 5.3 Hz), 7.28 (1H, d, J=1.5 Hz), 7.46 (1H, d, J=1.5 Hz), 7.56-7.61 (2H, m), 7.79 (1H, dd, J=7.9, 1.5 Hz), 7.86 (1H, dd, J=7.9, 1.5 Hz), 8.23 (1H, dd, J=4.9, 1.5 Hz), 8.36 (1H, dd, J=5.3, 1.5 Hz), 8.53-8.58 (2H, m).

Anal. Calcd for C$_{23}$H$_{19}$N$_7$O$_2$: C, 64.93; H, 4.50; N, 23.05. Found: C, 65.08; H, 4.43; N, 22.96.

Example 15

5-Methyl-9-{4-[(3-methyl-3H-imidazo[4,5-b]pyridin-2-yl)oxy]phenyl}-9H-imidazo[1',2':1,2]imidazo[4,5-b]pyridine A) N-[4-(benzyloxy)phenyl]-4-methyl-3-nitropyridin-2-amine A suspension of 2-chloro-4-methyl-3-nitropyridine (8.63 g), 4-benzyloxyaniline hydrochloride (13.0 g) and triethylamine (20.9 ml) in DMSO (150 ml) was stirred at 120° C. overnight. The reaction mixture was poured into water, and the mixture was extracted with ethyl acetate. The extract was washed with water and saturated brine, dried over anhydrous magnesium sulfate, and the solvent was evaporated under reduced pressure. The residue was recrystallized from hexane/ethyl acetate to give the title compound (10.7 g).

$^1$H NMR (300 MHz, CDCl$_3$) δ 2.57 (3H, s), 5.07 (2H, s), 6.61 (1H, d, J=4.9 Hz), 6.96-7.01 (2H, m), 7.29-7.46 (7H, m), 8.15 (1H, d, J=4.9 Hz), 9.10 (1H, s).

B) N$^2$-[4-(benzyloxy)phenyl]-4-methylpyridine-2,3-diamine

To a mixture of zinc (40.2 g), THF (50 ml) and acetic acid (100 ml) was added slowly a solution of N-[4-(benzyloxy)phenyl]-4-methyl-3-nitropyridin-2-amine (13.75 g) in THF (150 ml), and the obtained mixture was stirred at room temperature for 30 min. The reaction mixture was filtered, and the filtrate was concentrated under reduced pressure. The residue was diluted with ethyl acetate, washed with 1 M aqueous sodium hydroxide solution and saturated brine, dried over anhydrous magnesium sulfate, and the solvent was evaporated under reduced pressure. The residue was purified by basic silica gel column chromatography (hexane/ethyl acetate) and recrystallized from hexane/ethyl acetate to give the title compound (8.77 g).

MS (API+): [M+H]$^+$ 306.1.

C) 3-[4-(Benzyloxy)phenyl]-7-methyl-3H-imidazo[4,5-b]pyridin-2-amine

A mixture of N$^2$-[4-(benzyloxy)phenyl]-4-methylpyridine-2,3-diamine (8.70 g), cyanogen bromide (6.04 g), THF (80 ml) and water (20 ml) was stirred at room temperature for 24 hr. The reaction mixture was poured into saturated aqueous sodium hydrogen carbonate solution, and the mixture was extracted with ethyl acetate. The extract was washed with saturated brine, dried over anhydrous magnesium sulfate, and the solvent was evaporated under reduced pressure. The residue was washed with ethyl acetate, treated with activated carbon, and recrystallized from methanol to give the title compound (5.60 g).

MS (API+): [M+H]$^+$ 331.3.

D) 9-[4-(Benzyloxy)phenyl]-5-methyl-9H-imidazo[1',2':1,2]imidazo[4,5-b]pyridine

A solution of 3-[4-(benzyloxy)phenyl]-7-methyl-3H-imidazo[4,5-b]pyridin-2-amine (4.96 g) and 6.1 M aqueous chloroacetoaldehyde solution (4.92 ml) in DMA (50 ml) was stirred at 100° C. for 2 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by silica gel column chromatography (hexane/THF) and recrystallized from hexane/THF to give the title compound (1.39 g).

MS (API+): [M+H]$^+$ 355.4.

E) 4-(5-Methyl-9H-imidazo[1',2':1,2]imidazo[4,5-b]pyridin-9-yl)phenol

A mixture of 9-[4-(benzyloxy)phenyl]-5-methyl-9H-imidazo[1',2':1,2]imidazo[4,5-b]pyridine (1.35 g), 10% palladium on carbon (containing water (50%), 0.675 g), THF (50 ml) and methanol (50 ml) was stirred under a hydrogen atmosphere at room temperature for 1 hr. The reaction mixture was filtered, and the filtrate was concentrated under reduced pressure. The residue was purified by silica gel column chromatography (hexane/THF) and recrystallized from hexane/THF to give the title compound (0.950 g).

MS (API+): [M+H]$^+$ 265.3.

F) 5-Methyl-9-{4-[(3-methyl-3H-imidazo[4,5-b]pyridin-2-yl)oxy]phenyl}-9H-imidazo[1',2':1,2]imidazo[4,5-b]pyridine To a solution of 4-(5-methyl-9H-imidazo[1',2':1,2]imidazo[4,5-b]pyridin-9-yl)phenol (238 mg) in DMA (4 ml) was added potassium tert-butoxide (112 mg) at room temperature. After stirring for 10 min, 3-methyl-2-(methylsulfonyl)-3H-imidazo[4,5-b]pyridine (211 mg) was added, and the obtained mixture was stirred at 150° C. for 1 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (THF) and recrystallized from hexane/THF to give the title compound (229 mg).

MS (ESI+): [M+H]$^+$ 396.1.

mp 236-239° C.

$^1$H NMR (400 MHz, CDCl$_3$) δ 2.74 (3H, s), 3.86 (3H, s), 7.06 (1H, d, J=5.1 Hz), 7.14 (1H, dd, J=7.8, 4.9 Hz), 7.30 (1H, d, J=1.5 Hz), 7.52 (1H, d, J=1.5 Hz), 7.57-7.61 (2H, m), 7.79 (1H, dd, J=7.8, 1.2 Hz), 8.22-8.25 (2H, m), 8.52-8.56 (2H, m).

Anal. Calcd for C$_{22}$H$_{17}$N$_7$O: C, 66.82; H, 4.33; N, 24.80. Found: C, 66.53; H, 4.46; N, 24.56.

Example 16

9-(4-{[3-(2-Methoxyethyl)-3H-imidazo[4,5-b]pyridin-2-yl]oxy}phenyl)-5-methyl-9H-imidazo[1',2':1,2]imidazo[4,5-b]pyridine To a solution of 4-(5-methyl-9H-imidazo[1',2':1,2]imidazo[4,5-b]pyridin-9-yl)phenol (370 mg) obtained in Example 15, step E) in DMA (3 ml) was added potassium tert-butoxide (168 mg) at room temperature. After stirring for 10 min, a solution of 3-(2-methoxyethyl)-2-(methylsulfonyl)-3H-imidazo[4,5-b]pyridine (383 mg) in DMA (3 ml) was added, and the obtained mixture was stirred at 150° C. for 1 hr. The reaction mixture was poured into water, and the mixture was extracted with ethyl acetate. The extract was washed with water and saturated brine, dried over anhydrous magnesium sulfate, and the solvent was evaporated under reduced pressure. The residue was purified by basic silica gel column chromatography (hexane/THF) and recrystallized from acetone to give the title compound (531 mg).

MS (API+): [M+H]$^+$ 440.3.

mp 190-192° C.

$^1$H NMR (300 MHz, CDCl$_3$) δ 2.74 (3H, s), 3.38 (3H, s), 3.88 (2H, t, J=5.7 Hz), 4.51 (2H, t, J=5.7 Hz), 7.06 (1H, dd, J=5.3, 0.8 Hz), 7.14 (1H, dd, J=7.9, 5.3 Hz), 7.29 (1H, d, J=1.5 Hz), 7.51 (1H, d, J=1.5 Hz), 7.55-7.60 (2H, m), 7.78 (1H, dd, J=7.9, 1.5 Hz), 8.22-8.24 (2H, m), 8.50-8.56 (2H, m).

Anal. Calcd for C$_{24}$H$_{21}$N$_7$O$_2$: C, 65.59; H, 4.82; N, 22.31. Found: C, 65.52; H, 4.87; N, 22.16.

The structural formulas of the above-mentioned Example compounds are shown in the following Tables. In the Tables, MS shows measured values.

TABLE 1-1

| Ex. No. | Compound Name | Structural Formula | salt | MS |
|---|---|---|---|---|
| 1 | 2-[4-(2-methylimidazo[1,2-a]pyridin-8-yl)phenoxy]-1H-benzimidazole | | — | 341.0 |
| 2 | 2-(4-imidazo[1,2-a]pyridin-8-yl)phenoxy]-1H-benzimidazole | | — | 327.1 |
| 3 | 3-[4-(1H-benzimidazol-2-yloxy)phenyl]-2-ethyl-2H-pyrazolo[4,3-b]pyridine | | — | 356.2 |
| 4 | 2-ethyl-3-{4-[(1-methyl-1H-benzimidazol-2-yl)oxy]phenyl}-2H-pyrazolo[4,3-b]pyridine | | — | 370.9 |

TABLE 1-1-continued

| Ex. No. | Compound Name | Structural Formula | salt | MS |
|---|---|---|---|---|
| 5 | 2-[4-(5,6,7,8-tetrahydroimidazo[1,2-a]pyridin-8-yl)phenoxy]-1H-benzimidazole | | — | 331.1 |
| 6 | 1-[4-(1H-benzimidazol-2-yloxy)phenyl]-3-methoxy-1H-pyrazolo[3,4-b]pyridine | | — | 358.3 |

TABLE 1-2

| Ex. No. | Compound Name | Structural Formula | salt | MS |
|---|---|---|---|---|
| 7 | 1-[4-(1H-benzimidazol-2-yloxy)phenyl]-2-methyl-1,2-dihydro-3H-pyrazolo[3,4-b]pyridin-3-one | | — | 358.3 |
| 8 | 3-ethyl-1-{4-[(1-methyl-1H-benzimidazol-2-yl)oxy]phenyl}-1H-pyrazolo[3,4-b]pyridine | | — | 370.2 |
| 9 | 9-{4-[(1-methyl-1H-benzimidazol-2-yl)oxy]phenyl}-9H-imidazo-[1',2':1,2]imidazo[4,5-b]pyridine | | — | 381.2 |

TABLE 1-2-continued

| Ex. No. | Compound Name | Structural Formula | salt | MS |
|---|---|---|---|---|
| 10 | 1-{2-[4-(9H-imidazo[1',2':1,2]imidazo[4,5-b]pyridin-9-yl)phenoxy]-1H-benzimidazol-1-yl}propan-2-one | | — | 423.2 |
| 11 | 1-{2-[4-(9H-imidazo[1',2':1,2]imidazo[4,5-b]pyridin-9-yl)phenoxy]-1H-benzimidazol-1-yl}-2-methylpropan-2-ol | | — | 439.1 |
| 12 | 3-ethyl-1-{4-[(3-methyl-3H-imidazo[4,5-b]pyridin-2-yl)oxy]phenyl}-1H-pyrazolo[3,4-b]pyridine | | — | 371.2 |

TABLE 1-3

| Ex. No. | Compound Name | Structural Formula | salt | MS |
|---|---|---|---|---|
| 13 | 9-{4-[(3-methyl-3H-imidazo[4,5-b]pyridin-2-yl)oxy]phenyl}-9H-imidazo[1',2':1,2]imidazo-[4,5-b]pyridine | | — | 382.1 |
| 14 | 9-(4-{[3-(2-methoxyethyl)-3H-imidazo[4,5-b]pyridin-2-yl]oxy}phenyl)-9H-imidazo[1',2':1,2]imidazo-[4,5-b]pyridine | | — | 426.4 |

TABLE 1-3-continued

| Ex. No. | Compound Name | Structural Formula | salt | MS |
|---|---|---|---|---|
| 15 | 5-methyl-9-{4-[(3-methyl-3H-imidazo[4,5-b]pyridin-2-yl)oxy]phenyl}-9H-imidazo[1',2':1,2]imidazo-[4,5-b]pyridine | | — | 396.1 |
| 16 | 9-(4-{[3-(2-methoxyethyl)-3H-imidazo[4,5-b]pyridin-2-yl]oxy}phenyl)-5-methyl-9H-imidazo[1',2':1,2]imidazo-[4,5-b]pyridine | | — | 440.3 |

Formulation Example 1

| | |
|---|---|
| (1) Compound of the Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

After 10.0 g of the compound of Example 1 and 3.0 g of magnesium stearate are granulated in 70 ml aqueous solution of soluble starch (7.0 g as soluble starch) and then dried, the resulting mixture is mixed with 70.0 g of lactose and 50.0 g of cornstarch (lactose, cornstarch, soluble starch, and magnesium stearate are all the Japanese Pharmacopoeia compatible products). The mixture is compressed to obtain a tablet.

Experimental Example

PDE10A Enzyme Activity Inhibition Test

Human PDE10A full-length gene was transfected into Sf9 or COS-7 cells. The cells were disrupted and centrifuged, and human PDE10A enzyme was obtained from the residue. The enzyme extracted from Sf9 cells was partially purified using His-tag affinity column. The enzyme was stored at −70° C. until use.

The PDE 10A enzyme activity was measured using an Scintillation Proximity Assay (SPA, GE Healthcare). To measure the inhibitory activity of the test compound, 10 μL of serially diluted test compound was reacted with 20 μL of PDE 10A enzyme in an assay buffer (50 mM HEPES-NaOH, 8.3 mM $MgCl_2$, 1.7 mM EGTA, 0.1% BSA (pH 7.4)) for 30 min at room temperature. The final concentration of DMSO in the reaction mixture was 1%.

The compounds were evaluated in duplicate in 96-well half-area plates (Corning). To start the reaction, 10 μL of substrate [3H] cGMP (25 or 50 nM; GE Healthcare and PerkinElmer, respectively) was added thereto to the total volume of 40 μL. After 60 min of reaction at room temperature, yttrium SPA beads containing zinc sulphate were added (6 mg/mL, 20 μL) to terminate the reaction. After standing still for 1 hr, the measurement was performed using a scintillation counter (PerkinElmer) and the inhibition rate was calculated. As for the inhibitory rate, the value without addition of the compound (control) was 0%, and that without addition of the compound and enzyme was 100%. The results are shown in Table 2.

TABLE 2

| Ex. No. | Inhibitory rate (%) (10 μM) | Inhibitory rate (%) (0.1 μM) |
|---|---|---|
| 1 | 98 | 63 |
| 2 | 98 | 62 |
| 3 | 102 | 91 |
| 4 | 102 | 93 |
| 5 | 51 | 2 |
| 6 | — | 99 |
| 7 | — | 59 |
| 8 | 104 | 93 |
| 9 | 96 | 93 |
| 10 | 109 | 104 |
| 11 | 106 | 104 |
| 12 | 101 | 99 |
| 13 | 106 | 97 |
| 14 | 105 | 96 |
| 15 | 95 | 97 |
| 16 | 105 | 98 |

Experimental Example 2

Animal

Male SD rats were purchased from Charles River Laboratories Japan, Inc. (Kanagawa, Japan), and used for the experiment at the age of 8 weeks. After arrival at the vivarium, the animals were acclimated for at least 1 week. The animals were reared under a 12:12 hr light/dark cycle in a temperature- and humidity-controlled laboratory and allowed to freely take food and water.

Drug Administration

Example 14 was suspended in 0.5% (w/v) aqueous methylcellulose solution and orally administered (p.o.). (+)-MK-801 hydrogen maleate (MK-801, Sigma-Aldrich, St Louis, State of Missouri) was dissolved in saline, and subcutaneously administered (s.c.). All drugs were dosed in a volume of 2 mL/kg body weight for rats.

Study of Suppressive Action on Hyperlocomotion Induced by MK-801

Hyperlocomotion induced by psychostimulants (e.g., amphetamine, cocaine, methamphetamine, MK-801 and phencyclidine) in rodents is widely used as an animal model of psychosis (Psychopharmacology 1999, vol. 145: 237-250). Using rats, a suppressive action of a compound (Example 14) on the hyperlocomotion induced by MK-801 was tested. Until the start of the test, male SD rats (8-week-old) were acclimated in a locomotor chamber with an infrared sensor set on the upper side (Muromachi Kikai Co., Ltd., Tokyo, Japan). After acclimation, the animals were treated with either vehicle (0.5% (w/v) aqueous methylcellulose solution) or Example 14 (1 mg/kg, p.o.) and, 60 min later, MK-801 (0.3 mg/kg as salt, s.c.) was administered. Hyperlocomotion was measured every 1 min, and the cumulative count for 120 min from the administration of MK-801 was calculated for each treatment group. All data are shown as mean±standard error (n=5), and the statistical analysis was performed by Student's t-test (significant difference at $P<0.05$).

As a result, Example 14 (1 mg/kg, p.o.) significantly suppressed hyperlocomotion induced by MK-801 (0-120 min), by the administration 60 min before MK-801 treatment (0.3 mg/kg, s.c.) (FIG. 1).

INDUSTRIAL APPLICABILITY

Since the compound of the present invention shows a superior PDE10A inhibitory action, it can provide a prophylactic or therapeutic drug which is clinically useful for diseases such as schizophrenia and the like. Moreover, since the compound of the present invention is superior in efficacy, lower toxicity, stability, in vivo kinetics and the like, it is useful as a medicament.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on a patent application No. 2011-058562 filed in Japan, the contents of which are incorporated in full herein.

The invention claimed is:

1. A compound represented by the formula (I-i):

(I-i)

wherein
R$^1$ is a hydrogen atom or an optionally substituted C$_{1-6}$ alkyl group,
X$^1$ is CH or a nitrogen atom,
ring A optionally has a substituent,
X$^2$ is CR$^2$ or a nitrogen atom,
X$^3$ is CR$^3$ or a nitrogen atom,
X$^4$ is CR$^4$ or a nitrogen atom,
X$^5$ is CR$^5$ or a nitrogen atom,
R$^2$, R$^3$, R$^4$ and R$^5$ are each independently a hydrogen atom or a substituent,
ring B is an optionally substituted 5- or 6-membered nitrogen-containing heterocycle (said nitrogen-containing heterocycle optionally further forms a fused ring with a ring other than ring C$^1$),
Z$^5$ is =N— or —N=,
ring C$^1$ is an optionally substituted 5-membered ring,
Z$^1$, Z$^{3'}$ and Z$^{4'}$ are each independently a ring C$^1$-constituting atom selected from a carbon atom and a nitrogen atom,
ring D is an optionally substituted 5- or 6-membered ring, and
------ is a single bond or a double bond,
or a salt thereof.

2. A compound represented by the formula (I-ii):

(I-ii)

wherein
R$^1$ is a hydrogen atom or an optionally substituted C$_{1-6}$ alkyl group,
X$^1$ is CH or a nitrogen atom,
ring A optionally has a substituent,
X$^2$ is CR$^2$ or a nitrogen atom,
X$^3$ is CR$^3$ or a nitrogen atom,
X$^4$ is CR$^4$ or a nitrogen atom,
X$^5$ is CR$^5$ or a nitrogen atom,
R$^2$, R$^3$, R$^4$ and R$^5$ are each independently a hydrogen atom or a substituent, ring B is an optionally substituted 5- or 6-membered nitrogen-containing heterocycle (said nitrogen-containing heterocycle optionally further forms a fused ring with a ring other than ring $C^2$), $Z^5$ is =N— or —N=, ring $C^2$ is an optionally substituted 5-membered ring, Y is a ring $C^2$-constituting atom selected from a carbon atom and a nitrogen atom, $Z^1$ is a ring $C^2$-constituting atom selected from a carbon atom and a nitrogen atom, $Z^{3"}$ is a ring $C^2$-constituting atom selected from a carbon atom, a nitrogen atom, a sulfur atom and an oxygen atom, $Z^{4"}$ is —O—, —S—, —N=, —NR$^{6'}$—, —CR$^{7'}$=, —SO—, —SO$_2$— or an optionally substituted methylene group (excluding a carbonyl group), $R^{6'}$ and $R^{7'}$ are each independently a hydrogen atom or a substituent, and

- - - - - - is a single bond or a double bond, or a salt thereof.

3. A compound represented by the formula (I-iii):

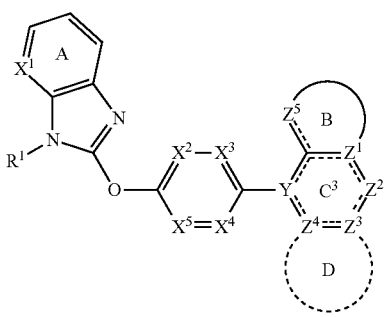

(I-iii)

wherein $R^1$ is a hydrogen atom or an optionally substituted $C_{1-6}$ alkyl group, $X^1$ is CH or a nitrogen atom, ring A optionally has a substituent, $X^2$ is $CR^2$ or a nitrogen atom, $X^3$ is $CR^3$ or a nitrogen atom, $X^4$ is $CR^4$ or a nitrogen atom, $X^5$ is $CR^5$ or a nitrogen atom, $R^2$, $R^3$, $R^4$ and $R^5$ are each independently a hydrogen atom or a substituent, ring B is an optionally substituted, 5- or 6-membered nitrogen-containing heterocycle (said nitrogen-containing heterocycle optionally further forms a fused ring with a ring other than ring $C^3$), $Z^5$ is =N— or —N=, ring $C^3$ is an optionally substituted 6-membered ring, Y is a ring $C^3$-constituting atom selected from a carbon atom and a nitrogen atom, $Z^1$ is a ring $C^3$-constituting atom selected from a carbon atom and a nitrogen atom, $Z^2$, $Z^3$ and $Z^4$ are each independently a ring $C^3$-constituting atom selected from a carbon atom, a nitrogen atom, a sulfur atom and an oxygen atom, and

- - - - - - is a single bond or a double bond, or $Z^3$ and $Z^4$ are optionally joined to form ring D, and ring D is an optionally substituted 5- or 6-membered ring, or a salt thereof.

4. The compound according to claim 2, wherein $Z^{4"}$ is —O—, —S—, —N=, —NR$^{6'}$—, —CR$^{7'}$=, —SO—, —SO$_2$— or —CR$^8$R$^9$—(R$^8$ and R$^9$ are each independently a hydrogen atom or a substituent), or a salt thereof.

5. The compound according to any one of claims 1 to 3, wherein $X^2$, $X^3$, $X^4$ and $X^5$ are each CH, or a salt thereof.

6. The compound according to claim 1, which is represented by the formula (I-i)':

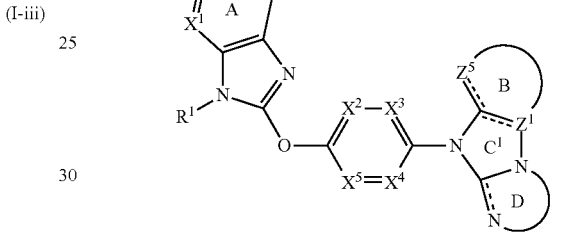

(I-i)' wherein each symbol is as defined in claim 1, or a salt thereof.

7. 9-(4-{[3-(2-Methoxyethyl)-3H-imidazo[4,5-b]pyridin-2-yl]oxy}phenyl)-9H-imidazo[1',2':1,2]imidazo[4,5-b]pyridine or a salt thereof.

8. 5-Methyl-9-{4-[(3-methyl-3H-imidazo[4,5-b]pyridin-2-yl)oxy]phenyl}-9H-imidazo[1',2':1,2]imidazo[4,5-b]pyridine or a salt thereof.

9. A medicament comprising a compound according to any one of claims 1 to 3, or a salt thereof.

10. The medicament according to claim 9, which is a phosphodiesterase 10A inhibitor.

11. The medicament according to claim 9, which is an agent for the treatment of schizophrenia.

12. A method for the treatment of schizophrenia in a mammal, comprising administering an effective amount of a compound according to any one of claims 1 to 3, or a salt thereof, to the mammal.

13. A compound according to any one of claims 1 to 3, or a salt thereof, for the use in the treatment of schizophrenia.

\* \* \* \* \*